(12) United States Patent
Smith et al.

(10) Patent No.: US 7,442,381 B2
(45) Date of Patent: Oct. 28, 2008

(54) ALPHAVIRUS REPLICONS AND HELPER CONSTRUCTS

(75) Inventors: Jonathan F. Smith, Cary, NC (US); Kurt I. Kamrud, Apex, NC (US); Jon O. Rayner, Apex, NC (US)

(73) Assignee: AlphaVax, Inc., Research Triangle Park, NC (US)

( * ) Notice: Subject to any disclaimer, the term of this patent is extended or adjusted under 35 U.S.C. 154(b) by 0 days.

(21) Appl. No.: 10/804,331

(22) Filed: Mar. 19, 2004

(65) Prior Publication Data

US 2007/0166820 A1    Jul. 19, 2007

Related U.S. Application Data

(60) Provisional application No. 60/456,196, filed on Mar. 20, 2003.

(51) Int. Cl.
*A01N 63/00* (2006.01)
*A61K 39/12* (2006.01)
*C07H 21/04* (2006.01)

(52) U.S. Cl. .................. 424/218.1; 536/23.1; 424/93.1

(58) Field of Classification Search ....................... None
See application file for complete search history.

(56) References Cited

U.S. PATENT DOCUMENTS

| | | | |
|---|---|---|---|
| 4,650,764 A | 3/1987 | Temin | |
| 4,708,871 A | 11/1987 | Geysen | |
| 5,091,309 A | 2/1992 | Schlesinger | |
| 5,185,440 A | 2/1993 | Davis | |
| 5,217,879 A | 6/1993 | Huang | |
| 5,505,947 A | 4/1996 | Johnston | |
| 5,521,082 A | 5/1996 | Lewis et al. | |
| 5,639,650 A | 6/1997 | Johnston | |
| 5,643,576 A | 7/1997 | Johnston | |
| 5,703,057 A | 12/1997 | Johnston et al. | |
| 5,726,022 A | 3/1998 | Burmer | |
| 5,739,026 A | 4/1998 | Garoff | |
| 5,766,602 A | 6/1998 | Xiong | |
| 5,789,245 A | 8/1998 | Dubensky | |
| 5,792,462 A | 8/1998 | Johnston | |
| 5,811,407 A | 9/1998 | Johnston | |
| 5,814,482 A | 9/1998 | Dubensky | |
| 5,827,658 A | 10/1998 | Liang et al. | |
| 5,831,016 A | 11/1998 | Wang et al. | |
| 5,843,723 A | 12/1998 | Dubensky et al. | |
| 5,853,719 A | 12/1998 | Nair et al. | |
| 5,958,738 A | 9/1999 | Lindermann et al. | |
| 5,989,553 A | 11/1999 | Johnston et al. | |
| 6,008,035 A | 12/1999 | Johnston | |
| 6,015,686 A | 1/2000 | Dubensky | |
| 6,015,694 A | 1/2000 | Dubensky | |
| 6,146,874 A | 11/2000 | Zolutukhin | |
| 6,156,558 A | 12/2000 | Johnston | |
| 6,190,666 B1 | 2/2001 | Garoff | |
| 6,194,191 B1 | 2/2001 | Zhang et al. | |
| 6,197,502 B1 | 3/2001 | Renner et al. | |
| 6,224,879 B1 | 5/2001 | Sjoberg et al. | |
| 6,242,259 B1 | 6/2001 | Polo | |
| 6,261,570 B1 | 7/2001 | Parker | |
| 6,267,967 B1 | 7/2001 | Johnston et al. | |
| 6,306,388 B1 | 10/2001 | Nair et al. | |
| 6,329,201 B1 | 12/2001 | Polo | |
| 6,342,372 B1 | 1/2002 | Dubensky | |
| 6,376,236 B1 | 4/2002 | Dubensky | |
| 6,391,632 B1 | 5/2002 | Dubensky | |
| 6,426,196 B1 | 7/2002 | Dubensky | |
| 6,485,958 B2 | 11/2002 | Blanche et al. | |
| 6,495,143 B2 | 12/2002 | Lee et al. | |
| 6,521,235 B2 | 2/2003 | Johnston et al. | |
| 6,531,135 B1 | 3/2003 | Johnston et al. | |
| 6,541,010 B1 | 4/2003 | Johnston et al. | |

(Continued)

FOREIGN PATENT DOCUMENTS

WO    WO 92/10578    6/1992

(Continued)

OTHER PUBLICATIONS

Davis et al. "Alphavirus Replicon Particles as Candidate HIV Vaccines" *IUBMB Life* 53: 209-211 (2002).
Baric et al. "Expression and Self-Assembly of Norwalk Virus Capsid Protein from Venezuelan Equine Encephalitis Virus Replicons" *Journal of Virology* 76(6): 3023-3030 (2002).
Eiben et al. "Establishment of an HLA-A*0201 Human Papillomavirus Type 16 Tumor Model to Determine the Efficacy of Vaccination Strategies in HLA-A*0201 Transgenic Mice" *Cancer Research* 62: 5792-5799 (2002).
Eralp et al. "Doxorubicin and Paclitaxel Enhance the Antitumor Efficacy of Vaccines Directed Against HER 2/neu in a Murine Mammary Carcinoma Model" *Breast Cancer Research* 6:R275-R283 (2004).
Lee et al. "Candidate Vaccine Against Botulinum Neurotoxin Serotype A Derived from a Venezuelan Equine Encephalitis Virus Vector System" *Infection and Immunity* 69(9): 5709-5715 (2001).

(Continued)

*Primary Examiner*—Bruce Campell
*Assistant Examiner*—Benjamin P Blumel
(74) *Attorney, Agent, or Firm*—Myers Bigel Sibley & Sajovec, P.A.

(57) ABSTRACT

The present invention provides a recombinant nucleic acid comprising: a first nucleic acid sequence encoding a 5' alphavirus replication recognition sequence; at least one second nucleic acid sequence encoding an alphavirus nonstructural protein; at least one alphavirus subgenomic promoter; at least one IRES element; at least one heterologous nucleic acid; and a third nucleic acid encoding a 3' alphavirus replication recognition sequence. Further provided are methods of making alphavirus particles comprising a recombinant nucleic acid of this invention and methods of using the compositions of this invention. Also provided is a recombinant helper nucleic acid comprising: a first nucleic acid sequence encoding a 5' alphavirus replication recognition sequence; an alphavirus subgenomic promoter; an IRES element; a second nucleic acid encoding an alphavirus structural protein; and a third nucleic acid encoding a 3' alphavirus replication recognition sequence.

94 Claims, 1 Drawing Sheet

U.S. PATENT DOCUMENTS

| | | | |
|---|---|---|---|
| 6,583,121 | B1 | 6/2003 | Johnston et al. |
| 6,767,699 | B2 | 7/2004 | Polo et al. |
| 6,770,283 | B1 | 8/2004 | Garoff et al. |
| 6,783,939 | B2 | 8/2004 | Olmsted et al. |
| 6,844,188 | B1 | 1/2005 | MacDonald et al. |
| 7,045,335 | B2 | 5/2006 | Smith et al. |
| 2001/0016199 | A1 | 8/2001 | Johnston et al. |
| 2002/0018766 | A1 | 2/2002 | Roberts et al. |
| 2002/0034521 | A1 | 3/2002 | Lee et al. |
| 2002/0102273 | A1 | 8/2002 | Grieve et al. |
| 2002/0141975 | A1 | 10/2002 | Olmsted et al. |
| 2002/0164582 | A1 | 11/2002 | Hart et al. |
| 2003/0021766 | A1 | 1/2003 | Vadjy et al. |
| 2003/0091591 | A1 | 5/2003 | Xiong et al. |
| 2003/0096397 | A1 | 5/2003 | Schlesinger et al. |
| 2003/0119182 | A1 | 6/2003 | Rayner et al. |
| 2003/0120060 | A1 | 6/2003 | Gonczol et al. |
| 2003/0148262 | A1 | 8/2003 | Polo et al. |
| 2003/0152590 | A1 | 8/2003 | Hevey et al. |
| 2003/0232036 | A1 | 12/2003 | Johnston et al. |
| 2003/0232324 | A1 | 12/2003 | Polo et al. |
| 2004/0008458 | A1 | 1/2004 | Kase et al. |
| 2004/0009183 | A1 | 1/2004 | Lee et al. |
| 2004/0009945 | A1 | 1/2004 | Lee et al. |
| 2004/0029279 | A1 | 2/2004 | Kovacs et al. |
| 2004/0030117 | A1 | 2/2004 | Johnston et al. |
| 2004/0055037 | A1 | 3/2004 | Gleba |
| 2004/0088764 | A1 | 5/2004 | Gleba |
| 2004/0121466 | A1 | 6/2004 | Johnston et al. |
| 2004/0146859 | A1 | 7/2004 | Hart et al. |
| 2004/0166573 | A1 | 8/2004 | Smith et al. |
| 2004/0208848 | A1 | 10/2004 | Smith et al. |
| 2004/0255347 | A1 | 12/2004 | Klimyuk |
| 2005/0014150 | A1 | 1/2005 | Atabekov |
| 2005/0031592 | A1 | 2/2005 | Doolan et al. |
| 2005/0054107 | A1 | 3/2005 | Chulay et al. |
| 2005/0059004 | A1 | 3/2005 | Atabekov |
| 2005/0118251 | A1 | 6/2005 | Nagata et al. |
| 2005/0123555 | A1 | 6/2005 | Olmsted et al. |
| 2006/0177819 | A1 | 8/2006 | Smith et al. |

FOREIGN PATENT DOCUMENTS

| | | |
|---|---|---|
| WO | WO 95/07994 | 3/1995 |
| WO | WO 95/27044 | 10/1995 |
| WO | WO 95/31565 | 11/1995 |
| WO | WO 96/17072 | 6/1996 |
| WO | WO 96/37220 | 11/1996 |
| WO | WO 96/37616 | 11/1996 |
| WO | WO 99/07834 | 2/1999 |
| WO | WO 99/08706 | 2/1999 |
| WO | WO 99/51263 | 10/1999 |
| WO | WO 00/39302 | 7/2000 |
| WO | WO 00/39318 | 7/2000 |
| WO | WO 00/61772 | 10/2000 |
| WO | WO 01/16343 A1 | 3/2001 |
| WO | WO 02/03917 | 1/2002 |
| WO | WO 02/04493 | 1/2002 |
| WO | WO 02/10578 A1 | 2/2002 |
| WO | WO 02/20721 | 3/2002 |
| WO | WO 03/023026 A | 3/2003 |
| WO | WO 03/083065 A2 | 10/2003 |
| WO | WO 2004/055166 | 7/2004 |
| WO | WO 2004/055167 | 7/2004 |
| WO | WO 2004/085660 | 10/2004 |
| WO | WO 2005/007689 | 1/2005 |

OTHER PUBLICATIONS

Lee et al. "Immune Protection Against Staphylococcal Enterotoxin-Induced Toxic Shock by Vaccination with a Venezuelan Equine Encephalitis Virus Replicon" *Journal of Infectious Diseases* 185: 1192-1196 (2002).

MacDonald et al. "Role of Dendritic Cell Targeting in Venezuelan Equine Encephalitis Virus Pathogenesis" *Journal of Virology* 74(2): 914-922 (2000).

Nelson et al. "Venezuelan Equine Encephalitis Replicon Immunization Overcomes Intrinsic Tolerance and Elicits Effects Anti-Tumor Immunity to the "self" Tumor-Associated Antigen, neu in a Rat Mammary Tumor Model" *Breast Cancer Research and Treatment* 63R: 1-15 (2003).

Pushko et al. "Individual and Bivalent Vaccines Based on Alphavirus Replicons Protect Guinea Pigs Against Infection with Lassa and Ebola Viruses" *Journal of Virology* 75(23): 11677-11685 (2001).

Schultz-Cherry et al. "Influenza Virus (A/HK/156/97) Hemagglutinin Expressed by an Alphavirus Replicon System Protects Chickens Against Lethal Infection with Hong Kong-Origin H5N1 Viruses" *Virology* 278: 55-59 (2000).

Wang et al. "Alphavirus Replicon Particles Containing the Gene for HER2/neu Inhibit Breast Cancer Growth and Tumorigenesis" *Breast Cancer Research* 7: R145-R155 (2005).

Velders et al. "Eradication of Established Tumors by Vaccination with Venezuelan Equine Encephalitis Virus Replicon Particles Delivering Human Papillomavirus 16 E7 RNA" *Cancer Research* 61: 7861-7867 (2001).

Wilson et al. "Protection from Ebola Virus Mediated by Cytotoxic T Lymphocytes Specific for the Viral Nucleoprotein" *Journal of Virology* 75(6): 2660-2664 (2001).

Gidwitz et al. "Differences in virion stability among Sindbis virus pathogenesis mutants" Virus Research 10:225-240 (1988).

Johnston et al. "Studies of Alphavirus Virulence Using Full-Length Clones of Sindbis and Venezuelan Equine Encephalitis Viruses" M.A. Brinton et al. (eds), *News Aspects of Positive Strand RNA Viruses*, pp. 334-339, ASM Press (1990).

Kaufman et al. "Improved vectors for stable expression of foreign genes in mammalian cells by use of the untranslated leader sequence from EMC virus" Nucleic Acids Research 19(16):4485-4490 (1991).

Khromykh. "Replicon-based vectors of positive strand RNA viruses" Current Opinion in Molecular Therapeutics 2(5):555-569 (2000).

Lemm et al. "Assembly of Functional Sindbis Virus RNA Replication Complexes: Requirement for Coexpression of P123 and P34" Journal of Virology 67(4):1905-1915 (1993).

Olmsted et al. "Sindbis Virus Mutants Selected for Rapid Growth in Cell Culture Display Attenuated Virulence in Animals" Science 225(4660):424-427 (1984).

Polo et al. "A Model for In Vitro Development of Live, Recombinant Alphavirus Vaccines" *Vaccines 90: Modern Approaches to New Vaccines Including Prevention of AIDS*, pp. 105-108, Brown et al. (eds), Cold Spring Harbor Laboratory, 1990.

Polo et al. "Mutational Analysis of Virulence Locus in the E2 Glycoprotein Gene of Sindbis Virus" Journal of Virology 65(11):6358-6361 (1991).

Tugizov et al. "Mutated Forms of Human Cytomegalovirus Glycoprotein B Are Impaired in Inducing Syncytium Formation" Virology 209:580-591 (1995).

Vaz-Santiago "Ex Vivo Stimulation and Expansion of both CD4+ and CD8+ T Cells from Peripheral Blood Mononuclear Cells of Human Cytomegalovirus-Seropositive Blood Donors by Using a Soluble Recombinant Chimeric Protein, IE1-pp65" Journal of Virology 75(17):7840-7847 (2001).

International Search Report corresponding to PCT/US2004/008458, mailed on Oct. 25, 2004.

Knight "Secretion from Bovine Chromaffin Cells Acutely Expressing Exogenous Proteins using a Recombinant Semliki Forest Virus Containing an EGFP Reporter" *Molecular and Cellular Neuroscience* 14(6):486-505 (1999).

Kohl et al. "Transient Gene Expression in Mammalian and Mosquito Cells Using a Recombinant Semliki Forest Virus Expressing T7 RNA Polymerase" *Applied Microbiology and Biotechnology* 53(1):51-56 (1999).

Pugachev et al. "Development of a Rubella Virus Vaccine Expression Vector: Use of a Picornavirus Internal Ribosome Entry Site Increases Stability of Expression" *Journal of Virology* 74(22):10811-10815 (2000).

Rayner et al. "Alphavirus Vectors and Vaccination" *Reviews in Medical Virology* 12(5):279-296 (2002).
Shi Pei-Yong et al. "Construction and Characterization of Subgenomic Replicons of New York Strain of West Nile Virus" *Virology* 296(2):219-233 (2002).
Wang et al. "Core Protein-Coding Sequence, But Not Core Protein, Modulates the Efficiency of Cap-Independent Translation Directed by the Internal Ribosome Entry Site of Hepatitis C Virus" *Journal of Virology* 74(23):11347-11358 (2000).
Wen Xiao-Yan et al. "Tricistronic Viral Vectors Co-Expressing Interleukin-12 (IL-12) and CD80 (B7-1) for the Immunotherapy of Cancer: Preclinical Studies in Myeloma" *Cancer Gene Therapy* 8(5):361-370 (2001).
Wilson et al. "Naturally Occurring Dicistronic Cricket Paralysis Virus RNA is Regulated by Two Internal Ribosome Entry Sites" *Molecular and Cellular Biology* 20(14):4990-4999 (2000).
Balasuriya et al. "Alphavirus Replicon Particles Expressing the Two Major Envelope Proteins of Equine Arteritis Virus Induce High Level Protection Against Challenge with Virulent Virus in Vaccinated Horses" Vaccine 20:1609-1617 (2002).
Barry et al. "Expression Library Immunization to Discover and Improve Vaccine Antigens" Immunological Reviews 199:68-83 (2004).
Bell et al. "Effect of Low NaCl Medium on the Envelope Glycoproteins of Sindbis Virus" Journal of Virology 25(3):764-769 (1978).
Bergman et al. "Long-Term Survival of Dogs with Advanced Malignant Melanoma after DNA Vaccination with Xenogeneic Human Tyrosinase: A Phase I Trial" Clin. Cancer Research 9:1284-1290 (2003).
Bernard et al. "Mutations in the E2 Glycoprotein of Venezuelan Equine Encephalitis Virus Confer Heparan Sulfate Interaction, Low Morbidity, and Rapid Clearance from Blood of Mice" Virology 276:93-103 (2000).
Bourne et al. "Preconception Immunization with a Cytomegalovirus (CMV) Glycoprotein Vaccine Improves Pregnancy Outcome in a Guinea Pig Model of Congenital CMV Infection" The Journal of Infectious Diseases 183:59-64 (2001).
Carlson et al. "Expression, Purification and Characterization of a Soluble Form of Human Cytomegalovirus Glycoprotein B" Virology 239:198-205 (1997).
Casimiro et al. "Vaccine-Induced Immune Responses in Rodents and Nonhuman Primates by Use of a Humanized Immunodeficiency Virus Type 1 pol Gene" Journal of Virology 76:185-195 (2002).
Chatterjee et al. "Modification of Maternal and Congenital Cytomegalovirus Infection by Anti-Glycoprotein B Antibody Transfer in Guinea Pigs" The Journal of Infectious Diseases 183:1547-1553 (2001).
Davis et al. "A Single Nucleotide Change in the E2 Glycoprotein Gene of Sindbis Virus Affects Penetration Rate in Cell Culture and Virulence in Neonatal Mice" Proc. Natl. Acad. Sci. USA 83:6771-6775 (1986).
Davis et al. 1989. In Vitro Synthesis of Infectious Venezuelan Equine Encephalitis Virus RNA from a cDNA Clone: Analysis of A Viable Deletion Mutant. Virology 171:189-204.
Geisbert et al. "Evaluation in Nonhuman Primates of Vaccines Against Ebola Virus" Emerging Infect. Dis. 8(5):503-507 (2002).
Geysen et al. "A Priori Delineation of a Peptide which Mimics a Discontinuous Antigenic Determinant" Molecular Immunology 23(7):709-715 (1986).
Geysen et al. "Use of Peptide Synthesis to Probe Viral Antigens for Epitopes to a Resolution of a Single Amino Acid" Proceedings of the National Academy of Sciences of the United States of America 81(13):3998-4002(1984).
Golzio et al. "Cell Synchronization Effect on Mammalian Cell Permeabilization and Gene Delivery by Electronic Field" Biochim. Biophys. Acta 1563:23-28 (2002).
Gonczol and Plotkin "Development of a Cytomegalovirus Vaccine: Lessons from Recent Clinical Trials" Exp. Opin. Biol. Ther. 1(3):401-412 (2001).
Gyulai et al. "Cytotoxic T Lymphocyte (CTL) Responses to Human Cytomegalovirus pp65, IE1-Exon4, gB, pp150, and pp28 in Healthy Individuals: Reevaluation of Prevalence of IE1-Specific CTLs" J. Infect. Dis. 181:1537-1546(2000).
Hahn et al. "Infectious Sindbis Virus Transient Expression Vectors for Studying Antigen Processing and Presentation" Proc. Natl. Acad. Sci. USA 89:2679-2683 (1992).
Hariharan et al. "DNA Immunization Against Herpes Simplex Virus: Enhanced Efficacy Using a Sindbis Virus-Based Vector" Journal of Virology 72(2):950-958 (1998).
Heiser et al. "Autologous Dendritic Cells Transfected with Prostate-Specific Antigen RNA Stimulate CTL Responses Against Metastatic Prostate Tumors" J. Clinical Inv. 109(3):409-417 (2002).
Hevey et al. "Marburg Virus Vaccines Based upon Alphavirus Replicons Protect Guinea Pigs and Nonhuman Primates" Virology 251:28-37 (1998).
Hill et al. "RNA-RNA Recombination in Sindbis Virus: Roles of the 3' Conserved Motif, Poly (A) Tail, and Nonviral Sequences of Template RNAs in Polymerase Recognition and Template Switching" Journal of Virology 71:2693-2704 (1997).
International Search Report issued for PCT/2004/021772; mailed on Dec. 28, 2004.
International Search Report issued for PCT/US03/39723; mailed on Aug. 17, 2004.
International Search Report issued for PCT/US03/39725; mailed on Dec. 3, 2004.
Koller et al. "A High-Throughput Alphavirus-Based Expression Cloning System for Mammalian Cells" Nature Biotech. 19:851-855 (2001).
Kumamoto et al. "Induction of Tumor-Specific Protective Immunity by in situ Langerhans Cells Vaccine" Nature Biotech. 20:64-69 (2002).
Leitner et al. "Enhancement of Tumor-Specific Immune Response with Plasmid DNA Replicon Vectors" Cancer Research 60:51-55 (2000).
Liljestrom et al. "In Vitro Mutagenesis of a Full-Length cDNA Clone of Semliki Forest Virus: the Small 6,000-Molecular-Weight Membrane Protein Modulates Virus Release" Journal of Virology 65:4107-4113 (1991).
Lu et al. "Transmission of Replication-Defective Sindbis Helper Vectors Encoding Capsid and Envelope Proteins" Journal of Virological Methods 91(1):59-65 (2001).
Lundstrom "Alphavirus Vectors: Applications for DNA Vaccine Production and Gene Expression" Intervirology 43:247-257 (2000).
Maecker et al. "Use of Overlapping Peptide Mixtures as Antigens for Cytokine Flow Cytometry" Journal of Immunological Methods 255:27-40 (2001).
McCue and Anders "Soluble Expression and Complex Formation of Proteins Required for HCMV DNA Replication Using the SFV Expression System" Protein Expression and Purification 13:301-312 (1998).
Morello et al. "Suppression of Murine Cytomegalovirus (MCMV) Replication with a DNA Vaccine Encoding MCMV M84 (a Homolog of Human Cytomegalovirus pp65)" Journal of Virology 74(8):3696-3708 (2000).
Olmsted et al. "Alphavirus Vectors and Virosomes with Modified HIV Genes for Use in Vaccines" U.S. Appl. No. 10/929,234, filed in the U.S. Patent and Trademark Office on Aug. 30, 2004.
Olmsted et al. "Characterization of Sindbis Virus Epitopes Important for Penetration in Cell Culture and Pathogenesis in Animals" Virology 148:245-254 (1986).
Overwijk et al. "Creating Therapeutic Cancer Vaccines: Notes from the Battlefield" Trends in Immunol. 22(1):5-7 (2001).
Pardoll "Cancer Vaccines" Nature Medicine Vaccine Supplement 4(5):525-531 (1998).
Pardoll "Spinning Molecular Immunology into Successful Immunotherapy" Nature Reviews—Immunology 2:227-238 (2002).

Pedersen et al. "Separation, Isolation, and Immunological Studies of the Structural Proteins of Venezuelan Equine Encephalomyelitis Virus" J. Virology 14(4):740-744 (1974).

Plotkin et al. "Multicenter Trial of Towne Strain Attenuated Virus Vaccine in Seronegative Renal Transplant Recipients" Transplantation 58(11):1176-1178 (1994).

Polo et al. "Stable Alphavirus Packaging Cell Lines for Sindbis Virus and Semliki Forest Virus-Derived Vectors" Proc. Natl. Acad. Sci. 96:4598-4603 (1999).

Ragupathi et al. "The Case for Polyvalent Cancer Vaccines that Induce Antibodies" Expert Rev. Vaccines 1(2):193-206 (2002).

Sadanaga et al. "Dendritic Cell Vaccination with MAGE Peptide is a Novel Therapeutic Approach for Gastrointestinal Carcinomas" Clin Cancer Research 7:2277-2284 (2001).

Schlesinger and Dubensky Jr. "Alphavirus Vectors for Gene Expression and Vaccines" Current Opinion in Biotechnology 10(5):434-439 (1999).

Slepushkin et al. "Large Scale Purification of a Lentiviral Vector by Size Exclusion Chromatography or Mustang Q Ion Exchange Capsule" Bioprocessing Journal pp. 89-94 (Sep.-Oct. 2003).

Technical Bulletin No. 166: RiboMAX Large Scale RNA Production Systems—SP6 and T7; Promega Corporation p. 1-11; Revised Sep. 2001; http://www.promega.com/tbs/tb166.pdf on Nov. 4, 2004.

Temperton "DNA Vaccines Against Cytomegalovirus: Current Progress" International Journal of Antimicrobial Agents 19:169-172 (2002).

Waite et al. "Inhibition of Sindbis Virus Production by Media of Low Ionic Strength: Intracellular Events and Requirements for Reversal" Journal of Virology 5:60-71 (1970).

Walter et al. "Reconstitution of Cellular Immunity Against Cytomegalovirus in Recipients of Allogeneic Bone Marrow by Transfer of T-Cell Clones from the Donor" The New England Journal of Medicine 333(16):1038-1044 (1995).

Ward et al. "Immunotherapeutic Potential of Whole Tumor Cells" Cancer Immunol. Immunother. 51:351-357 (2002).

Williamson et al. "Designing HIV-1 Subtype C Vaccines for South Africa" South African Journal of Science 96:318-324 (2000).

Wilson et al. "Vaccine Potential of Ebola Virus VP24, VP30, VP35 and VP40 Proteins" Virology 286:384-390 (2001).

Yamanaka et al. "Enhancement of Antitumor Immune Response in Glioma Models in Mice by Genetically Modified Dendritic Cells Pulsed with Semliki Forest Virus-Mediated Complementary DNA" J. Neurosurgery 94:474-481 (2001).

Yamanaka et al. "Marked Enhancement of Antitumor Immune Responses in Mouse Brain Tumor Models by Genetically Modified Dendritic Cells Producing Semliki Forest Virus-Mediated Interleukin-12" J. Neurosurgery 97:611-618 (2002).

Ying et al. "Cancer Therapy Using a Self-Replicating RNA Vaccine" Nature Medicine 5(7):823-827 (1999).

Barouch et al. "Augmentation of Immune Responses of HIV-1 and Simian Immunodeficiency Virus DNA Vaccines by IL-2/Ig Plasmid Administration in Rhesus Monkeys" PNAS 97(8): 4192-4197 (2000).

Berglund et al. "Semliki Forest Virus Expression System: Production of Conditionally Infectious Recombinant Particles" Bio/Technology 11:916-920 (1993).

Betts et al. "Cross-Clade Human Immunodeficiency Virus (HIV)-Specific Cytotoxic T-Lymphocyte Responses in HIV-Infected Zambians" J. Virol. 71(11):8908-8911 (1997).

Bredenbeek et al. "Sindbis Virus Expression Vectors: Packaging of RNA Replicons by Using Defective Helper RNAs" Journal of Virology 67:6439-6446 (1993).

Caley et al. "Humoral, Mucosal, and Cellular Immunity in Response to a Human Immunodeficiency Virus Type 1 Immunogen Expressed by a Venezuelan Equine Encephalitis Virus Vaccine Vector" J. Virol. 71(4):3031-3038 (1997).

Caley et al. "Venezuelan Equine Encephalitis Virus Vectors Expressing HIV-1 Proteins: Vector Design Strategies for Improved Vaccine Efficacy" Vaccine 17:3124-3135 (1999).

Chappell et al. "A 9-nt Segment of a Cellular mRNA can Function as an Internal Ribosome Site (IRES) and when Present in Linked Multiple Copies Greatly Enhances IRES Activity" PNAS 97(4): 1536-1541 (2000).

Corsini et al. "Efficiency of Transduction by Recombinant Sindbis Replicon Virus Varies Among Cell Lines, Including Mosquito Cells and Rat Sensory Neurons" BioTechniques 21(3):492-497 (1996).

Cutler et al. "Mutants of the Membrane-binding Region of Semliki Forest Virus E2 Protein. I. Cell Surface Transport and Fusogenic Activity" The Journal of Cell Biology 102: 889-901 (1986).

Davis et al. "A Genetically Engineered Live Virus Vaccine for Venezuelan Equine Encephalitis" J. Cell Biochemistry Supplement O No. 17 Part D, Abstract N404 (1993) (Abstract).

Davis et al. "A molecular genetic approach to the study of Venezuelan equine encephalitis virus pathogenesis" Archives of Virology 9:99-109 (1994).

Davis et al. "A Viral Vaccine Vector that Expresses Foreign Genes in Lymph Nodes and Protects against Mucosal Challenge" Journal of Virology 70: 3781-3787 (1996).

Davis et al. "Attenuated Mutants of Venezuelan Equine Encephalitis Virus Containing Lethal Mutations in the PE2 Cleavage Signal Combined with a Second-Site Suppressor Mutation in E1" Virology 212:102-110 (1995).

Davis et al. "Attenuating Mutations in the E2 Glycoprotein Gene of Venezuelan Equine Encephalitis Virus: Construction of Single and Multiple Mutants in a Full-Length cDNA Clone" Virology 183:20-31 (1991).

Davis et al. "Immunization against Influenza with Attenuated Venezuelan Equine Encephalitis Virus Vectors" Options for the Control of Influenza III. L. E. Brown and A. W. Hampson, eds. Elsevier, Amsterdam:803-809 (1996).

Davis et al. "In Vitro Synthesis of Infectious Venezuelan Equine Encephalitis Virus RNA from a cDNA Clone: Analysis of a Viable Deletion Mutant and Mutations Affecting Virulence" Vaccines 90:109-113 (1990).

Davis et al. "Vaccination of Macaques against Pathogenic Simian Immunodeficiency Virus with Venezuelan Equine Encephalitis Virus Replicon Particles" J. Virol. 74(1):371-378 (2001).

Dubensky et al. "Sindbis Virus DNA-Based Expression Vectors: Utility for in vitro and in vivo Gene Transfer" Journal of Virology 70:508-519 (1996).

Dubuisson et al. "Sindbis Virus Attachment: Isolation and Characterization of Mutants with Impaired Binding to Vertebrate Cells" Journal of Virology 67: 3363-3374 (1993).

Favre et al. "Semliki Forest Virus Capsid Protein Expressed by a Baculovirus Recombinant" Archives of Virology 132:307-319 (1993).

Feyzi et al. "Structural Requirement of Heparan Sulfate for Interaction with Herpes Simplex Virus Type I Virions and Isolated Glycoprotein C" The Journal of Biological Chemistry 272(40):24850-24857 (1997).

Frolov et al. "Alphavirus-Based Expression Vectors: Strategies and Applications" Proc. Natl. Acad. Sci. USA 93:11371-11377 (1996).

Garoff et al. "Expression of Semliki Forest Virus Proteins from Cloned Complementary DNA. II. The Membrane-spanning Glycoprotein E2 is Transported to the Cell Surface without its Normal Cytoplasmic Domain" The Journal of Cell Biology 97: 652-658 (1983).

Geigenmuller-Gnirke et al. "Complementation Between Sindbis Viral RNAs Produces Infectious Particles with a Bipartite Genome" Proceedings of the National Academy of Sciences 88:3253-3257 (1991).

Gingras et al. "Activation of the Translational Suppressor 4E-BP1 Following Infection with Encephalomyocarditis Virus and Poliovirus" Proc. Natl. Acad. Sci. USA 93:5578-5583 (1996).

Gradi et al. "Proteolysis of Human Eukaryotic Translation Initiation Factor eIF4GII, but Not eIF4GI, Coincides with the Shutoff of Host Protein Synthesis after Poliovirus Infection" Proc. Natl. Acad. Sci. USA 95:11089-11094 (1998).

Grieder et al. "Specific Restrictions in the Progression of Venezuelan Equine Encephalitis Virus-Induced Disease Resulting from Single Amino Acid Changes in the Glycoproteins" Virology 206:994-1006 (1995).

Heidner et al. "Lethality of PE2 Incorporation into Sindbis Virus can be Suppressed by Second-Site Mutations in E3 and E2" Journal of Virology 68: 2683-2692 (1994).

Heise et al. "An Attenuating Mutation in nsP1 of the Sindbis-Group Virus S.A.AR86 Accelerates Nonstructural Protein Processing and Up-Regulates Viral 26S RNA Synthesis" *Journal of Virology* 77(2):1149-1156 (2003).
Herweijer et al. "Self-Amplifying Vectors for Gene Delivery" *Advanced Drug Delivery Reviews* 27:5-16 (1997).
Hevey et al. "Marburg Virus Vaccines: Comparing Classical and New Approaches" *Vaccine* 20:586-593 (2002).
Hirsch et al. "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara" *J. Virol.* 70(6):3741-3752 (1996).
Hodgson et al. "Expression of Venezuelan Equine Encephalitis Virus Proteins by Recombinant Baculoviruses" *The American Journal of Tropical Medicine and Hygiene*. 49:195-196 (1993) (Supplement).
Holcik and Korneluk "Functional Characterization of the X-Linked Inhibitor of Apoptosis (XIAP) Internal Ribosome Entry Site Element: Role of La Autoantigen in XIAP Translation" *Molecular and Cellular Biology* 20(13): 4648-4657 (2000).
Holcik et al. "A New Internal-Ribosome-Entry-Site Motif Potentiates XIAP-Mediated Cytoprotection" *Nature Cell Biology* 1:190-192 (1999).
Holcik et al. "The Internal Ribosome Entry-Site-Mediated Translation of Antiapoptotic Protein XIAP is Modulated by the Heterogeneous Nuclear Ribonucleoproteins C1 and C2" *Molecular and Cellular Biology* 23(1):280-288 (2003).
International Search Report of International Application Serial No. PCT/US02/28610 filed Sep. 6, 2002.
Jalanko "Expression of Semliki Forest Virus Capsid Protein from SV40 Recombinant Virus" *FEBS Letters* 186:59-64 (1985).
Jang and Wimmer "Cap-Independent Translation of Encephalomyocarditis Virus RNA: Structural Elements of the Internal Ribosomal Entry Site and Involvement of a Cellular 57-kD RNA-Binding Protein" *Genes & Development* 4:1560-1572 (1990).
Joachims et al. "Cleavage of Poly(A)-Binding Protein by Enterovirus Proteases Concurrent with Inhibition of Translation In Vitro" *Journal of Virology* 73(1):718-727 (1999).
Johnston and Peters, "Alphaviruses" *Fields Virology*, 3rd ed., Lippincott-Raven Publishers, Philadelphia, Chapt, 28:843-898 (1996).
Johnston and Smith "Selection for Accelerated Penetration in Cell Culture Coselects for Attenuated Mutants of Venezuelan Equine Encephalitis Virus" *Virology* 162:437-443 (1988).
Kinney et al. "Attenuation of Venezuelan Equine Encephalitis Virus Strain TC-83 Is Encoded by the 5'-Noncoding Region and the E2 Envelope Glycoprotein" *Journal of Virology* 67:1269-1277 (1993).
Kinney et al. "The Full-Length Nucleotide Sequences of the Virulent Trinidad Donkey Strain of Venezuelan Equine Encephalitis Virus and its Attenuated Vaccine Derivative, Strain TC-83" *Virology* 170:19-30 (1989).
Klimstra et al. "Adaptation of Sindbis Virus to BHK Cells Selects for Use of Heparan Sulfate as an Attachment Receptor" *Journal of Virology* 72(9):7357-7366 (1998).
Kondor-Koch et al. "Expression of Semliki Forest Virus Proteins from Cloned Complementary DNA. I. The Fusion Activity of the Spike Glycoprotein" *J. Cell Biology* 97(3):644-651 (1983).
Lee et al. "Efficient Long-Term Coexpression of a Hammerhead Ribozyme Targeted to the U5 Region of HIV-I LTR by Linkage to the Multidrug-Resistance Gene" *Antisense & Nucleic Acid Drug Development* 7:511-522 (1997).
Lemm et al. "Polypeptide Requirements for Assembly of Functional Sindbis Virus Replication Complexes: a Model for the Temporal Regulation of Minus- and Plus-Strand RNA Synthesis" *The EMBO Journal* 13:2925-2934 (1994).
Leone et al. "In Vitro Synthesis of the Gene Coding for the Glycoprotein E1 of Sindbis Virus" *Microbiologica* 8(2):123-130 (1985) (Abstract).
Li et al. "Production of Infectious Recombinant Moloney Murine Leukemia Virus Particles in BHK Cells Using Semliki Forest Virus-Derived RNA Expression Vectors" *Proc. Natl. Acad. Sci. USA* 93: 11658-11663 (Oct. 1996).
Liljeström "Alphavirus Expression Systems" *Current Opinion in Biotechnology* 5:495-500 (1994).
Liljestrom et al. "A New Generation of Animal Cell Expression Vectors Based on the Semliki Forest Virus Replicon" *Bio/Technology* 9:1356-1361 (1991).
Lobigs et al. "Fusion Function of the Semliki Forest Virus Spike is Activated by Proteolytic Cleavage of the Envelope Glycoprotein Precursor p62" *Journal of Virology* 64: 1233-1240 (1990).
Lundström et al. "Secretion of Semliki Forest Virus Membrane Glycoprotein E1 from *Bacillus subtilis*" *Virus Research* 2:69-83 (1985).
Martinez-Salas et al. "Functional Interactions in Internal Translation Initiation Directed by Viral and Cellular IRES Elements" *Journal of General Virology* 82:973-984 (2001).
McKnight et al. "Deduced Consensus Sequence of Sindbis Virus Strain AR339: Mutations Contained in Laboratory Strains Which Affect Cell Culture and In Vivo Phenotypes" *Journal of Virology* 70(3): 1981-1989 (1996).
Melancon et al. "Processing of the Semliki Forest Virus Structural Polyprotein: Role of the Capsid Protease" *Journal of Virology* 61:1301-1309 (1987).
Melancon et al. "Reinitiation of Translocation in the Semliki Forest Virus Structural Polyprotein: Identification of the Signal for the E1 Glycoprotein" *The EMBO Journal* 5:1551-1560 (1986).
Morgenstern et al. "Advanced Mammalian Gene Transfer: High Titre Retroviral Vectors with Multiple Drug Selection Markers and a Complementary Helper-Free Packaging Cell Line" *Nucleic Acids Research* 18:3587-3596 (1990).
Oker-Blom et al. "Expression of Sindbis Virus 26S cDNA in *Spodoptera frugiperda* (Sf9) Cells, Using a Baculovirus Expression Vector" *J. Virology* 63:1256-1264 (1989).
Orkin et al. "Report and Recommendations of the Panel to Assess the NIH Investment in Research on Gene Therapy" (1995).
Paredes et al. "Three-dimensional Structure of a Membrane-Containing Virus" *Proc. Natl. Acad. Sci. USA* 90:9095-9099 (1993).
Polo and Johnston "Attenuating Mutations in Glycoproteins E1 and E2 of Sindbis Virus Produce a Highly Attenuated Strain When Combined in Vitro" *Journal of Virology* 64:4438-4444 (1990).
Presley et al. "Proteolytic Processing of the Sindbis Virus Membrane Protein Precursor PE2 is Nonessential for Growth in Vertebrate Cells but is Required for Efficient Growth in Invertebrate Cells" *Journal of Virology* 65:1905-1909 (1991).
Pushko et al. "Replicon-Helper Systems from Attenuated Venezuelan Equine Encephalitis Virus: Expression of Heterologous Genes in Vitro and Immunization Against Heterologous Pathogens in Vivo" *Virology* 239:389-401 (1997).
Rice et al. "Expression of Sindbis Virus Structural Proteins via Recombinant Vaccinia Virus: Synthesis, Processing, and Incorporation into Mature Sindbis Virions" *J. Virology* 56:227-239 (1985).
Riedel "Different Membrane Anchors Allow the Semliki Forest Virus Spike Subunit E2 to Reach the Cell Surface" *Journal of Virology* 54:224-228 (1985).
Roberts and Belsham "Complementation of Defective Picornavirus Internal Ribosome Entry Site (IRES) Elements by the Coexpression of Fragments of the IRES" *Virology* 227:53-62 (1997).
Russell et al. "Sindbis Virus Mutations Which Coordinately Affect Glycoprotein Processing, Penetration, and Virulence in Mice" *Journal of Virology* 63:1619-1629 (1989).
Salminen et al. "Membrane Fusion Process of Semliki Forest Virus II: Cleavage-dependent Reorganization of the Spike Protein Complex Controls Virus Entry" *The Journal of Cell Biology* 116: 349-357 (1992).
Schlesinger "Alphaviruses—Vectors for the Expression of Heterologous Genes" *TiBTech* 11:18-22 (1993).
Schlesinger and Schlesinger "*Togaviridae*: The Viruses and Their Replication" *Fields Virology* 3rd edition. (Fields et al., eds.) Lipincott-Raven Publishers, Philadelphia (1996) pp. 825-841.
Schoepp and Johnston "Directed Mutagenesis of a Sindbis Virus Pathogenesis Site" *Virology* 193:149-159 (1993).
Simpson et al. "Complete Nucleotide Sequence and Full-Length cDNA Clone of S.A.AR86, a South African Alphavirus Related to Sindbis" *Virology* 222:464-469 (1996).

Sjöberg et al. "A Significantly Improved Semliki Forest Virus Expression System Based on Translation Enhancer Segments from the Viral Capsid Gene" *Bio/Technology* 12:1127-1131 (1994).

Smerdou and Liljestrom "Two-Helper RNA System for Production of Recombinant Semliki Forest Virus Particle" *Journal of Virology* 73(2):1092-1098 (1999).

Strauss and Strauss "Alphavirus Proteinases" *Seminars In Virology* 1:347-356 (1990).

Strauss and Strauss "The Alphaviruses: Gene Expression, Replication, and Evolution" *Microbiological Reviews* 58:491-562 (1994).

Suomalainen et al. "Spike Protein-Nucleocapsid Interactions Drive the Budding of Alphaviruses" *Journal of Virology* 66(8):4737-4747 (1992).

Sykes and Johnston "Genetic Live Vaccines Mimic the Antigenicity but Not Pathogenicity of Live Viruses" *DNA and Cell Biology* 18(7):521-531 (1999).

Thompson and Sarnow "Enterovirus 71 Contains a Type I IRES Element that Functions When Eukaryotic Initiation Factor eIF4G is Cleaved" *Virology* 315:259-266 (2003).

Ubol et al. "Neurovirulent Strains of Alphavirus Induce Apoptosis in bcl-2-Expressing Cells: Role of a Single Amino Acid Change in the E2 Glycoprotein" *Proc. National Academy Sciences* 91: 5202-5206 (1994).

Van der Velden et al. "Defective Point Mutants of the Encephalomyocarditis Virus Internal Ribosome Entry Site can be Complemented in Trans" *Virology* 214:82-90 (1995).

Verma et al. "Gene Therapy—Promises, Problems and Prospects" *Nature* 389:239-242 (1997).

Weiss and Schlesinger "Recombination between Sindbis Virus RNAs" *Journal of Virology* 65: 4017-4025 (1991).

Wen et al. "Expression of Genes Encoding Vesicular Stomatitis and Sindbis Virus Glycoproteins in Yeast Leads to Formation of Disulfide-Linked Oligomers" *Virology* 153:150-154 (1986).

Williamson et al. "Characterization and Selection of HIV-1 Subtype C Isolates for Use in Vaccine Development" *AIDS Research and Human Retroviruses* 19(2):133-144 (2003).

Xiong et al. "Sindbis Virus: An Efficient, Broad Host Range Vector for Gene Expression in Animal Cells" *Science* 243:1188-1191 (1989).

Yang and Sarnow "Location of the Internal Ribosome Entry Site in the 5' Non-Coding Region of the Immunoglobulin Heavy-Chain Binding Protein (BiP) mRNA: Evidence for Specific RNA-Protein Interactions" *Nucleic Acids Research* 25(14):2800-2807 (1997).

Zhao et al. "Role of Cell Surface Spikes in Alphavirus Budding" *Journal of Virology* 66:7089-7095 (1992).

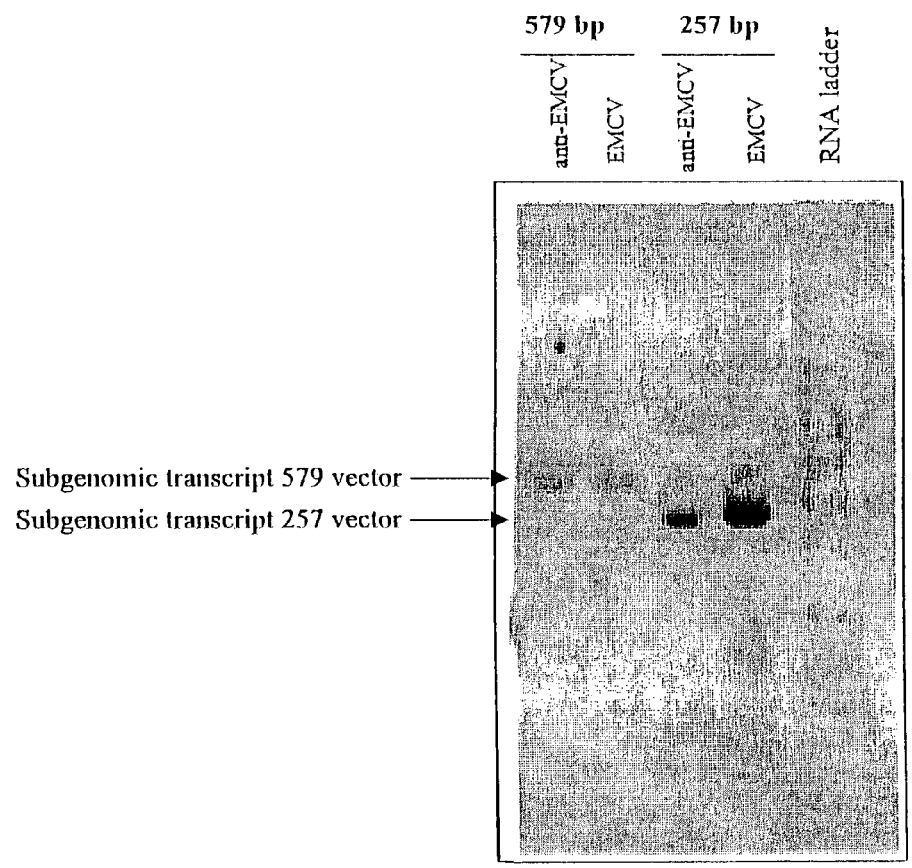
Figure 1. Northern analysis of spacer-IRES replicon subgenomic RNAs

SEQUENCE LISTING

<160> NUMBER OF SEQ ID NOS: 44

<210> SEQ ID NO 1

```
<211> LENGTH: 18
<212> TYPE: PRT
<213> ORGANISM: Artificial
<220> FEATURE:
<223> OTHER INFORMATION: Alphavirus attenuating amino acid insertion
      sequence

<400> SEQUENCE: 1

Ile Thr Ser Met Asp Ser Trp Ser Ser Gly Pro Ser Ser Leu Glu Ile
1               5                   10                  15

Val Asp

<210> SEQ ID NO 2
<211> LENGTH: 357
<212> TYPE: DNA
<213> ORGANISM: Artificial
<220> FEATURE:
<223> OTHER INFORMATION: Spacer sequence generated by AluI digest of
      pCDNA

<400> SEQUENCE: 2
ctgaatgaag ccataccaaa cgacgagcgt gacaccacga tgcctgtagc aatggcaaca      60
acgttgcgca aactattaac tggcgaacta cttactctag ctaccaactc ttttttccgaa    120 ggtaactggc ttcagcagag cgcagatacc aaatactgtt cttctagtgt agccgtagtt    180
aggccaccac ttcaagaact ctgtagcacc gcctacatac ctcgctctgc taatcctgtt    240
accagtggct gctgccagtg gcgataagtc gtgtcttacc gggttggact caagacgata    300
gttaccggat aaggcgcagc ggtcgggctg aacgggggt tcgtgcacac agcccag       357

<210> SEQ ID NO 3
<211> LENGTH: 342
<212> TYPE: DNA
<213> ORGANISM: Artificial
<220> FEATURE:
<223> OTHER INFORMATION: Spacer sequence generated by AluI digest of
      pCDNA

<400> SEQUENCE: 3
ctattccaga agtagtgagg aggcttttt ggaggcctag gcttttgcaa aaagcttgta      60
tatccatttt cggatctgat caagagacag gatgaggatc gtttcgcatg attgaacaag    120
atggattgca cgcaggttct ccggccgctt gggtggagag gctattcggc tatgactggg    180
cacaacagac aatcggctgc tctgatgccg ccgtgttccg gctgtcagcg caggggcgcc    240
cggttctttt tgtcaagacc gacctgtccg gtgccctgaa tgaactgcag gacgaggcag    300
cgcggctatc gtggctggcc acgacgggcg ttccttgcgc ag                        342

<210> SEQ ID NO 4
<211> LENGTH: 257
<212> TYPE: DNA
<213> ORGANISM: Artificial
<220> FEATURE:
<223> OTHER INFORMATION: Spacer sequence generated by AluI digest of
      pCDNA

<400> SEQUENCE: 4 ctcattttt aaccaatagg ccgaaatcgg caaaatccct tataaatcaa agaatagac       60 cgagatagggg ttgagtgttg ttccagtttg gaacaagagt ccactattaa agaacgtgga   120
ctccaacgtc aaagggcgaa aaaccgtcta tcagggcgat ggcccactac gtgaaccatc    180
accctaatca gttttttgg ggtcgaggtg ccgtaaagca ctaaatcgga accctaaagg     240
```

<210> SEQ ID NO 5
<211> LENGTH: 383
<212> TYPE: DNA
<213> ORGANISM: Artificial
<220> FEATURE:
<223> OTHER INFORMATION: Spacer sequence generated by AluI digest of pCDNA

<400> SEQUENCE: 5

```
ctgcgcaagg aacgcccgtc gtggccagcc acgatagccg cgctgcctcg tcctgcagtt      60
cattcagggc accggacagg tcggtcttga caaaaagaac cgggcgcccc tgcgctgaca     120
gccggaacac ggcggcatca gagcagccga ttgtctgttg tgcccagtca tagccgaata     180
gcctctccac ccaagcggcc ggagaacctg cgtgcaatcc atcttgttca atcatgcgaa     240
acgatcctca tcctgtctct tgatcagatc cgaaaatgga tatacaagct cactcattag     300
gcaccccagg ctttacactt tatgcttccg gctcgtatgt tgtgtggaat tgtgagcgga     360
taacaatttc acacaggaaa cag                                             383
```

<210> SEQ ID NO 6
<211> LENGTH: 579
<212> TYPE: DNA
<213> ORGANISM: Artificial
<220> FEATURE:
<223> OTHER INFORMATION: Spacer sequence generated by AluI digest of pCDNA

<400> SEQUENCE: 6

```
ctgcaataaa caagttgggg tgggcgaaga actccagcat gagatccccg cgctggagga      60
tcatccagcc ggcgtccgg aaaacgattc cgaagcccaa cctttcatag aaggcggcgg      120
tggaatcgaa atctcgtgat ggcaggttgg gcgtcgcttg gtcggtcatt tcgaacccca     180
gagtcccgct cagaagaact cgtcaagaag gcgatagaag gcgatgcgct gcgaatcggg     240
agcggcgata ccgtaaagca cgaggaagcg gtcagcccat cgccgccaa gcttgtatat      300
ccatttttcgg atctgatcaa gagacaggat gaggatcgtt tcgcatgatt gaacaagatg     360
gattgcacgc aggttctccg gccgcttggg tggagaggct attcggctat gactgggcac     420
aacagacaat cggctgctct gatgccgccg tgttccggct gtcagcgcag gggcgcccgg     480
ttctttttgt caagaccgac ctgtccggtg ccctgaatga actgcaggac gaggcagcgc     540
ggctatcgtg gctggccacg acgggcgttc cttgcgcag                            579
```

<210> SEQ ID NO 7
<211> LENGTH: 749
<212> TYPE: DNA
<213> ORGANISM: Artificial
<220> FEATURE:
<223> OTHER INFORMATION: Spacer sequence generated by AluI digest of pCDNA

<400> SEQUENCE: 7

```
ctgcaataaa caagttgggg tgggcgaaga actccagcat gagatccccg cgctggagga      60
tcatccagcc ggcgtccgg aaaacgattc cgaagcccaa cctttcatag aaggcggcgg      120
tggaatcgaa atctcgtgat ggcaggttgg gcgtcgcttg gtcggtcatt tcgaacccca     180
gagtcccgct cagaagaact cgtcaagaag gcgatagaag gcgatgcgct gcgaatcggg     240
agcggcgata ccgtaaagca cgaggaagcg gtcagcccat cgccgccaa gctcttcagc      300
```

| | |
|---|---|
| aatatcacgg gtagccaacg ctatgtcctg atagcggtcc gccacaccca gccggccaca | 360 |
| gtcgatgaat ccagaaaagc ggccattttc caccatgata ttcggcaagc aggcatcgcc | 420 |
| atgggtcacg acgagatcct cgccgtcggg catgcgcgcc ttgagcctgg cgaacagttc | 480 |
| ggctggcgcg agcccctgat gctcttcgtc cagatcatcc tgatcgacaa gaccggcttc | 540 |
| catccgagta cgtgctcgct cgatgcgatg tttcgcttgg tggtcgaatg ggcaggtagc | 600 |
| cggatcaagc gtatgcagcc gccgcattgc atcagccatg atggatactt tctcggcagg | 660 |
| agcaaggtga gatgacagga gatcctgccc cggcacttcg cccaatagca gccagtccct | 720 |
| tcccgcttca gtgacaacgt cgagcacag | 749 |

<210> SEQ ID NO 8
<211> LENGTH: 30
<212> TYPE: DNA
<213> ORGANISM: Artificial
<220> FEATURE:
<223> OTHER INFORMATION: PCR primer

<400> SEQUENCE: 8
tggcgcgccg ctcggaattc cccctctccc          30

<210> SEQ ID NO 9
<211> LENGTH: 29
<212> TYPE: DNA
<213> ORGANISM: Artificial
<220> FEATURE:
<223> OTHER INFORMATION: PCR primer

<400> SEQUENCE: 9
aggcgcgcct tctatgtaag cagcttgcc           29

<210> SEQ ID NO 10
<211> LENGTH: 30
<212> TYPE: DNA
<213> ORGANISM: Artificial
<220> FEATURE:
<223> OTHER INFORMATION: PCR primer

<400> SEQUENCE: 10
gctggatcca tggagaaaaa aatcactgga          30

<210> SEQ ID NO 11
<211> LENGTH: 31
<212> TYPE: DNA
<213> ORGANISM: Artificial
<220> FEATURE:
<223> OTHER INFORMATION: PCR primer

<400> SEQUENCE: 11
cgatctagat tacgccccgc cctgccactc a        31

<210> SEQ ID NO 12
<211> LENGTH: 26
<212> TYPE: DNA
<213> ORGANISM: Artificial
<220> FEATURE:
<223> OTHER INFORMATION: PCR primer

<400> SEQUENCE: 12
cggaattcat tatcatcgtg tttttc              26

<210> SEQ ID NO 13
<211> LENGTH: 31

```
<212> TYPE: DNA
<213> ORGANISM: Artificial
<220> FEATURE:
<223> OTHER INFORMATION: PCR primer

<400> SEQUENCE: 13
cgggatcccc cctaacgtta ctggccgaag c                                    31

<210> SEQ ID NO 14
<211> LENGTH: 27
<212> TYPE: DNA
<213> ORGANISM: Artificial
<220> FEATURE:
<223> OTHER INFORMATION: PCR primer

<400> SEQUENCE: 14
aggcgcgcca ttatcatcgt gtttttc                                         27

<210> SEQ ID NO 15
<211> LENGTH: 29
<212> TYPE: DNA
<213> ORGANISM: Artificial
<220> FEATURE:
<223> OTHER INFORMATION: PCR primer

<400> SEQUENCE: 15
aggcgcgccc tagggtctct tcccctctc                                       29

<210> SEQ ID NO 16
<211> LENGTH: 42
<212> TYPE: DNA
<213> ORGANISM: Artificial
<220> FEATURE:
<223> OTHER INFORMATION: PCR primer

<400> SEQUENCE: 16
gcggcatgcc aatcgccgcg agttctatgt aagcagcttg cc                        42

<210> SEQ ID NO 17
<211> LENGTH: 26
<212> TYPE: DNA
<213> ORGANISM: Artificial
<220> FEATURE:
<223> OTHER INFORMATION: PCR primer

<400> SEQUENCE: 17
cgggatccat ggctgcgaga gcgtca                                          26

<210> SEQ ID NO 18
<211> LENGTH: 28
<212> TYPE: DNA
<213> ORGANISM: Artificial
<220> FEATURE:
<223> OTHER INFORMATION: PCR primer

<400> SEQUENCE: 18
cgggatcctt attgagacaa ggggtcgc                                        28

<210> SEQ ID NO 19
<211> LENGTH: 24
<212> TYPE: DNA
<213> ORGANISM: Artificial
<220> FEATURE:
<223> OTHER INFORMATION: PCR primer

<400> SEQUENCE: 19
```

-continued

```
ccctgctcgt gccagtgttg atgc                                           24
```

<210> SEQ ID NO 20
<211> LENGTH: 35
<212> TYPE: DNA
<213> ORGANISM: Artificial
<220> FEATURE:
<223> OTHER INFORMATION: PCR primer

<400> SEQUENCE: 20

```
acacgtgggg caaccctgat ttatgcctgt tgtcc                               35
```

<210> SEQ ID NO 21
<211> LENGTH: 30
<212> TYPE: DNA
<213> ORGANISM: Artificial
<220> FEATURE:
<223> OTHER INFORMATION: PCR primer

<400> SEQUENCE: 21

```
agttaactca aaagagaaaa acaaaaatgc                                     30
```

<210> SEQ ID NO 22
<211> LENGTH: 33
<212> TYPE: DNA
<213> ORGANISM: Artificial
<220> FEATURE:
<223> OTHER INFORMATION: PCR primer

<400> SEQUENCE: 22

```
agatatcttc tcttgaaaat aggacttgtc cac                                 33
```

<210> SEQ ID NO 23
<211> LENGTH: 25
<212> TYPE: DNA
<213> ORGANISM: Artificial
<220> FEATURE:
<223> OTHER INFORMATION: PCR primer

<400> SEQUENCE: 23

```
gttcccgttc cagccaatgt atccg                                          25
```

<210> SEQ ID NO 24
<211> LENGTH: 20
<212> TYPE: DNA
<213> ORGANISM: Artificial
<220> FEATURE:
<223> OTHER INFORMATION: PCR primer

<400> SEQUENCE: 24

```
gtcactagtg accaccatgt                                                20
```

<210> SEQ ID NO 25
<211> LENGTH: 20
<212> TYPE: DNA
<213> ORGANISM: Artificial
<220> FEATURE:
<223> OTHER INFORMATION: PCR primer

<400> SEQUENCE: 25

```
taagagccgc gagcgatcct                                                20
```

<210> SEQ ID NO 26
<211> LENGTH: 1014
<212> TYPE: DNA
<213> ORGANISM: Homo sapiens

<400> SEQUENCE: 26

```
acacgtgggg caaccctgat ttatgcctgt tgtcccagtg tgattattac tagtgtaatt      60
tttcactttg agaagtgtcc aggtttggag gataaattat ctttctaata attgataccc     120
ttctcataac ctaacgggtt ccttttagta ttttatctgg gttaaaatta ccagctgtaa     180
tttggcagct ctaataagac tgcagcaata cttatcttcc atttgaacag attgttactt     240
gaccaaggga agttaatagc aaaagtaact gcagggcaca tgtatgtcat gggcaaaaaa     300
aaaaaagtaa cagcaattaa ggtttgcagg tacttagaat ttttcctgag ccaccctcta     360
gagggcagtg ttacatatat atctgtaatt atccagttac aacaaaaaaa gggctctcat     420
tcatgcatga aaatcagaaa tatttcatac tcttaaagaa cacattggaa ccaatattat     480
gattaaaaca tattttgcta agcaaagaga tattaaaaat taattcatta acattctgaa     540
catttttttaa cttgtaaaaa caactttgat gccttgaata tataatgatt cattataaca    600
attatgcata gattttaata atctgcatat tttatgcttt catgttttc ctaattaatg     660
atttgacatg gttaataatt ataatatatt ctgcatcaca gtttacatat ttatgtaaaa    720
taagcattta aaaattatta gttttattct gcctgcttaa atattacttt cctcaaaaag    780
agaaaacaaa aatgctagat tttacttttat gacttgaatg atgtggtaat gtcgaactct    840
agtatttaga attagaatgt ttcttagcgg tcgtgtagtt atttttatgt cataagtgga    900
taatttgtta gctcctataa caaaagtctg ttgcttgtgt ttcacatttt ggatttccta    960
atataatgtt ctcttttttag aaaaggtgga caagtcctat tttcaagaga agat        1014
```

<210> SEQ ID NO 27
<211> LENGTH: 26
<212> TYPE: DNA
<213> ORGANISM: Artificial
<220> FEATURE:
<223> OTHER INFORMATION: PCR primer

<400> SEQUENCE: 27

```
cgaattctta aaacagctgt gggttg                                           26
```

<210> SEQ ID NO 28
<211> LENGTH: 37
<212> TYPE: DNA
<213> ORGANISM: Artificial
<220> FEATURE:
<223> OTHER INFORMATION: PCR primer

<400> SEQUENCE: 28

```
cgggatccgg tcaactgtat tgagggttaa tataaag                               37
```

<210> SEQ ID NO 29
<211> LENGTH: 34
<212> TYPE: DNA
<213> ORGANISM: Artificial
<220> FEATURE:
<223> OTHER INFORMATION: PCR primer

<400> SEQUENCE: 29

```
cgggatcctt aaaacagctg tgggttgttc ccac                                  34
```

<210> SEQ ID NO 30
<211> LENGTH: 36
<212> TYPE: DNA
<213> ORGANISM: Artificial
<220> FEATURE:

<223> OTHER INFORMATION: PCR primer

<400> SEQUENCE: 30
ggaattcggt caactgtatt gagggttaat ataaag                36

<210> SEQ ID NO 31
<211> LENGTH: 24
<212> TYPE: DNA
<213> ORGANISM: Artificial
<220> FEATURE:
<223> OTHER INFORMATION: PCR primer

<400> SEQUENCE: 31 gagaaaaaa atcactggat atac                24

<210> SEQ ID NO 32
<211> LENGTH: 27
<212> TYPE: DNA
<213> ORGANISM: Artificial
<220> FEATURE:
<223> OTHER INFORMATION: PCR primer

<400> SEQUENCE: 32
ggggatcctt acgccccgcc ctgccac                27

<210> SEQ ID NO 33
<211> LENGTH: 35
<212> TYPE: DNA
<213> ORGANISM: Artificial
<220> FEATURE:
<223> OTHER INFORMATION: PCR primer

<400> SEQUENCE: 33
cgacatagtc tagaccgcca agatgagagt gatgg                35

<210> SEQ ID NO 34
<211> LENGTH: 35
<212> TYPE: DNA
<213> ORGANISM: Artificial
<220> FEATURE:
<223> OTHER INFORMATION: PCR primer

<400> SEQUENCE: 34
gatctctaga ttattgcaaa gctgcttcaa agccc                35

<210> SEQ ID NO 35
<211> LENGTH: 28
<212> TYPE: DNA
<213> ORGANISM: Artificial
<220> FEATURE:
<223> OTHER INFORMATION: PCR primer

<400> SEQUENCE: 35
ccatcgatct attccagaag tagtgagg                28

<210> SEQ ID NO 36
<211> LENGTH: 20
<212> TYPE: DNA
<213> ORGANISM: Artificial
<220> FEATURE:
<223> OTHER INFORMATION: PCR primer

<400> SEQUENCE: 36
caatcgccgc gagttctatg                20

<210> SEQ ID NO 37
<211> LENGTH: 25
<212> TYPE: DNA
<213> ORGANISM: Artificial
<220> FEATURE:
<223> OTHER INFORMATION: PCR primer

<400> SEQUENCE: 37
gttcccgttc cagccaatgt atccg                                           25

<210> SEQ ID NO 38
<211> LENGTH: 20
<212> TYPE: DNA
<213> ORGANISM: Artificial
<220> FEATURE:
<223> OTHER INFORMATION: PCR primer

<400> SEQUENCE: 38
taagagccgc gagcgatcct                                                 20

<210> SEQ ID NO 39
<211> LENGTH: 49
<212> TYPE: DNA
<213> ORGANISM: Artificial
<220> FEATURE:
<223> OTHER INFORMATION: PCR primer

<400> SEQUENCE: 39
ccgcgagttc tatgtaagcg gcgcgccaat tgttacagac acatggtgg                 49

<210> SEQ ID NO 40
<211> LENGTH: 49
<212> TYPE: DNA
<213> ORGANISM: Artificial
<220> FEATURE:
<223> OTHER INFORMATION: PCR primer

<400> SEQUENCE: 40
ccaccatgtg tctgtaacaa ttggcgcgcc gcttacatag aactcgcgg                 49

<210> SEQ ID NO 41
<211> LENGTH: 24
<212> TYPE: DNA
<213> ORGANISM: Artificial
<220> FEATURE:
<223> OTHER INFORMATION: PCR primer

<400> SEQUENCE: 41 gctcttttg cgaagacaca taat                                             24

<210> SEQ ID NO 42
<211> LENGTH: 36
<212> TYPE: DNA
<213> ORGANISM: Artificial
<220> FEATURE:
<223> OTHER INFORMATION: PCR primer

<400> SEQUENCE: 42
ttggcgcgcc ttcttcggtt tcttagcgga tggccc                               36

<210> SEQ ID NO 43
<211> LENGTH: 31
<212> TYPE: DNA
<213> ORGANISM: Artificial
<220> FEATURE:
<223> OTHER INFORMATION: PCR primer

```
<400> SEQUENCE: 43
ttggcgcgcc cttccaacat gattgggaac g                                 31

<210> SEQ ID NO 44
<211> LENGTH: 37
<212> TYPE: DNA
<213> ORGANISM: Artificial
<220> FEATURE:
<223> OTHER INFORMATION: PCR primer

<400> SEQUENCE: 44
ttggcgcgcc tgtaatagcc ttggggtttc tcatggg                           37
```

ALPHAVIRUS REPLICONS AND HELPER CONSTRUCTS

RELATED APPLICATIONS

The present application claims the benefit, under 35 U.S.C. § 119(e), of U.S. provisional application Ser. No. 60/456,196, filed Mar. 20, 2003, the entire contents of which are incorporated by reference herein in their entirety.

FIELD OF THE INVENTION

The present invention relates to improved constructs for and methods of making recombinant alphavirus particles.

BACKGROUND OF THE INVENTION

In eukaryotes, two distinct mechanisms have evolved in cells to initiate translation. In one of them, the methyl-7-guanosine (5')pppN structure present at the 5' end of the mRNA (the "cap") is recognized by the initiation factor eIF4F, which is composed of eIF4E, eIF4G and eIF4A. The formation of this "pre-initiation complex" requires, among other factors, the concerted action of initiation factor eIF2, responsible for binding to the initiator tRNA-Met$_i$, and eIF3, which interacts with the 40S ribosomal subunit (Hershey & Menick. *Translational Control of Gene Expression*, pp. 33-88, Cold Spring Harbor Laboratory Press, NY 2000).

In the alternative mechanism, translation initiation occurs internally on the transcript and is mediated by an internal ribosome entry sequence (IRES) element that recruits the translational machinery to an internal initiation codon in the mRNA with the help of trans-acting factors (Jackson. *Translational Control of Gene Expression*, pp. 127-184, Cold Spring Harbor Laboratory Press, NY 2000). IRES elements have been found in numerous transcripts from viruses that infect vertebrate, invertebrate, or plant cells, as well as in transcripts from vertebrate and invertebrate genes.

During many viral infections, as well as in other cellular stress conditions, changes in the phosphorylation state of eIF2, which lower the levels of the ternary complex eIF2-GTP-tRNA-Met$_i$, result in overall inhibition of protein synthesis. Conversely, specific shut-off of cap-dependent initiation depends upon modification of eIF4F functionality (Thompson & Sarnow. *Currentt Opinion in Microbiology* 3: 366-370 (2000)).

IRES elements bypass cap-dependent translation inhibition; thus the translation directed by an IRES element is termed "cap-independent." IRES-driven translation initiation prevails during many viral infections, such as, for example, picornaviral infection (Macejak & Sarnow. *Nature* 353: 90-94 (1991)). Under these circumstances, cap-dependent initiation is inhibited or severely compromised due to the presence of small amounts of functional eIF4F. This is caused by cleavage or loss of solubility of eIF4G (Gradi et al. *Proceedings of the National Academy of Sciences*, USA 95: 11089-11094 (1998)); 4E-BP dephosphorylation (Gingras et al. *Proceedings of the National Academy of Sciences*, USA 93: 5578-5583 (1996)) or poly(A)-binding protein (PABP) cleavage (Joachims et al. *Journal of Virology* 73: 718-727 (1999)).

Alphavirus vectors that express a nucleic acid of interest (NOI) at varying levels have been described. All of these examples describe modification of the alphavirus non-structural protein genes or of the 26S (subgenomic) promoter to regulate vector replication or transcription from the subgenomic promoter. Examples include mutations in the non-structural protein genes that increase or decrease subgenomic RNA transcription or alter genomic RNA replication, resulting in modified NOI expression. Control of protein expression from an alphavirus vector, at the level of translation of the subgenomic mRNA, has not been described previously.

The present invention provides alphavirus replicon and helper vectors engineered to control the expression of one or more heterologous nucleic acid sequences at the level of protein translation via a cap-independent mechanism under the direction of an IRES element.

SUMMARY OF THE INVENTION

In one embodiment, the present invention provides a recombinant replicon nucleic acid comprising: a first nucleic acid sequence encoding a 5' alphavirus replication recognition sequence, at least one second nucleic acid sequence encoding an alphavirus nonstructural protein, at least one alphavirus subgenomic promoter, at least one IRES element, at least one heterologous nucleic acid, and a third nucleic acid encoding a 3' alphavilus replication recognition sequence, and an alphavirus packaging signal which allows the replicon to be packaged into particles.

In another embodiment, the present invention provides a recombinant helper nucleic acid comprising: a first nucleic acid sequence encoding a 5' alphavirus replication recognition sequence, an alphavirus subgenomic promoter, an IRES element, a nucleic acid encoding one or more than one alphavirus structural protein, and a third nucleic acid encoding a 3' alphavirus replication recognition sequence.

Also provided herein is an alphavirus particle comprising an alphavirus replicon RNA comprising the recombinant replicon nucleic acid of this invention. In a further embodiment, provided herein is a population of infectious, defective, alphavirus particles, wherein each particle contains an alphavirus replicon RNA comprising a recombinant replicon nucleic acid of this invention. In some embodiments, the invention provides a population of infectious, defective alphavirus particles wherein each particle contains an alphavirus replicon RNA comprising a recombinant replicon nucleic acid of this invention, and the population has no detectable replication-competent virus, as measured by passage on cell culture. In specific embodiments, the particles of this invention can contain one or more attenuating mutations.

In addition, pharmaceutical compositions are included, which comprise the particles and populations of this invention in a pharmaceutically acceptable carrier.

In other embodiments, the present invention provides a method of making infectious, defective alphavirus particles, comprising: (a) introducing into a population of cells (i) a recombinant replicon nucleic acid of this invention; and (ii) one or more helper nucleic acid(s) encoding alphavirus structural proteins; wherein all of the alphavirus structural proteins are provided in the cells; and (b) producing said alphavirus particles in the population of cells. The method of this invention can further comprise the step of collecting said alphavirus particles from the cells.

In some embodiments, the helper nucleic acid of this invention can also be a recombinant replicon nucleic acid of this invention. For example, a recombinant nucleic acid of this invention can comprise, as a heterologous nucleic acid and/or in addition to a heterologous nucleic acid, a nucleic acid sequence encoding one alphavirus structural protein or more than one alphavirus structural protein. In such embodiments, the recombinant replicon nucleic acid is considered to be a recombinant replicon helper nucleic acid, which can be present in a cell with other helper nucleic acids and/or other recombinant nucleic acids of this invention.

Thus, in a specific embodiment, the recombinant replicon nucleic acid of this invention further encodes an alphavirus structural protein or more than one alphavirus structural protein. This recombinant replicon nucleic acid can be introduced into a population of cells together with one or more helper nucleic acids, such that the recombinant replicon nucleic acid and the helper nucleic acid(s) produce all of the alphavirus structural proteins, and the recombinant replicon nucleic acid is packaged into particles in said cells.

Additionally provided are methods of eliciting an immune response in a subject, comprising administering to the subject an immunogenic amount of the nucleic acids, vectors, particles populations and/or compositions of this invention.

In further embodiments, the present invention provides a recombinant nucleic acid comprising: a promoter that directs transcription of a nucleic acid; an IRES element; and a nucleic acid comprising a coding sequence, wherein the IRES element is operably located such that translation of the coding sequence is via a cap-independent mechanism directed by the IRES element and not via a cap-dependent mechanism.

BRIEF DESCRIPTION OF THE DRAWINGS

FIG. 1 shows a northern blot of spacer-IRES replicon subgenomic RNAs.

DETAILED DESCRIPTION OF THE INVENTION

As used herein, "a," "an" and "the" can mean one or more than one, depending on the context in which it is used. As examples, "a cell" can mean one cell or multiple cells; and "a heterologous nucleic acid" can mean one heterologous nucleic acid or multiple heterologous nucleic acids.

The present invention is based on the surprising and unexpected discovery that transcription of a nucleic acid and translation of the nucleic acid can be uncoupled. Thus, in one embodiment, the present invention provides a recombinant nucleic acid comprising: a promoter that directs transcription; an IRES element; and a coding sequence, wherein the IRES element is operably located such that translation of the coding sequence is via a cap-independent mechanism directed by the IRES element and not via a cap-dependent mechanism. For the purposes of this invention, the term "transcription" includes the production of RNA from an alphavirus subgenomic promoter of a recombinant replicon nucleic acid, which can itself be an RNA molecule. That is, the subgenomic promoter on a recombinant replicon RNA molecule of this invention can direct the transcription of a messenger RNA encoding a heterologous NOI. Separately, the recombinant replicon nucleic acid can be "replicated," i.e., copied from the 5' replication recognition sequence through to the replication recognition sequence.

In other embodiments, the present invention provides a recombinant replicon nucleic acid comprising: a first nucleic acid sequence encoding a 5' alphavirus replication recognition sequence, at least one second nucleic acid sequence encoding an alphavirus nonstructural protein, at least one alphavirus subgenomic promoter, at least one IRES element, at least one heterologous nucleic acid, and a third nucleic acid encoding a 3' alphavirus replication recognition sequence. In certain embodiments, the recombinant replicon nucleic acid further comprises an alphavirus packaging signal so that the replicon can be packaged into particles. In further embodiments, the recombinant replicon nucleic acid can comprise a spacer nucleic acid sequence that can be located upstream of an IRES element.

It is understood that in various embodiments, the elements of the recombinant replicon nucleic acid of this invention can be present in the order listed herein and/or present in any order. Thus for example, in one embodiment, the present invention provides a recombinant replicon nucleic acid comprising, in the following order: a first nucleic acid sequence encoding a 5' alphavirus replication recognition sequence, at least one second nucleic acid sequence encoding an alphavirus nonstructural protein, at least one alphavirus subgenomic promoter, at least one IRES element, at least one heterologous nucleic acid, and a third nucleic acid encoding a 3' alphavirus replication recognition sequence As used herein, a "5' alphavirus replication recognition sequence" and "3' alphavirus replication recognition sequence" are 5' and 3' sequences (the 5' and 3' designations referring to their location in the alphavirus nucleic acid), which control replication of an alphavirus genome. In certain embodiments, either or both the 5' and 3' alphavirus replication recognition sequences can be truncated at either end, provided that their function in replication of an alphavirus genome remains intact.

Also as used herein, "at least one second nucleic acid sequence encoding an alphavirus nonstructural protein" includes a nucleic acid sequence that encodes at least one, and possibly more than one, alphavirus nonstructural protein. For example, a second nucleic acid sequence of this invention can be a contiguous nucleotide sequence encoding alphavirus nonstructural proteins nsp1, nsp2, nsp3 and nsp4, a contignuous nucleotide sequence encoding alphavirus nonstructural proteins nsp1, nsp2 and nsp3, a contiguous nucleic acid encoding alphavirus nonstructural proteins nsp2, nsp3 and nsp4, a contiguous nucleic acid encoding alphavirus nonstructural proteins nsp1 and nsp2, a contiguous nucleic acid encoding alphavirus nonstructural proteins nsp3 and nsp 4, a contiguous nucleic acid encoding alphavirus nonstructural proteins nsp2 and nsp3, a nucleic acid encoding alphavirus nonstructural protein nsp1, a nucleic acid encoding alphavirus nonstructural protein nsp2, a nucleic acid encoding alphavirus nonstructural protein nsp3, a nucleic acid encoding alphavirus nonstructural protein nsp4 and/or any combination and/or order thereof, such that the recombinant replicon nucleic acid comprises nucleotide sequences encoding nsp1, nsp2, nsp3 and nsp4 in total.

In particular embodiments, the recombinant replicon nucleic acid of this invention can comprise nucleic acid encoding one or more alphavirus nonstructural proteins in any combination and in any location relative to one another, such that the recombinant replicon nucleic acid comprises nucleotide sequences encoding nsp1, nsp2, nsp3 and nsp4 in total. For example, a recombinant replicon nucleic acid of this invention can comprise, in the following order: a first nucleic acid sequence encoding a 5' alphavirus replication recognition sequence, a second nucleic acid sequence encoding alphavirus nonstructural protein nsp1, nsp2 and nsp3, at least one alphavirus subgenomic promoter, at least one IRES element, at least one heterologous nucleic acid, another second nucleic acid sequence encoding alphavirus nonstructural protein nsp4, and a third nucleic acid encoding a 3' alphavirus replication recognition sequence As also used herein, an "alphavirus subgenomic promoter," "subgenomic promoter," or "26S promoter" is a promoter present in an alphavirus genome that directs transcription of a subgenomic message in a normal alphavirus replication process. The alphavirus subgenomic promoter can be truncated (e.g., to produce a minimal alphavirus subgenomic promoter) and/or modified such that its activity is reduced, maintained or increased, according to methods known in the art.

The recombinant nucleic acids of this invention can comprise an internal ribosome entry sequence (IRES) element, which directs translation of a nucleic acid into a protein via a cap-independent mechanism, as described herein and as is well known in the art. In particular in the recombinant replicon nucleic acids of the present invention, control of nucleic acid expression at the level of translation is accomplished by introducing an internal ribosome entry site (IRES) downstream of a alphavirus 26S subgenomic promoter and upstream of the coding sequence to be translated. The IRES element is positioned so that it directs translation of the mRNA, thereby minimizing, limiting or preventing initiation of translation of the mRNA from the methyl-7-guanosine (5')pppN structure present at the 5' end of the subgenomic mRNA (the "cap"). This "IRES-directed," cap-independent translation does not require or result in any significant modification of alphavirus non-structural protein genes that could alter replication and transcription.

Alphavirus vectors designed to control the expression level of a heterologous nucleic acid without modulating (e.g., disturbing, upsetting, perturbing, disrupting, increasing, enhancing, reducing, minimizing) genome replication or subgenomic transcription have several advantages over earlier vector designs. First, modulating genome replication can negatively affect VRP generation by limiting the number of genomic RNAs available for packaging into particles. Second, modulating subgenomic transcription by altering (e.g., by truncation, deletion, addition and/or substitution) the 26S promoter can alter genomic RNA replication, again resulting in limiting the number of genomic RNAs available for packaging into particles. Third, alphavirus replication induces a stress response in cells that can result in reduced cap-dependent translation of mRNAs. Switching from cap-dependent translation of an alphavirus subgenomic mRNA to the cap-independent mechanism provided by an IRES element minimizes this negative affect on NOI expression.

An IRES element of the present invention can include, but is not limited to, viral IRES elements from picornaviruses, e.g., poliovirus (PV) or the human enterovirus 71, e.g. strains 7423/MS/87 and BrCr thereof; from encephalomyocarditis virus (EMCV); from foot-and-mouth disease virus (FMDV); from flaviviruses, e.g., hepatitis C virus (HCV); from pestiviruses, e.g., classical swine fever virus (CSFV); from retroviruses, e.g., murine leukemia virus (MLV); from lentiviruses, e.g., simian immunodeficiency virus (SIV); from cellular mRNA IRES elements such as those from translation initiation factors, e.g., eIF4G or DAP5; from transcription factors, e.g., c-Myc (Yang and Sarnow, *Nucleic Acids Research* 25: 2800-2807 (1997)) or NF-κB-repressing factor (NRF); from growth factors, e.g., vascular endothelial growth factor (VEGF), fibroblast growth factor (FGF-2) and platelet-derived growth factor B (PDGF B); from homeotic genes, e.g., *Antennapedia*; from survival proteins, e.g., X-linked inlibitor of apoptosis (XIAP) or Apaf-1; from chaperones, e.g., immunoglobulin heavy-chain binding protein BiP (Martinez-Salas et al., *Journal of General Virology* 82: 973-984, (2001)), from plant viruses, as well as any other IRES elements now known or later identified.

In certain embodiments, the IRES element of this invention can be derived from, for example, encephalomyocarditis virus (EMCV, GenBank accession # NC001479), cricket paralysis virus (GenBank accession # AF218039), Drosophila C virus (GenBank accession # AF014388), Plautia stali intestine virus (GenBank accession # AB006531), Rhopalosiphum padi virus (GenBank accession # AF022937), Himetobi P virus (GenBank accession # AB017037), acute bee paralysis virus (GenBank accession # AF150629), Black queen cell virus (GenBank accession # AF183905), Triatoma virus (GenBank accession # AF178440), Acyrthosiphon pisum virus (GenBaik accession # AF024514), infectious flacherie virus (GenBank accession # AB000906), and/or Sacbrood virus (Genbank accession # AF092924). In addition, the present invention provides a synthetic IRES element, which can be designed, according to methods know in the art to mimic the function of naturally occurring IRES elements (see Chappell et al. *Proc Natl Acad Sci USA*. (2000) 97(4): 1536-41.

In specific embodiments, the IRES element can be an insect IRES element or other non-mammalian IRES element that is functional in the particular helper cell line chosen for packaging of the recombinant alphavirus particles of this invention, but would not be functional, or would be minimally functional, in a target host cell. Insect virus IRES elements have evolved to function optimally within insect cells and similarly mammalian-virus IRES sequences function optimally in mammalian cells. Thus, control of translation can be introduced into replicon vector systems by inserting insect virus-specific IRES elements into replicon RNAs. In this way, translation of heterologous NOIs from replicon vectors can be regulated (attenuated) in mammalian cells and enhanced within insect cells. This is useful for those NOIs that are either toxic to the packaging cell or are detrimental to the alphavirus packaging process. An alternative way to achieve this effect is to use a mammalian IRES element in the replicon vector that is packaged in an insect cell culture system, thereby also avoiding possibly significant translation of the heterologous NOI during packaging. Without being held to a particular hypothesis or theory, cellular factors and culture environment may play a role in IRES activity and function. Therefore, it is anticipated that additional levels of control/regulation of different IRES species within the same cell may be achieved through the supply/removal of certain cellular factors or by changes in the culture environment (e.g., temperature) to preferentially direct translation to one IRES as compared to a second.

In some embodiments, the cellular environment of the helper or packaging cell line can be altered so that a specific activity of the IRES is either enhanced or reduced. Typically, IRES elements have evolved to function under conditions of cellular stress where increased levels of eIF-2alpha kinases result in reduced cap-dependent translation and a reciprocal increase in IRES-dependent translation/activity. Such conditions can be artificially induced in a cellular packaging system so as to increase expression from chosen IRES elements by a variety of methods including but not limited to hypoxia, hypothermia, nutritional/amino acid starvation, ER stress induction (e.g. using Thapsigargin), induction of interferon or PKR elements (e.g., using poly IC), blockage of tRNA dependent synthesis (e.g., using Edeine), or other general cell stressors known in the art, including but not limited to, hydrogen peroxide and sorbitol.

In other embodiments, IRES element-directed translation of the NOI can be modulated, e.g., through the use of antisense siRNAs specific for the IRES element/spacer or NOI which can be transfected into, or transduced/transiently expressed within the packaging cell by a number of standard methods known in the art and described herein.

As another alternative, the expression of the NOI can also be modulated by the use of ligand binding pairs, e.g., a nucleic acid element and a molecule (i.e. ligand) that binds to it (see, for example, U.S. Pat. No. 6,242,259). Therefore, the present invention also provides a recombinant replicon nucleic acid comprising: a nucleic acid sequence encoding a 5' alphavirus replication recognition sequence, one or more second nucleic acid sequence(s) encoding an alphavirus nonstructural protein, at least one alphavirus subgenomic promoter, at least one IRES element, a non-alphavirus nucleotide sequence which, when bound by a ligand alters transcription of the subgenomic RNA and/or translation from the IRES, at least one heterologous nucleic acid, and a nucleic acid encoding a 3' alphavirus replication recognition sequence.

As a specific embodiment, the ligand can be an RNA binding protein (e.g., R17 coat protein), an antisense sequence, a dye (e.g., Hoechst dyes H33258 or H3342), and/or an antibiotic (e.g. tobramycin or kanamycin). These can be introduced into or produced in the packaging cells by methods known to those in the art (see U.S. Pat. No. 6,242,259).

As utilized within the context of the present invention, a reduction of either transcription of subgenomic RNA, or a reduction of translation of a NOI directed by the IRES, due to the action of a ligand binding to a non-alphavirus nucleotide sequence located in close proximity to the alphavirus subgenomic promoter or IRES should be understood to refer to a statistically significant decrease of either transcription or translation, respectively, in the presence of the selected ligand. In some embodiments, the level of either transcription of subgenomic RNA or IRES-directed NOI translation in cells is reduced at least 25%, 50%, 75%, or 90%, or 3-fold, 5-fold, or 10-fold as compared to the levels without the presence of the binding ligand. A wide variety of assays that are known in the art can be utilized to assess a reduced level of transcription or translation, including for example, enzymatic assays of a reporter gene, northern blots, metabolic RNA labeling and the like.

The recombinant replicon nucleic acids of this invention can comprise one or more IRES elements and in those embodiments comprising two or more IRES elements, the IRES elements can be the same or they can be different, in any order and/or combination. In specific embodiments, the recombinant replicon nucleic acid can comprise two or more "promoter-IRES-heterologous NOI cassettes," in which the promoter, IRES and heterologous NOI in each cassette can be either different or the same. Alternatively, the recombinant replicon nucleic acid can encode two or more NOIs, one of which is controlled by a "promoter-IRES cassette," while the other NOI(s) can be controlled by a subgenomic promoter alone or by an IRES alone.

The heterologous nucleic acid of this invention is a nucleic acid that is not present in the genome of a wild type alphavirus and/or is not present in the genome of a wild type alphavirus in the same order as it exists in a recombinant replicon nucleic acid of this invention. For example, in certain embodiments, the heterologous nucleic acid of this invention can encode one or more alphavirus structural proteins (e.g., C, PE2/E2, E1, E3, 6K) and/or one or more alphavirus structural proteins in addition to a heterologous nucleic acid. When the recombinant replicon nucleic acid of this invention comprises nucleic acid encoding one or more alphavirus structural proteins, the recombinant replicon nucleic acid can function as a recombinant replicon helper nucleic acid in the assembly of infectious, defective alphavirus particles, as described herein.

The heterologous nucleic acid of this invention can encode a protein or peptide, which can be, but is not limited to, an antigen, an immunogen or immunogenic polypeptide or peptide, a fusion protein, a fusion peptide, a cancer antigen, etc. Examples of proteins and/or peptides encoded by the heterologous nucleic acid of this invention include, but are not limited to, immunogenic polypeptides and peptides suitable for protecting a subject against a disease, including but not limited to microbial, bacterial, protozoal, parasitic, and viral diseases.

In some embodiments, for example, the protein or peptide encoded by the heterologous nucleic acid can be an orthomyxovirus immunogen (e.g., an influenza virus protein or peptide such as the influenza virus hemagglutinin (HA) surface protein or the influenza virus nucleoprotein, or an equine influenza virus protein or peptide), or a parainfluenza virus immunogen, or a metapneumovirus immunogen, or a respiratory syncytial virus immunogen, or a rhinovirus immunogen, a lentivirus immunogen (e.g., an equine infectious anemia virus protein or peptide, a Simian Immunodeficiency Virus (SIV) protein or peptide, or a Human Immunodeficiency Virus (HIV) protein or peptide, such as the HIV or SIV envelope GP160 protein, the HIV or SIV matrix/capsid proteins, and the HIV or SIV gag, pol and env gene products). The protein or peptide can also be an arenavirus immunogen (e.g., Lassa fever virus protein or peptide, such as the Lassa fever virus nucleocapsid protein and the Lassa fever envelope glycoprotein), a picornavirus immunogen (e.g., a Foot and Mouth Disease virus protein or peptide), a poxvirus immunogen (e.g., a vaccinia protein or peptide, such as the vaccinia L1 or L8 protein), an orbivirus immunogen (e.g., an African horse sickness virus protein or peptide), a flavivirus immunogen (e.g., a yellow fever virus protein or peptide, a West Nile virus protein or peptide, or a Japanese encephalitis virus protein or peptide), a filovirus immunogen (e.g., an Ebola virus protein or peptide, or a Marburg virus protein or peptide, such as NP and GP proteins), a bunyavirus immunogen (e.g., RVFV, CCHF, and SFS proteins or peptides), or a coronavirus immunogen (e.g., an infectious human coronavirus protein or peptide, such as the human coronavirus envelope glycoprotein, or a porcine transmissible gastroenteritis virus protein or peptide, or an avian infectious bronchitis virus protein or peptide). The protein or polypeptide encoded by the heterologous nucleic acid of this invention can further be a polio antigen, herpes antigen (e.g., CMV, EBV, HSV antigens) mumps antigen, measles antigen, rubella antigen, varicella antigen, botulinum toxin, diphtheria toxin or other diphtheria antigen, pertussis antigen, hepatitis (e.g., Hepatitis A, Hepatitis B, Hepatitis C, Hepatitis D, or Hepatitis E) antigen, or any other vaccine antigen known in the art.

As used herein, "eliciting an immune response" and "immunizing a subject" includes the development, in a subject, of a humoral and/or a cellular immune response to a protein and/or polypeptide of this invention (e.g., an immunogen, an antigen, an immunogenic peptide, and/or one or more epitopes). A "humoral" immune response, as this term is well known in the art, refers to an immune response comprising antibodies, while a "cellular" immune response, as this term is well known in the art, refers to an immune response comprising T-lymphocytes and other white blood cells, especially the immunogen-specific response by HLA-restricted cytolytic T-cells, i.e., "CTLs." A cellular immune response occurs when the processed immunogens, i.e., peptide fragments, are displayed in conjunction with the major histocompatibility complex (MHC) HLA proteins, which are of two general types, class I and class II. Class I HLA-restricted CTLs generally bind 9-mer peptides and present those peptides on the cell surface. These peptide fragments in the context of the HLA Class I molecule are recognized by specific T-Cell Receptor (TCR) proteins on T-lymphocytes, resulting in the activation of the T-cell. The activation can result in a number of functional outcomes including, but not limited to expansion of the specific T-cell subset resulting in destruction of the cell bearing the HLA-peptide complex directly through cytotoxic or apoptotic events or the activation of non-destructive mechanisms, e.g., the production of interferon/cytokines. Presentation of immunogens via Class I MHC proteins typically stimulates a CD8+ CTL response.

Another aspect of the cellular immune response involves the HLA Class II-restricted T-cell responses, involving the activation of helper T-cells, which stimulate and focus the activity of nonspecific effector cells against cells displaying the peptide fragments in association with the MHC molecules on their surface. At least two types of helper cells are recognized: T-helper 1 cells (Th1), which secrete the cytokines interleukin 2 (IL-2) and interferon-gamma and T-helper 2 cells (Th2), which secrete the cytokines interleukin 4 (IL-4), interleukin 5 (IL-5), interleukin 6 (IL-6) and interleukin 10 (IL-10). Presentation of immunogens via Class II MHC proteins typically elicits a CD4# CTL response as well as stimulation of B lymphocytes, which leads to an antibody response.

An "immunogenic polypeptide," "immunogenic peptide," or "immunogen" as used herein includes any peptide, protein or polypeptide that elicits an immune response in a subject and in certain embodiments, the immunogenic polypeptide is suitable for providing some degree of protection to a subject against a disease. These terms can be used interchangeably with the term "antigen."

In certain embodiments, the immunogen of this invention can comprise, consist essentially of, or consist of one or more "epitopes." An "epitope" is a set of amino acid residues that is involved in recognition by a particular immunoglobulin. In the context of T cells, an epitope is defined as the set of amino acid residues necessary for recognition by T cell receptor proteins and/or MHC receptors. In an immune system setting, in vivo or in vitro, an epitope refers to the collective features of a molecule, such as primary, secondary and/or tertiary peptide structure, and/or charge, that together form a site recognized by an immunoglobulin, T cell receptor and/or HLA molecule. In the case of a B-cell (antibody) epitope, it is typically a minimum of 3-4 amino acids, preferably at least 5, ranging up to approximately 50 amino acids. Preferably, the humoral response-inducing epitopes are between 5 and 30 amino acids, usually between 12 and 25 amino acids, and most commonly between 15 and 20 amino acids. In the case of a T-cell epitope, an epitope includes at least about 7-9 amino acids, and for a helper T-cell epitope, at least about 12-20 amino acids. Typically, such a T-cell epitope will include between about 7 and 15 amino acids, e.g., 7, 8, 9, 10, 11, 12, 13, 14 or 15 amino acids.

The present invention can be employed to express a nucleic acid encoding an immunogenic polypeptide in a subject (e.g., for vaccination) or for immunotherapy (e.g., to treat a subject with cancer or tumors). Thus, in the case of vaccines, the present invention thereby provides methods of eliciting an immune response in a subject, comprising administering to the subject an immunogenic amount of a nucleic acid, particle, population and/or composition of this invention.

It is also contemplated that the nucleic acids, particles, populations and pharmaceutical compositions of this invention can be employed in methods of delivering a NOI of interest to a cell, which can be a cell in a subject. Thus, the present invention provides a method of delivering a heterologous nucleic acid to a cell comprising introducing into a cell an effective amount of a nucleic acid, particle, population and/or composition of this invention. Also provided is a method of delivering a heterologous nucleic acid to a cell in a subject, comprising delivering to the subject an effective amount of a nucleic acid, particle, population and/or composition of this invention. Such methods can be employed to impart a therapeutic effect on a cell and/or a subject of this invention, according to well known protocols for gene therapy.

A "subject" of this invention includes, but is not limited to, warm-blooded animals, e.g., humans, non-human primates, horses, cows, cats, dogs, pigs, rats, and mice. Administration of the various compositions of this invention (e.g., nucleic acids, particles, populations, pharmaceutical compositions) can be accomplished by any of several different routes. In specific embodiments, the compositions can be administered intramuscularly, subcutaneously, intraperitoneally, intradermally, intranasally, intracranially, sublingually, intravaginally, intrarectally, orally, or topically. The compositions herein may be administered via a skin scarification method, or transdermally via a patch or liquid. The compositions can be delivered subdermally in the form of a biodegradable material that releases the compositions over a period of time.

The compositions of this invention can be used prophylactically to prevent disease or therapeutically to treat disease. Diseases that can be treated include infectious disease caused by viruses, bacteria, fungi or parasites, and cancer. Chronic diseases involving the expression of aberrant or abnormal proteins or the over-expression of normal proteins, can also be treated, e.g., Alzheimer's, disease multiple sclerosis, stroke, etc.

The compositions of this invention can be optimized and combined with other vaccination regimens to provide the broadest (i.e., all aspects of the immune response, including those features described hereinabove) cellular and humoral responses possible. In certain embodiments, this can include the use of heterologous prime-boost strategies, in which the compositions of this invention are used in combination with a composition comprising one or more of the following: immunogens derived from a pathogen or tumor, recombinant immunogens, naked nucleic acids, nucleic acids formulated with lipid-containing moieties, non-alphavirus vectors (including but not limited to pox vectors, adenoviral vectors, herpes vectors, vesicular stomatitis virus vectors, paramyxoviral vectors, parvovirus vectors, papovavirus vectors, retroviral vectors), and other alphavirus vectors. The viral vectors can be virus-like particles or nucleic acids. The alphavirus vectors can be replicon-containing particles, DNA-based replicon-containing vectors (sometimes referred to as an "ELVIS" system, see, for example, U.S. Pat. No. 5,814,482) or naked RNA vectors.

The compositions of the present invention can also be employed to produce an immune response against chronic or latent infectious agents, which typically persist because they fail to elicit a strong immune response in the subject. Illustrative latent or chronic infectious agents include, but are not limited to, hepatitis B, hepatitis C, Epstein-Barr Virus, herpes viruses, human immunodeficiency virus, and human papilloma viruses. Alphavirus vectors encoding peptides and/or proteins from these infectious agents can be administered to a cell or a subject according to the methods described herein.

Alternatively, the immunogenic protein or peptide can be any tumor or cancer cell antigen. Preferably, the tumor or cancer antigen is expressed on the surface of the cancer cell. Exemplary cancer antigens for specific breast cancers are the HER2 and BRCA1 antigens. Other illustrative cancer and tumor cell antigens are described in S. A. Rosenberg, (1999) *Immunity* 10: 281) and include, but are not limited to, MART-1/MelaiA, gp100, tyrosinase, TRP-1, TRP-2, MAGE-1, MAGE-3, GAGE-1/2, BAGE, RAGE, NY-ESO-1, CDK-4, β-catenin, MUM-1, Caspase-8, KIAA0205, HPVE&, SART-1, PRAME, p15 and p53 antigens, Wilms' tumor antigen, tyrosinase, carcinoembryonic antigen (CEA), prostate specific antigen (PSA), prostate-specific membrane antigen (PSMA), prostate stem cell antigen (PSCA), human aspartyl (asparaginyl) β-hydroxylase (HAAH), and EphA2 (an epithelial cell tyrosine kinase, see International Patent Publication No. WO 01/12172).

The immunogenic polypeptide or peptide of this invention can also be a "universal" or "artificial" cancer or tumor cell antigen as described in international patent publication WO 99/51263, which is incorporated herein by reference in its entirety for the teachings of such antigens.

In various embodiments, the heterologous nucleic acid of this invention can encode an antisense nucleic acid sequence. An "antisense" nucleic acid is a nucleic acid molecule (i.e., DNA or RNA) that is complementary (i.e., able to hybridize in vivo or under stringent in vitro conditions) to all or a portion of a nucleic acid (e.g., a gene, a cDNA and/or mRNA) that encodes or is involved in the expression of nucleic acid that encodes a polypeptide to be targeted for inhibited or reduced production by the action of the antisense nucleic acid. If desired, conventional methods can be used to produce an antisense nucleic acid that contains desirable modifications. For example, a phosphorothioate oligonucleotide can be used as the antisense nucleic acid to inhibit degradation of the antisense oligonucleotide by nucleases in vivo. Where the antisense nucleic acid is complementary to a portion of the nucleic acid encoding the polypeptide to be targeted, the antisense nucleic acid should hybridize close enough to the 5' end of the nucleic acid encoding the polypeptide such that it inhibits translation of a functional polypeptide. Typically, this means that the antisense nucleic acid should be complementary to a sequence that is within the 5' half or third of the nucleic acid to which it hybridizes.

An antisense nucleic acid of this invention can also encode a catalytic RNA (i.e., a ribozyme) that inhibits expression of a target nucleic acid in a cell by hydrolyzing an mRNA encoding the targeted gene product. Additionally, hammerhead RNA can be used as an antisense nucleic acid to prevent intron splicing. An antisense nucleic acid of this invention can be produced and tested according to protocols routine in the art for antisense technology.

The term "alphavirus" as used herein has its conventional meaning in the art, and includes Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86 (S.A.AR86), Girdwood S.A. virus, Ockelbo virus, Semliki Forest virus, Middleburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babalki virus, Kyzlagach virus, Highlands J virus, Fort Morgan virus, Ndumu virus, Buggy Creek virus, and any other virus classified by the International Committee on Taxonomy of Viruses (ICTV) as an alphavirus.

In specific embodiments of this invention, the nucleic acids and/or the proteins encoded by the nucleic acids of the present invention can comprise attenuating mutations. The phrases "attenuating mutation" and "attenuating amino acid," as used herein, include a nucleotide sequence containing a mutation, or an amino acid encoded by a nucleotide sequence containing a mutation, which results in a decreased probability of causing disease in its host (i.e., reduction in or "attenuation of" virulence), in accordance with standard terminology in the art. See, e.g., Davis et al., MICROBIOLOGY 132 (3d ed. 1980). The phrase "attenuating mutation" excludes mutations or combinations of mutations that would be lethal to the virus. However, it does include those otherwise lethal mutations that can be incorporated in combination with a resuscitating or rescuing mutation that leads to an attenuated phenotype.

Appropriate attenuating mutations will be dependent upon the alphavirus used, and will be known to those skilled in the art. Exemplary attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., and U.S. Pat. No. 5,639,650 to Johnston et al., the disclosures of each of which are incorporated herein in their entireties by reference.

In various embodiments of this invention, one or more of the alphavirus structural proteins of the alphavirus particles of this invention can comprise one or more attenuating mutations, for example, as defined in U.S. Pat. Nos. 5,792,462 and 6,156,558. Specific attenuating mutations for the VEE E1 glycoprotein can include an attenuating mutation at any one of E1 amino acid positions 81, 272 and/or 253. Alphavirus particles made from the VEE-3042 mutant contain an isoleucine substitution at E1-81, and virus particles made from the VEE-3040 mutant contain an attenuating mutation at E1-253. Specific attenuating mutations for the VEE E2 glycoprotein can include an attenuating mutation at any one of E2 amino acid positions 76, 120, or 209. Alphavirus particles made from the VEE-3014 mutant contain attenuating mutations at both E1-272 and at E2-209 (see U.S. Pat. No. 5,792,492). A specific attenuating mutation for the VEE E3 glycoprotein includes an attenuating mutation consisting of a deletion of E3 amino acids 56-59. Virus particles made from the VEE-3526 mutant contain this deletion in E3 (aa56-59) as well as a second attenuating mutation at E1-253. Specific attenuating mutations for the S.A.AR86E2 glycoprotein include an attenuating mutation at any one of E2 amino acid positions 304, 314, 372, or 376. Alternatively, the attenuating mutation can be a substitution, deletion and/or insertion of an amino acid in the E2 glycoprotein, for example, at any one or more of the following amino acid positions in any combination: 158, 159, 160, 161 and 162 (see Polo et al., PCT Publication No. WO00/61772, the entire contents of which are incorporated by reference herein).

Another attenuating mutation of this invention can be an attenuating mutation at nucleotide 3 of the VEE genomic RNA, i.e., the third nucleotide following the 5' methylated cap (see, e.g., U.S. Pat. No. 5,643,576, describing a G→C mutation at nt 3). The mutation can be a G→A, U or C, but can also be a G→A mutation in some embodiments.

When the alphavirus structural and/or non-structural proteins are from S.A.AR86, exemplary attenuating mutations in the structural and non-structural proteins include, but are not limited to, codons at nsp1 amino acid position 538 which specify an attenuating amino acid, preferably isoleucine as nsp1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid 372 which specify an attenuating amino acid, preferably leucine, at E2 amino acid residue 372; codons at E2 amino acid position 376 which specify an attenuating amino acid, preferably alanine as E2 amino acid 376; in combination, codons at E2 amino acid residues 304, 314, 372 and 376 which specify attenuating amino acids, as described above; codons at nsp2 amino acid position 96 which specify an attenuating amino acid, preferably glycine as nsp2 amino acid 96; and codons at nsp2 amino acid position 372 which specify an attenuating amino acid, preferably valine as nsp2 amino acid 372; in combination, codons at nsp2 amino acid residues 96 and 372 which encode attenuating amino acids at nsp2 amino acid residues 96 and 372, as described above; codons at nsp2 amino acid residue 529 which specify an attenuating amino acid, preferably leucine, at nsp2 amino acid residue 529; codons at nsp2 amino acid residue 571 which specify an attenuating amino acid, preferably asparagine, at nsp2 amino acid residue 571; codons at nsp2 amino acid residue 682 which specify an attenuating amino acid, preferably arginine, at nsp2 amino acid residue 682; codons at nsp2 amino acid residue 804 which specify an attenuating amino acid, preferably arginine, at nsp2 amino acid residue 804; codons at nsp3 amino acid residue 22 which specify an attenuating amino acid, preferably arginine, at nsp3 amino acid residue 22; and in combination, codons at nsp2 amino acid residues 529, 571, 682 and 804 and at nsp3 amino acid residue 22 which specify attenuating amino acids, as described above.

Other illustrative attenuating mutations include those described in PCT Application No. PCT/US01/27644 (the disclosure of which is incorporated herein in its entirety by reference). For example, the attenuating mutation can be an attenuating mutation at amino acid position 5.37 of the S.A.AR86 nsp3 protein, more preferably a substitution mutation at this position, still more preferably a nonsense mutation that results in substitution of a termination codon. Translational termination (i.e., stop) codons are known in the art, and include the "opal" (UGA), "amber" (UAG) and "ochre" (UAA) termination codons. In embodiments of the invention, the attenuating mutation can result in a Cys→opal substitution at S.A.AR86 nsp3 amino acid position 537.

Further exemplary attenuating mutations can include an attenuating insertion mutation following amino acid 385 of the S.A.AR86 nsp3 protein. The insertion can comprise an insertion of at least 2, 4, 6, 8, 10, 12, 14, 16 or 20 amino acids. In some embodiments of the invention, the inserted amino acid sequence is rich in serine and threonine residues (e.g., comprises at least 2, 4, 6, or 8 such sites) that serve as a substrate for phosphorylation by serine/threonine kinases.

In certain embodiments, the attenuating mutation can comprise insertion of the amino acid sequence Ile-Thr-Ser-Met-Asp-Ser-Trp-Ser-Ser-Gly-Pro-Ser-Ser-Leu-Glu-Ile-Val-Asp (SEQ ID NO:1) following amino acid 385 of nsp3 (i.e., the first amino acid is designated as amino acid 386 in nsp3). In other embodiments of the invention, the insertion mutation can comprise insertion of a fragment of SEQ ID NO:1 that results in an attenuated phenotype. The fragment can comprise at least 4, 6, 8, 10, 12, 14, 15, 16 or 17 contiguous amino acids from SEQ ID NO:1.

Those skilled in the art will appreciate that other attenuating insertion sequences comprising a fragment of the sequence set forth above, or which incorporate conservative amino acid substitutions into the sequence set forth above, can be routinely identified by routine methods (as described above). While not wishing to be bound by any theory of the invention, it appears that the insertion sequence of SEQ ID NO:1 is highly phosphorylated at serine residues, which confers an attenuated phenotype. Thus, other attenuating insertion sequences that serve as substrates for serine (or threonine) phosphorylation can be identified by conventional techniques known in the art. Alternatively, or additionally, there is a Tyr→Ser substitution at amino acid 385 of the S.A.AR86 nsp3 protein (i.e., just prior to the insertion sequence above). This sequence is conserved in the non-virulent Sindbis-group viruses, but is deleted from S.A.AR86

In other embodiments, the alphavirus of this invention can be any Sindbis virus strain (e.g., TR339), VEE (having a mutation at nucleotide 3 of the genomic RNA following the methylated cap), S.A.AR86 virus, Girdwood S.A. virus, Ockelbo virus, and/or chimeric viruses thereof. The complete genomic sequences, as well as the sequences of the various structural and non-structural proteins, are known in the art for numerous alphaviruses and include: Sindbis virus genomic sequence (GenBank Accession No. J02363, NCBI Accession No. NC_001547), S.A.AR86 genomic sequence (GenBank Accession No. U38305), VEE genomic sequence (GenBank Accession No. L04653, NCBI Accession No. NC_001449), Girdwood S.A genomic sequence (GenBaik Accession No. U38304), Semliki Forest virus genomic sequence (GenBank Accession No. X04129, NCBI Accession No. NC_003215), and the TR339 genomic sequence (Klimstra et al. (1988) *J. Virol.* 72: 7357; McKnight et al. (1996) *J. Virol.* 70: 1981).

In particular embodiments of the present invention, the alphavirus structural protein of this invention can be a Sindbis virus structural protein, a SFV structural protein, a VEE structural protein, a Ross River virus structural protein, a S.A. AR86 structural protein, an EEE structural protein and/or a WEE structural protein. These can be present in any combination with one another and can be present in combination with any alphavirus nonstructural proteins and/or other alphaviral sequences, such as the 5' alphavirus replication recognition sequence, the alphavirus subgenomic promoter and the 3' alphavirus replication recognition sequence, from any of these and/or other alphaviruses, to produce chimeric recombinant alphavirus particles and/or chimeric recombinant nucleic acids of this invention.

In further embodiments, the IRES element of this invention directs the translation of the gene product encoded by the heterologous nucleic acid of the recombinant nucleic acid of this invention, such that at least 10%, 15%, 20%, 25%, 30%, 35%, 40%, 45%, 50%, 55%, 60%, 65%, 70%, 75%, 80%, 85%, 90%, 92%, 94%, 95%, 96%, 97%, 98%, 99% or 100% of the translation of the gene product encoded by the heterologous nucleic acid is controlled by the activity of the IRES element. The percentage of translation of the gene product encoded by the heterologous nucleic acid in the recombinant replicon nucleic acids of this invention as controlled by the IRES can be determined according to assays well known in the art and as described in the Examples section provided herein.

Furthermore, in embodiments of this invention wherein the IRES element of this invention directs the translation of an alphavirus structural protein present in a helper construct of this invention, the IRES element of this invention can direct the translation of the structural protein(s), such that at least 10%, 15%, 20%, 25%, 30%, 35%, 40%, 45%, 50%, 55%, 60%, 65%, 70%, 75%, 80%, 85%, 90%, 92%, 94%, 95%, 96%, 97%, 98%, 99% or 100% of the translation of the structural protein is controlled by the activity of the IRES element. The percentage of translation of the structural protein(s) as controlled by the IRES element of this invention can be determined according to assays well known in the art and as described in the Examples section provided herein.

The nucleic acid of this invention can be RNA or DNA.

In another embodiment of this invention, a series of helper nucleic acids ("helper constructs" or "helper molecules"), i.e., recombinant DNA or RNA molecules that express one or more alphavirus structural proteins, are provided. In one set of RNA embodiments, the helper construct comprises a first nucleic acid sequence encoding (i) a 5' alphavirus replication recognition sequence, (ii) a transcriptional promoter, (iii) a nucleic acid sequence encoding at least one, but not all, alphavirus structural proteins, and (iv) an alphavirus 3' replication recognition sequence. In certain embodiments, the E1 and E2 glycoproteins are encoded by one helper construct, and the capsid protein is encoded by another separate helper construct. In another embodiment, the E1 glycoprotein, E2 glycoprotein, and capsid protein are each encoded by separate helper constructs. In other embodiments, the capsid protein and one of the glycoproteins are encoded by one helper construct, and the other glycoprotein is encoded by a separate second helper construct. In yet further embodiments, the capsid protein and glycoprotein E1 are encoded by one helper construct and the capsid protein and glycoprotein E2 are encoded by a separate helper construct. In certain embodiments, the helper constructs of this invention do not include an alphavirus packaging signal.

Alternatively, the above-described helper nucleic acids are constructed as DNA molecules, which can be stably integrated into the genome of a helper cell or expressed from an episome (e.g., an EBV derived episome). The DNA molecule can also be transiently expressed in a cell. The DNA molecule can be any vector known in the art, including but not limited to, a non-integrating DNA vector, such as a plasmid, or a viral vector. The DNA molecule can encode one or all of the alphavirus structural proteins, in any combination, as described herein.

The helper constructs of this invention are introduced into "helper cells," which are used to produce the alphavirus particles of this invention. As noted above, the nucleic acids encoding alphavirus structural proteins can be present in the helper cell transiently or by stable integration into the genome of the helper cell. The nucleic acid encoding the alphavirus structural proteins that are used to produce alphavirus particles of this invention can be under the control of constitutive and/or inducible promoters. As also noted above, the alpha virus structural protein coding sequences can be provided on a recombinant replicon nucleic acid and/or a helper construct comprising an IRES element and the translation of these coding sequences can be controlled by the activity of an IRES element. In such embodiments, the IRES element can be active in the specific helper cell type and not active, or minimally active in other cells types. In particular embodiments, the helper cells of the invention comprise nucleic acid sequences encoding the alphavirus structural proteins in a combination and/or amount sufficient to produce an alphavirus particle of this invention when a recombinant replicon nucleic acid is introduced into the cell under conditions whereby the alphavirus structural proteins are produced and the recombinant replicon nucleic acid is packaged into alphavirus particle of this invention.

In all of the embodiments of this invention, it is contemplated that at least one of the alphavirus structural and/or non-structural proteins encoded by the recombinant replicon nucleic acid and/or helper molecules, and/or the nontranslated regions of the recombinant replicon and/or helper nucleic acid, can contain one or more attenuating mutations in any combination, as described herein and as are well known in the literature.

In particular constructs of this invention, a promoter for directing transcription of RNA from DNA, i.e., a DNA dependent RNA polymerase, is employed. In the RNA helper and replicon embodiments of this invention, the promoter is utilized to synthesize RNA in an in vitro transcription reaction, and specific promoters suitable for this use include, but are not limited to, the SP6, T7, and T3 RNA polymerase promoters. In the DNA helper embodiments, the promoter functions within a cell to direct transcription of RNA. Potential promoters for in vivo transcription of the construct include, but are not limited to, eukaryotic promoters such as RNA polymerase II promoters, RNA polymerase III promoters, or viral promoters such as MMTV and MoSV LTR, SV40 early region, RSV or CMV. Many other suitable mammalian and viral promoters for the present invention are available and are known in the art. Alternatively, DNA dependent RNA polymerase promoters from bacteria or bacteriophage, e.g., SP6, T7, and T3, can be employed for use in vivo, with the matching RNA polymerase being provided to the cell, either via a separate plasmid, RNA vector, or viral vector. In a specific embodiment, the matching RNA polymerase can be stably transformed into a helper cell line under the control of an inducible promoter. Constructs that function within a cell can function as autonomous plasmids transfected into the cell and/or they can be stably transformed into the genome. In a stably transformed cell line, the promoter can be an inducible promoter, so that the cell will only produce the RNA polymerase encoded by the stably transformed construct when the cell is exposed to the appropriate stimulus (inducer). The helper constructs are introduced into the stably transformed cell concomitantly with, prior to, and/or after exposure to, the inducer, thereby effecting expression of the alphavirus structural proteins. Alternatively, constructs designed to function within a cell can be introduced into the cell via a viral vector, such as, e.g., adenovirus, poxvirus, adeno-associated virus, SV40, retrovirus, nodavirus, picornavirus, vesicular stomatitis virus, and baculoviruses with mammalian pol II promoters.

In certain embodiments of the invention provided herein, the recombinant replicon nucleic acid and/or helper nucleic acid of this invention can comprise a spacer nucleic acid, which can be located upstream of an IRES element in a recombinant replicon nucleic acid and/or helper nucleic acid of this invention. The spacer nucleic acid can comprise, consist essentially of, or consist of any random or specific non-coding nucleic acid sequence which is of a length sufficient to prevent at least some, and in some embodiments, all translation from the 5' cap of a messenger RNA, such that translation is then directed by the IRES, in part or in whole. Alternatively, the spacer nucleic acid can be of a length and sequence structure that imparts sufficient secondary structure to the nucleic acid to prevent at least some and possibly all translation activity from the 5' cap of a messenger RNA.

As one example, a commercially available plasmid, pcDNA 3.1(−), was digested with a restriction enzyme, AluI, which cuts frequently within this plasmid, thus generating many random and differently sized fragments (see Example 3 for details). The pCDNA plasmid is 5427 nucleotides in length, and is a eukaryotic expression vector, comprising various promoters (CMV, T7, SV40) for expression of an inserted nucleic acid as well as polyadenylation signals and antibiotic resistance genes. The AluI enzyme cuts throughout these elements, providing a range of random fragments. Examples of several different spacers and their sequences that were generated from this example and which do not encode any functional elements from the plasmid, are provided hereinbelow:

```
357 nucleotide spacer: (SEQ ID NO:2)
CTGAATGAAGCCATACCAAACGACGAGCGTGACACCACGATGCCTGTAGC
AATGGCAACAACGTTGCGCAAACTATTAACTGGCGAACTACTTACTCTAG
CTACCAACTCTTTTTCCGAAGGTAACTGGCTTCAGCAGAGCGCAGATACC
AAATACTGTTCTTCTAGTGTAGCCGTAGTTAGGCCACCACTTCAAGAACT
CTGTAGCACCGCCTACATACCTCGCTCTGCTAATCCTGTTACCAGTGGCT
GCTGCCAGTGGCGATAAGTCGTGTCTTACCGGGTTGGACTCAAGACGATA
GTTACCGGATAAGGCGCAGCGGTCGGGCTGAACGGGGGGTTCGTGCACAC
AGCCCAG 342 nucleotide spacer: (SEQ ID NO:3)
CTATTCCAGAAGTAGTGAGGAGGCTTTTTTGGAGGCCTAGGCTTTTGCAA
AAAGCTTGTATATCCATTTTCGGATCTGATCAAGAGACAGGATGAGGATC
GTTTCGCATGATTGAACAAGATGGATTGCACGCAGGTTCTCCGGCCGCTT
GGGTGGAGAGGCTATTCGGCTATGACTGGGCACAACAGACAATCGGCTGC
TCTGATGCCGCCGTGTTCCGGCTGTCAGCGCAGGGGCGCCCGGTTCTTTT
```

-continued
TGTCAAGACCGACCTGTCCGGTGCCCTGAATGAACTGCAGGACGAGGCAG
CGCGGCTATCGTGGCTGGCCACGACGGGCGTTCCTTGCGCAG 257 nucleotide spacer: (SEQ ID NO:4)
CTCATTTTTTAACCAATAGGCCGAAATCGGCAAAATCCCTTATAAATCAA
AAGAATAGACCGAGATAGGGTTGAGTGTTGTTCCAGTTTGGAACAAGAGT
CCACTATTAAAGAACGTGGACTCCAACGTCAAAGGGCGAAAAACCGTCTA
TCAGGGCGATGGCCCACTACGTGAACCATCACCCTAATCAAGTTTTTTGG
GGTCGAGGTGCCGTAAAGCACTAAATCGGAACCCTAAAGGGAGCCCCCGA
TTTAGAG 383 nucleotide spacer: (SEQ ID NO:5)
CTGCGCAAGGAACGCCCGTCGTGGCCAGCCACGATAGCCGCGCTGCCTCG
TCCTGCAGTTCATTCAGGGCACCGGACAGGTCGGTCTTGACAAAAAGAAC
CGGGCGCCCTGCGCTGACAGCCGGAACACGGCGGCATCAGAGCAGCCGA
TTGTCTGTTGTGCCCAGTCATAGCCGAATAGCCTCTCCACCCAAGCGGCC
GGAGAACCTGCGTGCAATCCATCTTGTTCAATCATGCGAAACGATCCTCA
TCCTGTCTCTTGATCAGATCCGAAAATGGATATACAAGCTCACTCATTAG
GCACCCCAGGCTTTACACTTTATGCTTCCGGCTCGTATGTTGTGTGGAAT
TGTGAGCGGATAACAATTTCACACAGGAAACAG 579 nucleotide spacer: (SEQ ID NO:6)
CTGCAATAAACAAGTTGGGGTGGGCGAAGAACTCCAGCATGAGATCCCCG
CGCTGGAGGATCATCCAGCCGGCGTCCCGGAAAACGATTCCGAAGCCCAA
CCTTTCATAGAAGGCGGCGGTGGAATCGAAATCTCGTGATGGCAGGTTGG
GCGTCGCTTGGTCGGTCATTTCGAACCCCAGAGTCCCGCTCAGAAGAACT
CGTCAAGAAGGCGATAGAAGGCGATGCGCTGCGAATCGGGAGCGGCGATA
CCGTAAAGCACGAGGAAGCGGTCAGCCCATTCGCCGCCAAGCTTGTATAT
CCATTTTCGGATCTGATCAAGAGACAGGATGAGGATCGTTTCGCATGATT
GAACAAGATGGATTGCACGCAGGTTCTCCGGCCGCTTGGGTGGAGAGGCT
ATTCGGCTATGACTGGGCACAACAGACAATCGGCTGCTCTGATGCCGCCG
TGTTCCGGCTGTCAGCGCAGGGGCGCCCGGTTCTTTTTGTCAAGACCGAC
CTGTCCGGTGCCCTGAATGAACTGCAGGACGAGGCAGCGCGGCTATCGTG
GCTGGCCACGACGGGCGTTCCTTGCGCAG 749 nucleotide spacer: (SEQ ID NO:7)
CTGCAATAAACAAGTTGGGGTGGGCGAAGAACTCCAGCATGAGATCCCCG
CGCTGGAGGATCATCCAGCCGGCGTCCCGGAAAACGATTCCGAAGCCCAA
CCTTTCATAGAAGGCGGCGGTGGAATCGAAATCTCGTGATGGCAGGTTGG
GCGTCGCTTGGTCGGTCATTTCGAACCCCAGAGTCCCGCTCAGAAGAACT
CGTCAAGAAGGCGATAGAAGGCGATGCGCTGCGAATCGGGAGCGGCGATA
CCGTAAAGCACGAGGAAGCGGTCAGCCCATTCGCCGCCAAGCTTCTTCAGC
AATATCACGGGTAGCCAACGCTATGTCCTGATAGCGGTCCGCCACACCCA
GCCGGCCACAGTCGATGAATCCAGAAAAGCGGCCATTTTCCACCATGATA
TTCGGCAAGCAGGCATCGCCATGGGTCACGACGAGATCCTCGCCGTCGGG
CATGCGCGCCTTGAGCCTGGCGAACAGTTCGGCTGGCGCGAGCCCCTGAT
GCTCTTCGTCCAGATCATCCTGATCGACAAGACCGGCTTCCATCCGAGTA
CGTGCTCGCTCGATGCGATGTTTCGCTTGGTGGTCGAATGGGCAGGTAGC
CGGATCAAGCGTATGCAGCCGCCGCATTGCATCAGCCATGATGGATACTT
TCTCGGCAGGAGCAAGGTGAGATGACAGGAGATCCTGCCCCGGCACTTCG
CCCAATAGCAGCCAGTCCCTTCCCGCTTCAGTGACAACGTCGAGCACAG In addition to the use of random nucleic acid fragments generated from an unrelated plasmid (as in the AluI fragments described above), it is also possible to use fragments from cellular or viral genes, e.g., from the 5' non-coding regions of genes, as spacers. One approach is to use the non-coding sequences surrounding an existing IRES (see Example 4B.4.); another approach is to use the 5' non-coding region of an alphaviral gene, e.g., the capsid gene (see Example 4A.2.)

Thus, it is contemplated that the spacer nucleic acid of this invention can be at a minimum, at least 25 nucleic acids in length and can be as long as permissible in a given recombinant replicon nucleic acid. For example, the spacer nucleic acid of this invention can be, in certain embodiments, approximately 25, 30, 35, 40, 45, 50, 55, 60, 65, 75, 80, 85, 90, 95, 100, 110, 115, 120, 125, 130, 135, 140, 145, 150, 160, 170, 175, 180, 190, 200, 210, 220, 225, 230, 235, 240, 245, 250, 275, 300, 325, 350, 375, 400, 425, 450, 475, 50, 600, 700, 800, 900, 1000, 1500, 2000, 2500, 3000, 3500, 4000, 4500, 5000, 5500, 6000, 6500, 7000, 7500, 8000, 8500, 9000, 9500, or 10,000 nucleotides in length. By "approximately" it is meant that the spacer nucleic acid can vary up to 10%, 15%, 20% and/or 25% in length.

The spacer nucleic acid of this invention can also be a nucleotide sequence placed 3' to a 5' sequence for initiating transcription of a messenger RNA, and 5' to a functional IRES element, wherein the level of translation directed from said IRES element is at least approximately five fold higher than the level obtained from a non-functional IRES element. In preferred embodiments, the level of translation is at least approximately 10-fold, 20-fold, 50-fold, 100-fold, 150-fold, 180-fold, 200-fold, 300-fold, 400-fold or 500-fold higher. In other embodiments, at least 10%, 20%, 30%, 40%, 50%, 60%, 70%, 80%, 85%, 90%, 92%, 94%, 95%, 96%, 97%, 98%, 99% or 100% of the translation of the gene product encoded by the heterologous nucleic acid and/or the structural protein(s) encoded by an IRES-containing helper construct is controlled by the activity of the IRES element.

The present invention also provides an alphavirus particle comprising a recombinant replicon nucleic acid of this invention. Also provided is a population of infectious, defective, alphavirus particles, wherein each particle contains an alphavirus replicon RNA comprising the recombinant replicon nucleic acid of this invention. In some embodiments, the population of this invention has no detectable replication-competent virus, as measured by passage on cell culture and/or other well known assays for detection of replication competent virus.

The present invention further provides a pharmaceutical composition comprising a nucleic acid, vector, particle and/or population of this invention in a pharmaceutically acceptable carrier. By "pharmaceutically acceptable" is meant a material that is not biologically or otherwise undesirable, i.e., the material may be administered to an individual along with the selected peptide, polypeptide, nucleic acid, vector or cell without causing substantial deleterious biological effects or interacting in a deleterious manner with any of the other components of the composition in which it is contained.

Furthermore, any of the compositions of this invention can comprise a pharmaceutically acceptable carrier and a suitable adjuvant. As used herein, "suitable adjuvant" describes an adjuvant capable of being combined with the peptide or polypeptide of this invention to further enhance an immune response without deleterious effect on the subject or the cell of the subject. A suitable adjuvant can be, but is not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), aluminum salts (alum), aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion. Adjuvants can be combined, either with the compositions of this invention or with other vaccine compositions that can be used in combination with the compositions of this invention. Examples of adjuvants can also include, but are not limited to, oil-in-water emulsion formulations, immunostimulating agents, such as bacterial cell wall components or synthetic molecules, or oligonucleotides (e.g. CpGs) and nucleic acid polymers (both double stranded and single stranded RNA and DNA), which can incorporate alternative backbone moieties, e.g., polyvinyl polymers.

The compositions of the present invention can also include other medicinal agents, pharmaceutical agents, carriers, diluents, immunostimulatory cytokines, etc. Actual methods of preparing such dosage forms are known, or will be apparent, to those skilled in this art. Preferred dosages for alphavirus replicon particles, as contemplated by this invention, can range from $10^3$ to $10^{10}$ particles per dose. For humans, $10^6$, $10^7$ or $10^8$ are preferred doses. A dosage regimen can be one or more doses hourly, daily, weekly, monthly, yearly, etc. as deemed necessary to achieve the desired prophylactic and/or therapeutic effect to be achieved by administration of a composition of this invention to a subject. The efficacy of a particular dosage can be determined according to methods well known in the art.

The present invention further provides a method of making infectious, defective alphavirus particles, comprising: a) introducing into a cell the following: (i) a recombinant replicon nucleic acid of this invention, and (ii) one or more helper nucleic acids encoding alphavirus structural proteins, wherein the one or more helper nucleic acids produce all of the alphavirus structural proteins, and b) producing said alphavirus particles in the cell. In some embodiments, the recombinant replicon nucleic acid can comprise at least one heterologous nucleic acid encoding an alphavirus structural protein.

In other embodiments of the methods of this invention, the helper nucleic acid can be a recombinant nucleic acid comprising a 5' alphavirus replication recognition sequence, an alphavirus subgenomic promoter, a nucleic acid encoding an alphavirus structural protein and a 3 alphavirus replication recognition sequence.

In further embodiments, the helper nucleic acid can be a recombinant nucleic acid (which can be DNA) comprising a promoter (e.g., a CMV promoter) and nucleotide sequences encoding one or more, including all, alphavirus structural proteins.

The helper nucleic acid of this invention can comprise nucleic acid sequences encoding any one or more of the alphavirus structural proteins (C, E1, E2) in any order and/or in any combination. Thus, a helper cell can comprise as many helper nucleic acids as needed in order to provide all of the alphavirus structural proteins necessary to produce alphavirus particles. A helper cell can also comprise helper nucleic acid(s) stably integrated into the genome of a helper (e.g., packaging) cell. In such helper cells, the alphavirus structural proteins can be produced under the control of a promoter that can be an inducible promoter.

In some embodiments, the helper nucleic acid employed in the methods of this invention can be a recombinant nucleic acid comprising a 5' alphavirus replication recognition sequence, an IRES element, a nucleic acid encoding an alphavirus structural protein and a 3' alphavirus replication recognition sequence.

In further embodiments, the helper nucleic acid can be a recombinant nucleic acid comprising a 5' alphavirus replication recognition sequence, an alphavirus subgenomic promoter, an IRES element, a nucleic acid encoding one or more alphavirus structural proteins and a 3' alphavirus replication recognition sequence.

Additionally provided herein is a method of making infectious, defective alphavirus particles, comprising: a) introducing into a cell the following: i) an alphavirus replicon RNA comprising a 5' alphavirus replication recognition sequence, nucleic acid sequence(s) encoding alphavirus nonstructural proteins, an alphavirus subgenomic promoter, a heterologous nucleic acid sequence and a 3' alphavirus replication recognition sequence; and ii) one or more helper nucleic acids encoding alphavirus structural proteins comprising a 5' alphavirus replication recognition sequence, an alphavirus subgenomic promoter, an IRES element, a nucleic acid encoding one or more alphavirus structural proteins and a 3' alphavirus replication recognition sequence, whereby all of the alphavirus structural proteins are produced in the cell; and b) producing said alphavirus particles in the cell.

A method is also provided herein of making infectious, defective alphavirus particles, comprising: a) introducing into a cell the following: i) an alphavirus replicon RNA comprising a 5' alphavirus replication recognition sequence, nucleic acid sequence(s) encoding alphavirus nonstructural proteins, at least one alphavirus subgenomic promoter, at least one IRES element, at least one heterologous nucleic acid sequence and a 3' alphavirus replication recognition sequence; and ii) one or more helper nucleic acids encoding alphavirus structural proteins comprising a 5' alphavirus replication recognition sequence, an alphavirus subgenomic promoter, an IRES element, a nucleic acid encoding one or more alphavirus structural proteins and a 3' alphavirus replication recognition sequence, whereby all of the alphavirus structural proteins are produced in the cell; and b) producing said alphavirus particles in the cell.

The methods of making alphavirus particles of this invention can further comprise the step of collecting said alphavirus particles from the cell.

The present invention also provides a recombinant nucleic acid comprising 5' alphavirus replication recognition sequence, an alphavirus subgenomic promoter, an IRES element, a nucleic acid encoding one or more alphavirus structural proteins in any combination and/or order and a 3' alphavirus replication recognition sequence. In some embodiments, this recombinant helper nucleic acid can comprise a spacer nucleotide sequence that can be upstream of an IRES element. Also provided is a vector and/or a cell comprising this recombinant nucleic acid.

Additionally provided herein is recombinant nucleic acid comprising: a first nucleic acid sequence encoding a 5' alphavirus replication recognition sequence; at least one second nucleic acid sequence encoding an alphavirus nonstructural protein; a first alphavirus subgenomic promoter; a first IRES element; a first heterologous nucleic acid; a second alphavirus subgenomic promoter; a second IRES element; a third nucleic acid encoding a 3' alphavirus replication recognition sequence. In some embodiments, the first and second alphavirus subgenomic promoter can be the same or different, the first and second IRES element can be the same or different and/or the first and second heterologous nucleic acid can be the same or different. This recombinant nucleic acid can comprise an alphavirus packaging signal and/or a spacer nucleotide sequence that can be upstream of an IRES element. This recombinant nucleic acid can also comprise one or more second nucleic acid sequences encoding alphavirus nonstructural proteins in any order and/or combination, such that all four of the alphavirus nonstructural protein coding sequences are present on the recombinant nucleic acid. This recombinant nucleic acid can be present in an alphavirus particle of this invention and such particles can be present as a population of this invention and/or in a pharmaceutical composition of this invention.

Also provided is a recombinant replicon nucleic acid as described above, further comprising a third or further additional alphavirus subgenomic promoter, a third or further additional IRES element and/or a third or further additional heterologous nucleic acid. This recombinant nucleic acid can be present in an alphavirus particle of this invention and such particles can be present as a population of this invention and/or in a pharmaceutical composition of this invention. Alphavirus particles comprising this embodiment of recombinant nucleic acid can be produced according to any of the methods of this invention and can be used in any of the methods of eliciting an immune response and/or delivering a NOI to a cell.

As a further embodiment, the present invention provides a recombinant nucleic acid comprising: a promoter that directs transcription of a nucleic acid; an IRES element; and a nucleic acid comprising a coding sequence, wherein the IRES element is operably located such that translation of the coding sequence is via a cap-independent mechanism directed by the IRES element. In this embodiment, transcription of the nucleic acid is uncoupled from translation of the nucleic acid.

It is understood that the foregoing detailed description is given merely by way of illustration and that modifications and variations may be made therein without departing from the spirit and scope of the invention.

EXAMPLES

Example 1

Construction of Transfer Cloning Vectors

A. EMCV IRES-Containing Vectors

A transfer vector (pCDNA3.3) was prepared into which the encephalomyocarditis (EMCV) IRES sequence and any NOI could be introduced. Plasmid pCDNA3.1 (+) (Nitrogen) was digested with restriction enzyme Bathe and treated with T4 DNA polymerase to eliminate the unique Bathe restriction site, resulting in generation of pCDNA3.2. The pCDNA3.2 DNA was further digested with restriction enzyme Bay and also treated with T4 DNA polymerase to remove the unique Bay restriction site, resulting in generation of pCDNA3.3.

An intermediate cloning vector containing the multiple cloning site (MCS) from a VEE replicon vector was prepared by legating an ~250 bp ApaI/NotI MCS fragment into ApaI/NotI linearized pBluescript KS+ (Stratagene) DNA, generating pKS-rep2. The EMCV IRES was digested from pD1+2+3 (Kaminski et al., 1995) with restriction enzymes EcoRI and BamHI and ligated into EcoRI and BamHI linearized pKS-rep2 DNA, generating pKS-rep2/EMCV. The EMCV IRES and MCS sequence from the pKS-rep2/EMCV vector were PCR amplified using primers EMCVF(AscI).2 and EMCVR(AscI).1 (Table 1). The EMCV PCR product was digested with AscI restriction enzyme and ligated into AscI linearized VEE replicon (pERK) vector DNA, generating pERK/EMCV. To complete the transfer cloning vector, pERK/EMCV DNA was digested with EcoRV and NotI restriction enzymes and the 862 bp EcoRV/NotI fragment was ligated into EcoRV and NotI linearized pCDNA3.3 DNA, generating pCDNA3.3/EMCV. The sequence of the EMCV IRES and associated multiple cloning sites was confirmed in the pCDNA3.3/EMCV vector before preparing further constructs with it.

TABLE 1

| Primer name | 5' Primer sequence 3' |
|---|---|
| EMCVF(AscI).2 | TGGCGCGCCGCTCGGAATTCCCCCTCTCCC (SEQ ID NO:8) |
| EMCVR(AscI).1 | AGGCGCGCCTTCTATGTAAGCAGCTTGCC (SEQ ID NO:9) |
| F'-CAT(BamHI) | GCTGGATCCATGGAGAAAAAAATCACTGGA (SEQ ID NO:10) |
| R'-CAT(XbaI) | CGATCTAGATTACGCCCCGCCCTGCCACTCA (SEQ ID NO:11) |
| Anti-En(EcoRI) | CGGAATTCATTATCATCGTGTTTTC (SEQ ID NO:12) |
| Anti-EN(BamHI) | CGGGATCCCCCCTAACGTTACTGGCCGAAGC (SEQ ID NO:13) |
| Anti-En(AscI) | AGGCGCGCCATTATCATCGTGTTTTC (SEQ ID NO:14) |
| dAvr En(AscI)R | AGGCGCGCCCTAGGGGTCTTTCCCCTCTC (SEQ ID NO:15) |
| 3'UTR4Xbiotin | GCGGCATGCCAATCGCCGCGAGTTCTATGTAAGCAGCTTGCC (SEQ ID NO:16) |
| GAG-F | CGGGATCCATGGCTGCGAGAGCGTCA (SEQ ID NO:17) |
| GAG-R | CGGGATCCTTATTGAGACAAGGGGTCGC (SEQ ID NO:18) |

B. XIAP IRES-Containing Vectors

The X-linked inhibitor of apoptosis (XIAP) gene 5' non-coding region (NCR) containing the putative IRES element (see Holcik et al. (1999) *Nature Cell Biol* 1: 190-192; Holcik and Korneluk (2000) *Mol Cell Biol* 20: 4648-57 and Holcik et al. (2003) *Mol Cell Biol* 23: 280-288 for sequence and size of element) was PCR amplified from human fetal liver marathon ready cDNA (Clontech, Palo Alto, Calif.) using an adaptor primer supplied with the cDNA and an XIAP reverse primer (XIAP-R) followed by a nested PCR using XIAP IRES specific primers. Primers are listed in Table 2. Resulting PCR products of approximately 1007 and 241 bp were TA cloned using a commercially available kit (Invitrogen Corporation; Carlsbad, Calif.). These constructs possess either 844 nucleotides or 78 nucleotides, respectively, of the XIAP gene non-coding region, in addition to the 163 nucleotide putative XIAP IRES. Sequences for each construct were confirmed by automated DNA sequencing. To generate shuttle vectors for cloning into the VEE replicon, the XIAP sequences were transferred as an EcoRI fragment into the equivalent site of pKS-rep2, generating pKS-rep2/XIAP1007 and pKS-rep2/XIAP241 DNAs.

TABLE 2

| | |
|---|---|
| XIAP-R | 5'-CCCTGCTCGTGCCAGTGTTGATGC-3' (SEQ ID NO:19) |
| XIAP/IRES-1007 | 5'-ACACGTGGGGCAACCCTGATTTATGCCTGTTGTCC-3' (SEQ ID NO:20) |
| XIAP/IRES-241 | 5'-AGTTAACTCAAAAAGAGAAAACAAAAATGC (SEQ ID NO:21) |
| XIAP/IRES-R | 5'-AGATATCTTCTCTTGAAAATAGGACTTGTCCAC-3' (SEQ ID NO:22) |
| Cap5'F | 5'-GTTCCCGTTCCAGCCAATGTATCCG-3' (SEQ ID NO:23) |
| 13-87pr1 | 5'-GTCACTAGTGACCACCATGT-3' (SEQ ID NO:24) |
| 3-1.1pr1 | 5'-TAAGAGCCGCGAGCGATCCT-3' (SEQ ID NO:25) |

```
1007 bp XIAP 5'NCR (SEQ ID NO:26)
ACACGTGGGGCAACCCTGATTTATGCCTGTTGTCCCAGTGTGATTATTAC
TAGTGTAATTTTTCACTTTGAGAAGTGTCCAGGTTTGGAGGATAAATTAT
CTTTCTAATAATTGATACCCTTCTCATAACCTAACGGGTTCCTTTTAGTA
TTTTATCTGGGTTAAAATTACCAGCTGTAATTTGGCAGCTCTAATAAGAC
TGCAGCAATACTTATCTTCCATTTGAACAGATTGTTACTTGACCAAGGGA
AGTTAATAGCAAAAGTAACTGCAGGGCACATGTATGTCATGGGCAAAAAA
AAAAAAGTAACAGCAATTAAGGTTTGCAGGTACTTAGAATTTTTCCTGAG
CCACCCTCTAGAGGGCAGTGTTACATATATATCTGTAATTATCCAGTTAC
AACAAAAAAAGGGCTCTCATTCATGCATGAAAATCAGAAATATTTCATAC
TCTTAAAGAACACATTGGAACCAATATTATGATTAAAACATATTTTGCTA
AGCAAAGAGATATTAAAAATTAATTCATTAACATTCTGAACATTTTTTAA
CTTGTAAAAACAACTTTGATGCCTTGAATATATAATGATTCATTATAACA
ATTATGCATAGATTTTAATAATCTGCATATTTTATGCTTTCATGTTTTTC
CTAATTAATGATTTGACATGGTTAATAATTATAATATATTCTGCATCACA
GTTTACATATTTATGTAAAATAAGCATTTAAAAATTATTAGTTTTATTCT
GCCTGCTTAAATATTACTTTCCTCAAAAAGAGAAAACAAAAATGCTAGAT
TTTACTTTATGACTTGAATGATGTGGTAATGTCGAACTCTAGTATTTAGA
ATTAGAATGTTTCTTAGCGGTCGTGTAGTTATTTTTATGTCATAAGTGGA
TAATTTGTTAGCTCCTATAACAAAAGTCTGTTGCTTGTGTTTCACATTTT
GGATTTCCTAATATAATGTTCTCTTTTTAGAAAAGGTGGACAAGTCCTAT
TTTCAAGAGAAGAT
```

Example 2

Construction of Improved Replicon Vectors

A. Constructs Containing the EMCV IRES

To demonstrate the functionality of an IRES sequence placed downstream of a functional alphavirus 26S promoter, reporter genes were subcloned into the pCDNA3.3/EMCV transfer vector and then the EMCV/reporter gene cassette was moved into the pERK replicon vector. Initial experiments were conducted using a replicon vector expressing the Chloramphenicol acetyl transferase (CAT) reporter gene. The CAT gene was amplified using primers F'-CAT (BamHI) and R'-CAT (XbaI)(Table 1). The PCR product was digested with BamHI and XbaI restriction enzymes and ligated into BamHI/XbaI linearized pCDNA3.3/EMCV DNA, generating pCDNA3.3/EMCV/CAT. After the sequence of the CAT gene was confirmed, pCDNA3.3/EMCV/CAT DNA was digested with AscI restriction enzyme to release a 1303 bp EMCV/CAT fragment. The AscI digested EMCV/CAT fragment was then ligated into AscI linearized pERK vector DNA, generating pERK/EMCV/CAT.

It has been shown that the EMCV IRES has a directional activity and when it is in the wrong orientation, with regard to a NOI, no cap-independent translation is noted (Roberts and Belsham (1997) *Virology* 227: 53-62). In addition, deletion of the 5' terminal sequences of the EMCV IRES abolishes cap-independent translation in the context of a dicistronic expression vector (Van der Velden et al. (1995) *Virology* 214: 82-90; Jang & Wimmer (1990) *Genes & Development* 4: 1560-72). To demonstrate that cap-independent translation of the CAT gene is occurring, two pERK vectors identical to pERK/EMCV/CAT were prepared, only with the EMCV IRES in the anti-sense orientation (pERK/anti-EMCV/CAT) or with a 5' deletion of the terminal sequences of the EMCV IRES (pERK/ΔAvr/CAT).

An anti-sense version of the EMCV IRES was PCR amplified from pKS rep2/EMCV DNA using primers anti-En (EcoRI) and anti-En(BamHI)(Table 1). The amplified EMCV IRES fragment was digested with EcoRI and BamHI restriction enzymes and ligated into EcoRI/BamHI linearized pKS-rep2 DNA, generating pKS-rep2/anti-EMCV. The BamHI/XbaI digested CAT gene described above, was ligated into BamHI/XbaI linearized pKS-rep2/anti-EMCV DNA, generating pKS-rep2/anti-EMCV/CAT. The 1295 bp anti-EMCV/CAT gene cassette was PCR amplified from pKS-rep2/anti-EMCV/CAT DNA using primers EMCVR(AscI).1 and anti-En(AscI) (Table 1). Finally, the anti-EMCV/CAT fragment was digested with AscI restriction enzyme and ligated into AscI linearized pERK vector DNA, generating pERK/anti- EMCV/CAT. The sequence of the anti-EMCV/CAT gene region was confirmed before further experiments were carried out.

To generate the ΔAvr/CAT pERK vector, first the ΔAvr deletion was made in the EMCV IRES found in pKS-rep2/EMCV intermediate vector. The deletion was accomplished by digesting pKS-rep2/EMCV DNA with both EcoRI and AvrII restriction enzymes deleting 145 bp from the 5' region of the EMCV IRES. The linearized DNA was treated with T4 DNA polymerase to create blunt ends and religated to generate pKS-rep2/ΔAvr DNA. The CAT gene was cloned into the intermediate vector by ligating the BamHI/XbaI CAT gene described above into BamHI and XbaI restriction enzyme linearized pKS-rep2/ΔAvr, generating pKS-rep2/ΔAvr/CAT DNA. The 1177 bp ΔAvr/CAT gene cassette was PCR amplified from pKS-rep2/ΔAvr/CAT. DNA using primers EMCVR (AscI).1 and dAvr En(AscI) R (Table 1). Finally, the ΔAvr/CAT fragment was digested with AscI restriction enzyme and ligated into AscI linearized pERK vector DNA, generating pERK/ΔAvr/CAT. The sequence of the ΔAvr/CAT gene region was confirmed before further experiments were carried out.

B. Constructs Containing the EV71 IRES

The human enterovirus 71 (EV71) IRES element (Thompson and Sarnow (2003) *Virology* 315: 259-266) was cloned in both sense and antisense orientations into spacer replicon vectors and analyzed for expression of a CAT reporter gene. The EV71 IRES element (strain 7423/MS/87) was PCR amplified from pdc/MS DNA (Thompson and Sarnow, 2003) using primers to produce a sense fragment (dc/MS (EcoRI) F and dc/MS (BamHI)R) and an antisense fragment (dc/anti-MS (EcoRI) R and dc/anti-MS (BamHI)F) (Table 3). The sense and antisense EV71-MS IRES PCR products were digested with EcoRI and BamHI restriction enzymes and ligated into pCDNA3.3 (see Example 1) linearized with EcoRI and BamHI, generating pCDNA3.3/MS and pCDNA3.3/anti-MS. The EV71-MS IRES regions, in each pCDNA3.3 vectors, were sequenced to verify that no nucleotide changes were introduced during PCR amplification before further experiments were initiated.

The CAT reporter gene, as described above in A., was cloned into BamHI and XbaI linearized pCDNA3.3/MS and pCDNA3.3/anti-MS vectors, generating pCDNA3.3/MS/CAT and pCDNA3.3/anti-MS/CAT, respectively. Spacer replicon constructs were produced by digesting the pCDNA3.3/MS/CAT and pCDNA3.3/anti-MS/CAT DNAs with AscI restriction enzyme and ligating the MS-CAT or anti-MS-CAT AscI fragments into spacer replicon vectors. The spacer-IRES-CAT region of each vector, was sequenced to verify that no nucleotide changes were introduced during cloning before further experiments were initiated.

TABLE 3

| Primer | Sequence 5'-3' |
|---|---|
| dc/MS(EcoRI)F | CGAATTCTTAAAACAGCTGTGGGTTG (SEQ ID NO:27) |
| dc/MS(BamHI)R | CGGGATCCGGTCAACTGTATTGAGGGTTAATA TAAAG (SEQ ID NO:28) |
| dc/anti-MS (BamHI)F | CGGGATCCTTAAAACAGCTGTGGGTTGTTCCC AC (SEQ ID NO:29) |
| dc/anti-MS (EcoRI)R | GGAATTCGGTCAACTGTATTGAGGGTTAATAT AAAG (SEQ ID NO:30) |

C. Constructs Containing the XIAP IRES

The CAT gene was cloned into the EcoRV and BamHI sites of pKS-rep2/XIAP1007 (see Example 4 below) after PCR amplification of the gene using CATF (5'-GGAGAAAAAAATCACTGGATATAC-3', SEQ ID NO:31) and CATR(Bam) (5'-GGGGATCCTTACGCCCCGCCCT-GCCAC-3', SEQ ID NO:32) primers, generating pKS-rep2/XIAP/CAT 1007. This strategy reconstitutes the wild-type XIAP gene start site. The intermediate was then cloned as an ApaI/SphI fragment into pERK to generate pERK/XIAP/CAT 1007. Following in vitro transcription and electroporation into Vero cells, VRP yields and CAT protein expression in infected cells were determined and compared to pERK/EMCV/CAT 342. VRP yields were equivalent for both constructs. In this particular construct, it has been possible to modify the level of CAT protein expression using the XIAP IRES (3.97 e5 ng/μg) as compared with the EMCV IRES (1.08 e6 ng/μg), thus demonstrating the utility of different IRESs in the claimed invention.

D. Constructs Expressing HIV gp160

A replicon expressing the HIV gp160 clade C gene was constructed in which translation of the HIVgp 160 was directed from the EMCV IRES. In this construct, the 167 bp spacer from the pH 1500A/EMCV/Vcap helper construct (see Example 4.B.1.) was cloned into an EMCV IRES replicon construct as follows. The pH 1500A/EMCV/Vcap DNA was digested with ApaI restriction enzyme to release a 194 bp fragment containing the 167 bp spacer and a portion of the EMCV IRES. A pERK/EMCV 749 vector was also digested with ApaI restriction enzyme and the released 749 bp spacer ApaI fragment was replaced with the 167 bp spacer ApaI fragment, generating the pERK/EMCV 167 vector. To demonstrate that a heterologous gene could also be efficiently expressed and packaged from the pERK/EMCV 167 replicon vector, the HIV clade C gp160 gene (Williamson C et al. (2003) AIDS Res Hum Retroviruses 19: 133-44) was cloned into this vector as follows. The HIV gp160 gene was amplified (using primers env-5'-XbaI and DU151gp160 3'-XbaI) (Table 4) and cloned into pCR-XL-TOPO (Invitrogen, Carlsbad, Calif.), generating pCR-XL-TOPO/gp160. The gp160 gene was sequenced to ensure no errors were introduced during PCR amplification before initiating further studies. The pCR-XL-TOPO/gp160 DNA was digested with XbaI restriction enzyme and the gp160 fragment was then ligated into XbaI linearized pCDNA3.3/EMCV, generating pCDNA3.3/EMCV/gp160. The pCDNA3.3/EMCV/gp160 DNA was digested with AscI restriction enzyme to release the EMCV/gp 160 fragment. The EMCV/gp160 fragment was then ligated into AscI linearized pERK/EMCV 167 vector DNA, generating the pERK/EMCV/gp160 167 vector.

TABLE 4

| Primer | Sequence 5'-3' |
|---|---|
| Env-5'-XbaI | CGACATAGTCTAGACCGCCAAGATGAGAGTGATGG (SEQ ID NO:33) |
| DU151gp1603'-XbaI | GATCTCTAGATTATTGCAAAGCTGCTTCAAAGCCC (SEQ ID NO:34) |

E. Construction of Double Subgenomic IRES Replicons Expressing Multiple NOIs

An IRES replicon vector coding for two 26S-spacer-IRES-NOI cassettes in series was constructed. The base pERK vector used to generate the double subgenomic IRES replicons (pERK MCS2) contained a 342 bp spacer region downstream of the 26S promoter and coded for the following restriction sites in its MCS (5' AscI, SnaBI, SphI 3').

The C-terminal portion of the heavy chain (Hc) of botulinum neurotoxins A and B (BoNT A and BoNT B) was cloned into pCDNA3.3/EMCV as BamHI/XbaI fragments, generating pCDNA3.3/EMCV/BoNT A and pCDNA3.3/EMCV/BoNT B, respectively. The BoNT genes were digested out of the pCDNA3.3/EMCV vectors with AscI restriction enzyme and the AscI EMCV/BoNT cassettes were ligated into AscI linearized pERK MCS2 DNA, generating pERK/BoNT A MCS2 and pERK/BoNT B MCS2 monovalent vectors. Orientation of the insert was determined by restriction analysis and clones with inserts in the sense orientation were isolated. The EMCV IRES and BoNT genes were sequenced to verify that no errors were introduced during cloning before further experiments were initiated.

To generate the double subgenomic BoNT A/B IRES replicon construct (pERK-BoNT A/B MCS2) the monovalent pERK BoNT MCS 2 vectors were utilized. The pERK/BoNT B MCS2 vector was partially digested with PspOM I restriction enzyme and the ends were made blunt using T4 DNA polymerase. The pERK/BoNT B MCS2 DNA was further digested with SphI restriction enzyme to release a 26S-342 bp spacer-EMCV-BoNT B fragment. The 26S-342 bp spacer-EMCV-BoNT B fragment was then ligated into SnaBI/SphI digested pERK/BoNT A MCS2 DNA, generating the pERK-BoNT A/B MCS2 vector. The final structure of the construct is 5' NCR-nsP1,2,3,4-26S-342 bp spacer-EMCV-BoNT A-26S-342 bp spacer-EMCV-BoNT B-NCR 3'. The sequence of the double subgenomic IRES replicon was verified before expression and VRP packaging studies were conducted.

F. Construction of an IRES-Containing S.A. AR86 Replicon

A replicon vector derived from S.A.AR86 (pRep89; described in Heise et al. *J Virol.* 2003 77(2): 1149-56) was modified to contain a 342 bp spacer-EMCV-HIV gag cassette downstream of the 26S promoter. The 342 bp spacer-EMCV-HIV gag fragment was PCR amplified from pERK/EMCV/gag 342 DNA using primer stuffer 342 (ClaI) and 3-42.pr4 (Table 5). Amplification with the 3-42.pr4 primer allows incorporation of 3' ClaI site that exists just downstream from the HIV gag gene in the pERK/EMCV/gag 342 DNA. The PCR product was then digested with ClaI restriction enzyme and ligated into ClaI linearized pRep89, generating the pRep89/EMCV/gag 342 vector. The entire inserted region was sequenced to ensure that no errors had been introduced during PCR amplification.

TABLE 5

| Primer | Sequence 5'-3' |
|---|---|
| stuffer 342 (ClaI) | CCATCGATCTATTCCAGAAGTAGTGAGG (SEQ ID NO:35) |
| 3-42.pr4 | CAATCGCCGCGAGTTCTATG (SEQ ID NO:36) |

Example 3

NOI Expression Analysis from IRES-Directed Replicons

A. EMCV IRES Replicon Expression

1. CAT Expression

CAT protein expression was examined using the pERK/EMCV/CAT. pERK/anti-EMCV/CAT, and pERK/ΔAvr/CAT replicon constructs. Capped replicon RNAs were in vitro transcribed using a T7 RiboMax kit (Promega Corporation; Madison, Wis.; Cat No. P1300). RNAs were purified using RNeasy purification columns (Qiagen Corporation, Germantown, Md.) following the manufacturers instructions. Vero cells (6×10$^6$ cells) suspended in 0.4 ml InVitrus™ chemically defined cell culture medium, (Cell Culture Technologies GmbH, Zurich, CH; Catalog No. IVT) and electroporated with 15 μg of either pERK/EMCV/CAT or pERK/anti-EMCV/CAT RNA using a Bio Rad Gene Pulser (BioRad Laboratories, Hercules, Calif.). Cells were pulsed four times with the electroporator set at 290 volts and 25 microfarads. CAT expression was detected by IFA using a rabbit anti-CAT antibody on methanol fixed cells and by ELISA using electroporated cell lysates and a commercially available CAT ELISA kit (Boehringer Mannheim, Indianapolis, Ind.).

Random DNA fragments were cloned between the EMCV IRES sequence and the VEE subgenomic promoter at a unique EcoRV site located in the pERK vectors. The small DNA fragments cloned between the 26S promoter and the EMCV IRES came from AluI restriction enzyme digested pCDNA3.1 (−) DNA. The AluI restriction enzyme cuts frequently within pCDNA3.1(−) DNA resulting in blunt end fragments ranging in size from 706 bp to 6 bp. The AluI digested pCDNA3.1 (−) fragments were ligated into EcoRV linearized pERK/EMCV/CAT, pERK/anti-EMCV/CAT, and pERK/ΔAvr/CAT DNAs. Individual clones were sequenced to determine what spacer fragment had been cloned into each new vector. The size of some of the spacer fragments found in the vectors was larger than the largest predicted pCDNA3.1 (−) AluI fragment, due to ligation of multiple fragments into the spacer region of these replicons. Each spacer-IRES replicon was transcribed and the RNA electroporated into Vero cells as described above. CAT protein expression was monitored by CAT ELISA and the results are summarized in Table 6.

TABLE 6

CAT expression analysis from EMCV-IRES containing replicons

| Replicon | size of spacer fragment | ng CAT/μg total protein |
|---|---|---|
| pERK/anti-EMCV/CAT | 133 | 2.1 |
| pERK/EMCV/CAT | 234 | 9.9 |
| pERK/anti-EMCV/CAT | 234 | 1.5 |
| pERK/ΔAvr/CAT | 234 | 0.4 |
| pERK/ΔAvr/CAT | 226 | 0.5 |
| pERK/EMCV/CAT | 342 | 10.3 |
| pERK/anti-EMCV/CAT | 357 | 0.1 |
| pERK/EMCV/CAT | 805 | 7.4 |
| pERK/anti-EMCV/CAT | 706 | 0.5 |
| pERK/ΔAvr/CAT | 681 | 0.02 |

The results indicate that CAT expression from pERK/IRES/CAT replicon constructs containing spacer fragments is robust and directed by the IRES, as compared with similar vectors with no spacer fragments (approximately 4-7 ng CAT/μg total protein). The highest levels of expression of the heterologous gene occurred when spacer fragments greater than approximately 200 nucleotides were introduced between the 26S promoter and the EMCV IRES sequences.

2. Multiple NOI Expression from a Single Replicon

Expression and packaging of the pERK-BoNT A/B MCS2 replicon were carried out in Vero cells. Capped pERK-BoNT A/B replicon RNA was transcribed and purified as described above. Vero cells ($1 \times 10^8$ cells) were electroporated with 30 μg of replicon RNA, 30 μg of capsid helper RNA and 30 μg of glycoprotein helper RNA. Electroporated cells were analyzed by IFA using horse anti-BoNT A and BoNT B antibodies (Perimmune, Rockville, Md.) before VRP were harvested. Results of the IFA and titration of VRP generated are shown in Table 7.

TABLE 7

| Replicon | Anti-BoNT A IFA | Anti-BoNT B IFA | VRP titer |
|---|---|---|---|
| pERK-BoNT A/B MCS2 | Positive | Positive | $2 \times 10^9$ VRP |

3. HIV gp160 Expression

The pERK/EMCV/gp160 167 replicon (Example 2D) was analyzed for expression of the gp160 gene and VRP generation. Purified RNA was prepared for the replicon, GP helper and capsid helper as described above. Vero cells were electroporated with the RNAs and VRP were collected 20-24 hours post electroporation. Results of IFA and VRP titration are summarized in Table 8. For comparison, a pERK replicon expressing gp160 directly from the 26S promoter was also evaluated.

TABLE 8

| Replicon | Anti-gp160 IFA | VRP titer/ml |
|---|---|---|
| pERK/gp160 | Positive | $2.1 \times 10^8$ |
| pERK/EMCV/gp160 167 | Positive | $2.5 \times 10^8$ |

4. HIV GAG expression from a S.A. AR86Replicon pRep89/EMCV/gag 342 DNA was transcribed in vitro, using an SP6 RiboMax kit (Promega Corporation; Madison, Wis.; Cat No. P1280), to generate capped replicon RNA. RNA was purified using RNeasy purification columns (Qiagen Corporation, Gemantown, Md.) following the manufacturers' instructions. Vero cells ($1 \times 10^8$ cells) were electroporated with 30 ug of Rep89/EMCV/gag 342 RNA and then analyzed for Gag protein expression ~18 hr post electroporation. Anti-Gag IFA analysis of Rep89/EMCV/gag 342 electroporated cells was positive for Gag protein expression B. EV71-MS IRES Replicon Expression Expression of CAT protein from each EV71-MS containing replicon was carried out in Vero cells. Capped replicon RNA was transcribed and purified as described above. Vero cells ($2-3 \times 10^7$ cells) were electroporated with 30 μg of replicon RNA. Electroporated cells were analyzed by IFA using anti-CAT (Cortex Biochem, San Leandro, Calif.) and anti-VEE nsp2 antibodies (AlphaVax) approximately 18 hours post electroporation. In addition, CAT expression was monitored by ELISA as described above. Results of IFA and CAT ELISA comparing activity detected from pERK/EMCV/CAT 342 and pERK/MS/CAT 342 replicons are shown in Table 9.

TABLE 9

| Replicon | Anti CAT IFA | Anti VEE nsp2 IFA | ng CAT/μg protein | % reduction in translation |
|---|---|---|---|---|
| pERK/MS/CAT 342 | + | + | 20.1 | NA |
| pERK/anti-MS/CAT 342 | − | + | 0.6 | 97% |
| pERK/EMCV/CAT 342 | + | + | 14.8 | NA |
| pERK/ΔAvr/CAT 342 | − | + | 0.0 | >99% |

Example 4

IRES-Directed Translation with Different Spacers

A. Replicon Constructs

1. EMCV IRES-Containing Constructs

Pairs of replicon constructs coding for either the EMCV or antisense-EMCV IRES sequences were prepared that contained exactly the same spacer region. These comparisons demonstrate that only the EMCV IRES sequences in the sense-orientation (i.e. in the 5'-3' orientation in which the sequence is found in the virus) direct cap-independent translation; that is, very little translation occurs when the IRES is in an anti-sense orientation, indicating that a properly-oriented IRES element is required to obtain significant CAT expression in these constructs. These replicon constructs were prepared as described above. Each spacer-IRES replicon was in vitro transcribed and 30 μg of each purified RNA was electroporated into $1 \times 10^7$ Vero cells as described above. CAT protein expression was monitored by CAT ELISA and the results are summarized in Table 10.

TABLE 10

Comparison of CAT expression using spacer-EMCV or spacer-anti-EMCV IRES replicons.

| replicon | size of spacer fragment | ng CAT/ μg total protein | replicon | size of spacer fragment | ng CAT/ μg total protein | % reduction in translation* | Fold increase in translation# |
|---|---|---|---|---|---|---|---|
| EMCV/CAT | 257 | 16.9 | Anti-EMCV/CAT | 257 | 3.1 | 82.7 | 5.5 |
| EMCV/CAT | 342 | 35.6 | Anti-EMCV/CAT | 342 | 0.2 | 99.4 | 178 |

TABLE 10-continued

Comparison of CAT expression using spacer-EMCV or spacer-anti-EMCV IRES replicons.

| replicon | size of spacer fragment | ng CAT/ µg total protein | replicon | size of spacer fragment | ng CAT/ µg total protein | % reduction in translation* | Fold increase in translation# |
|---|---|---|---|---|---|---|---|
| EMCV/CAT | 357 | 7.6 | Anti-EMCV/CAT | 357 | 0.4 | 94.7 | 19 |
| EMCV/CAT | 383 | 28.7 | Anti-EMCV/CAT | 383 | 0.6 | 97.9 | 48 |
| EMCV/CAT | 579 | 40.0 | Anti-EMCV/CAT | 579 | 0.3 | 99.2 | 133 |
| EMCV/CAT | 749 | 6.74 | Anti-EMCV/CAT | 749 | 0.03 | 99.5 | 224 |

*% reduction in translation in the anti-sense oriented IRES constructs relative to the sense-oriented, IRES directed constructs
Fold increase in translation from the sense oriented IRES element relative to translation from constructs with an anti-sense oriented IRES element The data show that CAT protein expression was greatly reduced (in most cases >95%) when the replicon contained a spacer and an anti-sense EMCV IRES upstream of the CAT gene. Furthermore, the data demonstrate the capability of an IRES-directed protein expression system to optimize the level of expression of NOI. The optimization is NOI-specific, but utilizing the teachings herein, the identification of spacer-IRES combinations that provide the desired level of expression for any given NOI would be routine to one of ordinary skill in the art.

2. Use of a Spacer Derived from a 5' Non-Coding Region

A pERK replicon was engineered to contain the full-length VEE capsid protein gene by PCR amplifying the capsid sequence from pH500A/Vcap using the Cap5'F and 3-1.1pr1 primers (Table 11). The resulting PCR product was inserted into the EcoRV and SphI restriction enzyme sites of pERK. "pERK/Capsid," was modified further to contain a unique AscI restriction enzyme at the 3' end of the capsid gene using AscIF and AscIR primers (Table 11) for site-directed mutagenesis using a commercially available kit (Stratagene). Serial truncations of the VEE capsid sequence were then generated by PCR amplification of sequences from pERK/Capsid using a forward primer (13-82.2.16) that anneals within the nsP4 gene and reverse primers (Table 11), that have been engineered to contain an AscI restriction enzyme site. PCR products were digested with ApaI and AscI or SwaI and AscI and cloned back into pERK/Capsid to generate pERK/Cap200, pERK/Cap400 and pERK/Cap600. These replicons retain increasing amounts of sequence from the 5' end of the capsid gene to function as a "spacer" between the 26S promoter and the downstream constructs to be inserted. To introduce an EMCV/CAT cassette into each of the pERK/Cap vectors described above, pCDNA3.3/EMCV/CAT DNA was digested with AscI restriction enzyme to release a 1303 bp EMCV/CAT fragment. The AscI digested EMCV/CAT fragment was then ligated into the AscI linearized pERK/Cap vector DNAs, generating pERK/EMCV/CAT Cap 200, pER1/EMCV/CAT Cap 400 and pERK/EMCV/CAT Cap600.

TABLE 11

Primers for generating capsid spacer replicons.

| | |
|---|---|
| Cap5'F | 5'-GTTCCCGTTCCAGCCAATGTATCCG-3' (SEQ ID NO:37) |
| 3-1.1pr1 | 5'-TAAGAGCCGCGAGCGATCCT-3' (SEQ ID NO:38) |
| AscIF | 5'-CCGCGAGTTCTATGTAAGCGGCGCGCCAATTGTTACAGACACATGGTGG-3' (SEQ ID NO:39) |
| AscIR | 5'-CCACCATGTGTCTGTAACAATTGGCGCGCCGCTTACATAGAACTCGCGG-3' (SEQ ID NO:40) |
| 13-82.2.16 | 5'-GCTCTTTTTGCGAAGACACATAAT-3' (SEQ ID NO:41) |
| CAP200(AscI) | 5'-TTGGCGCGCCTTCTTCGGTTTCTTAGCGGATGGCCC-3' (SEQ ID NO:42) |
| CAP400(AscI) | 5'-TTGGCGCGCCCTTCCAACATGATTGGGAACG-3' (SEQ ID NO:43) |
| CAP600(AscI) | 5'-TTGGCGCGCCTGTAATAGCCTTGGGGTTTCTCATGGG-3' (SEQ ID NO:44) |

These replicons, containing portions of the 5' region of the VEE capsid gene, were linearized, in vitro transcribed, electroporated into Vero cells and analyzed for CAT protein expression by IFA and ELISA. CAT protein expression was verified by IFA using CAT-specific antibodies; however, the intensity of immunofluorescence varied depending on the length of the capsid gene spacer used. These results were reflected in the CAT ELISA (Table 12).

TABLE 12

Cat protein expression from replicons containing capsid gene spacers

| Construct | CAT IFA | nsP2 IFA | CAT Protein |
|---|---|---|---|
| pERK/EMCV/CAT Cap 200 | 75% | 95% | 29 ng/μg total prot. |
| pERK/EMCV/CAT Cap 400 | 60% | 95% | 2 ng/μg total prot. |
| pERK/EMCV/CAT Cap 600 | 60% | 95% | 5 ng/μg total prot. |
| pERK/EMCV/CAT 342 | 50% | 50% | 14 ng/μg total prot. |

B. Helper Constructs

1. Constructs Comprising the EMCV IRES

Helpers were constructed which individually expressed either the VEE glycoprotein genes ("GP") or the VEE capsid gene. Initially, two empty helper backbone vectors were generated to facilitate construction of spacer-IRES containing capsid and GP helpers. One empty helper was generated by digesting the pERK vector with ApaI and RsrII restriction enzymes to remove 6989 bp of the nonstructural protein coding region. The DNA was treated with T4 DNA polymerase to produce blunt ends before ligating the nonstructural gene-deleted pERK vector to produce pH500G. The pH500G empty helper contained approximately 500 nucleotides of the 5' noncoding region (NCR). The second empty helper was generated by digesting the pERK vector with SwaI and RsrII restriction enzymes to remove 6449 bp of the nonstructural protein coding region. The DNA was treated with T4 DNA polymerase to produce blunt ends before ligating the DNA, generating pH 1500G. The pH 1500G empty helper contained approximately 1500 nucleotides of the 5' NCR, including an additional 540 bp of the nsp4 gene immediately upstream of the 26S promoter that is not present in the pH500G helper. Empty helper constructs were also prepared that coded for an A rather than a G residue at nucleotide 3 (pH500A and pH1500A). These constructs were prepared by subcloning the 5' NCR region from a capsid helper (pH500A/Vcap), which contains an A at nucleotide 3, in place of the same region in pH500G and pH1500G. This was accomplished by digesting pH500A/Vcap with XbaI and SacI restriction enzymes, collecting the 430 bp fragment and ligating it into XbaI and SacI digested pH500G and pH1500G DNAs, generating pH500A and pH1500A respectively.

The capsid and GP genes were cloned into pCDNA3.3/EMCV and pKS-rep2/anti-EMCV as BamHI and XbaI fragments as described above. The EMCV/capsid, anti-EMCV/capsid, EMCV/GP and anti-EMCV/GP cassettes were cloned into the pH500G, pH500A, pH1500G and pH1500A empty helper constructs as AscI fragments as described above. The sequence of each helper was confirmed before further experiments were initiated.

Random spacer fragments were cloned between the 26S promoter and the EMCV or anti-EMCV IRES in each helper at a unique EcoRV site as previously described. The sequence and length of the inserted spacer fragments was determined for each new helper, and the length of the spacer insert is included at the end of the construct designation. Spacers #15, 16, and 22 were not further characterized. The constructs pH500A/EMCV/GP and pH500A/anti-EMCV/GP contain no spacer.

2. Packaging and Titers Using EMCV IRES-Containing GP and/or Capsid Helper Combinations Various combinations of the GP and Capsid helpers were used to package a VEE replicon expressing the HIV-GAG protein, pERK-342/EMCV/gag (see Example 7 for a description of the construction of this replicon). For the results presented in Table 13, 30 µg of each RNA helper and 30 µg of the replicon RNA were co-electroporated into Vero cells in a 0.8 ml electroporation cuvette, using 4 pulses at 580 V and 25 µF., and the cells were allowed to recover at room temperature for 10 min. Electroporated cells were seeded into T-175 flasks containing 50 ml EMEM (10% FBS) with antibiotics and incubated at 37° C. After 20-24 hours, VEE replicon particles ("VRPs") were collected and tittered on Vero cells in 96-well plates by measuring GAG protein expression using an immunofluorescence assay (IFA). The VRP yield (Table 13) from each electroporation is expressed on an "IU/ml" basis, for comparative purposes.

TABLE 13

| Capsid Helper | GP Helper | Yield of VRPs (IU/ml) |
|---|---|---|
| pH500A/EMCV/Vcap 384 | pH500A/EMCV/GP 393 | 1.6e6 |
| pH500A/EMCV/Vcap 291 | pH500A/EMCV/GP 393 | 1.32e6 |
| pH1500A/EMCV/Vcap 167 | pH500A/EMCV/GP 393 | 1.51e6 |
| pH500A/Vcap | pH500A/EMCV/GP 393 | 1.92e5 |
| pH500A/Vcap | pH500A/EMCV/GP #15 | 2.35e5 |
| pH500A/Vcap | pH500A/EMCV/GP #16 | 5.55e5 |
| pH500A/Vcap | pH500A/EMCV/GP #22 | 1.15e6 |
| pH500A/EMCV/Vcap 291 | pH500A/EMCV/GP 291 | 2.22e6 |
| pH1500A/EMCV/Vcap 167 | pH500A/EMCV/GP 291 | 5.16e6 |
| pH500A/Vcap | pH500A/EMCV/GP 291 | 1.75e5 |
| pH500A/EMCV/Vcap 291 | pH500A/EMCV/GP | 1.00e7 |
| pH1500A/EMCV/Vcap 167 | pH500A/EMCV/GP | 6.20e7 |
| pH500A/EMCV/Vcap 384 | pH500A/EMCV/GP 376 | 2.99e5 |
| pH500A/EMCV/Vcap 291 | pH500A/EMCV/GP 376 | 1.49e5 |
| pH1500A/EMCV/Vcap 167 | pH500A/EMCV/GP 376 | 1.71e5 |
| pH500A/Vcap | pH500A/EMCV/GP 376 | 8.53e4 |
| pH500A/EMCV/Vcap 384 | pH500A/EMCV/GP 342 | 8.11e5 |
| pH500A/EMCV/Vcap 291 | pH500A/EMCV/GP 342 | 8.32e5 |
| pH1500A/EMCV/Vcap 167 | pH500A/EMCV/GP 342 | 1.07e6 |
| pH500A/Vcap | pH500A/EMCV/GP 342 | 1.92e5 |
| pH500A/EMCV/Vcap 291 | pH500A/GP | 3.56e8 |
|  |  | 1.00e8 |
| pH1500A/EMCV/Vcap 167 | pH500A/GP | 1.13e8 |
|  |  | 2.37e7 |

In other experiments, the amount of GP Helper RNA was varied in the electroporation milieu; all other conditions for VRP production were as described above. The results are shown in Table 14.

TABLE 14

| Capsid Helper | GP Helper | µg GP RNA | VRP Yield (IU/ml) |
|---|---|---|---|
| pH500A/Vcap | pH500A/EMCV/GP 393 | 45 | 1.51e6 |
| pH500A/Vcap | pH500A/EMCV/GP 393 | 60 | 2.24e6 |

3. 26S-IRES GP Helpers Without a Spacer

This experiment was performed to see whether a spacer was required in the GP Helper to uncouple transcription from translation. Vero cells were separately electroporated with each of the following mixtures:

a. Gag Replicon Vector (see Ex. 6)+pH500A/anti-EMCV/GP+pH500A/anti-EMCV/Vcap 291 b. Gag Replicon Vector+pH500A/EMCV/GP+pH500A/EMCV/Vcap 291

Cells were incubated as described previously to allow VRP production and the VRPs were harvested and tittered on VERO cells by IFA. In the case of the helpers with the IRES in the sense orientation (the "b." mix), the VRP yield was 3.3 e6; while in the case of the helpers in which the IRES is placed in the anti-sense orientation, the VRP yield was 5.3 e2.

4. Production and Use of VEE Helper Constructs Containing the XIAP IRES

The VEE capsid ("VCap") and glycoprotein ("VGP") genes were PCR amplified from pH500A/Vcap and pH500A/GP, respectively, using PFU pol (Stratagene; LaJolla, Calif.) and Cap5'F or 13-87pr1 forward primers and 3-1.1pr1 reverse primers (Table 2, see Example 1B). The resulting PCR products were cloned into the EcoRV and SphI sites of pKS-rep2. This strategy reconstitutes the VEE structural protein start codon at the wild-type start of the XIAP gene. The VEE structural protein sequence in each plasmid was verified by automated DNA sequencing, and the resulting plasmids were used for in vitro transcription. RNA was purified using Qiagen RNeasy columns and electroporated into Vero cells for analysis of protein expression and packaging. All helpers expressed either VEE capsid or glycoproteins as determined by IFA, and titers recovered for a VEE replicon expressing the HIV GAG protein ranged from $1\times10^5$ to $1\times10^7$ total.

The XIAP1007-VEE structural protein construct described above was also cloned into a second helper plasmid, pH1500A, as an ApaI/SphI DNA fragment, generating pH1500A/XIAP/Vcap 1007 and pH1500A/XIAP/GP 1007. These plasmids were used to make RNA and electroporated into Vero cells as above to analyze protein expression and VRP packaging. Again, the resulting helpers expressed either the VEE capsid or glycoprotein as determined by IFA, and titers ranged from $1\times10^8$ to over $1\times10^9$ total VRP, demonstrating the gain from the transcription of the subgenomic mRNA from the 26S promoter.

Example 5

Northern analysis was carried out on total cellular RNA collected from Vero cells into which replicon RNAs were electroporated. Spacer-IRES replicon constructs were in vitro transcribed and 30 μg of RNeasy column-purified RNA was electroporated into approximately $1\times10^7$ Vero cells, as described above. The electroporated cells were resuspended in 10 ml of DMEM media, then 7 ml (approximately $7\times10^6$ cells) were seeded into one 25 cm$^2$ flask. Total cellular RNA was collected from the cells 16 hr post electroporation using an RNAwiz extraction kit (Ambion) following the manufacturers' instructions. The RNAs were quantified and 10 μg of each were run on a 1% glyoxal agarose gel before being transferred to a Brightstar-Plus membrane (Ambion) by passive transfer. The RNAs were UV crossliiked to the membrane, blocked with UltraHyb (Ambion) solution for 1 hr at 45° C., and probed overnight with UltraHyb solution containing a biotinylated anti-sense primer (3' UTR4Xbiotin, Table 1) specific for the 3' UTR of the VEE subgenomic RNA (Integrated DNA Technologies, Coralville, Iowa) 45° C. After overnight hybridization the blot was processed by chemiluminescent RNA detection using a Brightstar Biodetect kit (Ambion) following the manufacturers instructions and visualization with a Epi Chemi II Darkroom (UVP, Inc., Upland, Calif.). Results of Northern analysis of RNA from Vero cells electroporated with pERK/EMCV/CAT 257, pERK/anti-EMCV/CAT 257, pERK/EMCV/CAT 579, or pERK/anti-EMCV/CAT 579 is shown in FIG. 1. Both the EMCV and anti-EMCV replicon constructs produced subgenomic transcripts of nearly equal intensity, indicating that the lack of expression of CAT protein from spacer-anti-EMCV/CAT replicon constructs was not due to any substantive reduction in subgenomic RNAs.

Example 6

Construction of an HIV$_{gag}$ Gene IRES-Directed Replicon Vector

An HIV subtype C gag gene was cloned into the pERK/EMCV vector containing a 342 bp spacer (pERK-342), as described above. The gag gene was PCR amplified from pERK/HIV$_{gag}$ DNA using primers GAG-F and GAG-R (Table 1). The primers were engineered to contain BamHI restriction sites such that the PCR product would code for this site at the 5' and 3' ends. The PCR product was digested with BamHI restriction enzyme and ligated into BamHI linearized pCDNA3.3/EMCV DNA. Orientation of the gag gene was determined by restriction analysis and a construct with the gene in the correct orientation was selected, generating pCDNA3.3/EMCV/gag. The EMCV/gag gene cassette was digested from pCDNA3.3/EMCV/gag DNA with AscI restriction enzyme and ligated into AscI linearized pERK-342 DNA. Orientation of the EMCV/gag gene cassette was determined by restriction analysis and a construct with the gene in the correct orientation was selected, generating pERK-342/EMCV/gag. The sequence of the EMCV/gag region was verified before further experiments were initiated.

Analysis of gag protein expression, by IFA and Western blot, indicated that the protein expressed under the direction of the IRES in the pERK-342/EMCV/gag replicon is indistinguishable from the protein expressed from a pERK/HIV$_{gag}$ replicon in which both translation and transcription are directed by the 26S VEE subgenomic promoter. In addition, the level of expression, as measured by titering VRP, was increased with the IRES-directed system as compared to the 26S promoter-directed system (Table 15).

TABLE 15

Comparison of VRP titers generated with different replicon vectors

| Replicon vector | VRP titer |
|---|---|
| pERK/HIV$_{gag}$ | $4.0 \times 10^8$ IFU |
| pERK-342/EMCV/gag | $5.3 \times 10^8$ IFU |

Example 7

Humoral and Cellular Immune Responses in Mice Inoculated with IRES-Directed HIV Gag Replicon Particles The pERK/EMCV/gag 342 replicon elicits robust humoral and cellular responses when vaccinated into animals. Four-to-five week-old female BALB/c mice were obtained from Charles River and were acclimatized for one week prior to any procedure. For the prime and boost, groups of mice were inoculated in both rear footpads under isofluorane anesthesia with a target dose of $5\times10^5$ IFU of VRP in diluent containing PBS with 1% v/v human serum albumin and 5% w/v sucrose. Footpad injections were performed with a 30.5 G needle and a 0.100 mL Hamilton syringe by injecting 20 μL in each hind footpad. Serum samples were obtained by retro-orbital bleeding under isofluorane anesthesia before the first inoculation on Day 0 (pre-bleed), Day 21 (20 days after the primary inoculation) and Day 29 (7 days after the boost). The vaccination schedule is summarized in Table 16. Spleens were harvested 14 days after boost for IFN-γ ELISPOT assays

TABLE 16

IRES-directed replicon VRP vaccination schedule

| Group | N | Mouse strain | VRP Vaccine | Dose, IFU | Route | Inoculation Day | Serum Sampling Day |
|---|---|---|---|---|---|---|---|
| 1 | 5 | BALB/c | EMCV/Gag 342[2] | $5 \times 10^5$ | sc-fp[4] | Day 1 & 22 | Day 0, 21, 29 |
| 2 | 5 | BALB/c | EMCV/Gag 342[2] | $5 \times 10^5$ | sc-fp[4] | Day 1 & 22 | Day 0, 21, 29 |

TABLE 16-continued

IRES-directed replicon VRP vaccination schedule

| Group | N | Mouse strain | VRP Vaccine | Dose, IFU | Route | Inoculation Day | Serum Sampling Day |
|---|---|---|---|---|---|---|---|
| 3 | 5 | BALB/c | Control VRP[3] | $5 \times 10^5$ | sc-fp[4] | Day 1 & 22 | Day 0, 21, 29 |

[1]GMP manufactured Gag VRP prepared with un-modified pERK replicon vector
[2]342 refers to the number of nucleotides in the spacer upstream of the IRES/Gag cassette.
[3]Control VRP consist of replicons expressing an HIV Pol/Nef gene.
[4]sc-fp refers to subcutaneous footpad.

A. Immunologic Assays Performed After Vaccination

Gag ELISA: Purified recombinant histidine-tagged (his)-p55 from HIV-1 subtype C isolate DU-422 was used as antigen coat. Sera were evaluated for the presence of Gag-specific antibodies by a standard indirect ELISA.

Gag ELISPOT Assay: Viable lymphocytes harvested from spleens were seeded into individual ELISPOTassay wells in a Multiscreen Immobilon-P ELISPOT plate (ELISPOT certified 96-well filtration plate, Millipore, Bedford, Mass.) that had been pre-coated with an anti-IFN-γ monoclonal antibody AN18 (rat IgG1, MabTech, Mariemont, Ohio), and incubated for 16-20 hours. Cells were removed by multiple washes with buffer and the wells were incubated with a biotinylated anti-IFN-γ monoclonal antibody R4-6A2 (rat IgG1, MabTech), followed by washing and incubation with Avidin-Peroxidase-Complex (Vectastain ABC Peroxidase Kit, Vector Laboratories, Burlingame, Calif.). To allow for the complex to form, the Avidin-Peroxidase Complex was prepared at least 30 minutes before completion of the incubation period with the secondary antibody and was stored at room temperature. Following incubation, the wells were washed and incubated for 4 minutes at room temperature with substrate (AEC tablets, Sigma) to facilitate formation of spots, which represent the positions of the individual IFN-γ-secreting cells during culture. Spot development was stopped by distilled water rinse.

To enumerate Gag-specific IFN-γ secreting cells in lymphocytes from mice immunized with HIV$_{gag}$ VRP, lymphocytes were stimulated with the immunodominant CD8+ CTL H-2 K$^d$-restricted HIV-Gag peptide AMQMLKETI or an irrelevant HA (influenza hemagglutinin) CD8+ CTL H-2 K$^d$-restricted peptide IYSTVASSL that binds to MHC Class I, for 16-20 hours (5% $CO_2$ at 37° C.). Cells minus peptide serve as a background control. As a positive control, cells were stimulated with 4 μg/mL Conconavalin A for a similar time period. Peptides were synthesized with free ends and purified to >90% by New England Peptide.

HIV$_{gag}$ VRP Potency Titration: A Gag-specific IFA of HIV$_{gag}$ VRP infected Vero cells was used to measure the potency or infectious titer of the vaccines. Potency is measured as infectious units per mL, IFU/mL. On the day of each injection residual inocula were back-titrated to determine the actual dose each animal received (Table 17).

TABLE 17

Summary of Gag ELISA and ELISPOT results

| | | Inoculations Dose (IFU) | | Gag Ab Titers 7 Days Post | | | ELISPOT[1] (SFC/1e6 lymphocytes) |
|---|---|---|---|---|---|---|---|
| Mouse# | HIV VRP Vaccine | Prime Day 1 | Boost Day 22 | Pre-bleed Day −1 | Boost Day 29 | GMT[2] | 14 Days Post Boost Day 36 |
| 1-1 | EMCV/gag 342 | 6.8e5 | 4.4e5 | <40 | 20480 | 23525 | 341 |
| 1-2 | | | | <40 | 40960 | | |
| 1-3 | | | | <40 | 20480 | | 323 |
| 1-4 | | | | <40 | 20480 | | |
| 1-5 | | | | <40 | 20480 | | |
| 2-1 | EMCV/gag 342 | 1.2e6 | 5.6e5 | <40 | 5120 | 13512 | 438 |
| 2-2 | | | | <40 | 10240 | | |
| 2-3 | | | | <40 | 10240 | | 741 |
| 2-4 | | | | <40 | 20480 | | |
| 2-5 | | | | <40 | 40960 | | |
| 3-1 | control VRP | 2.8e5 | 2.2e5 | <40 | <40 | | 7 |
| 3-2 | | | | <40 | <40 | | |
| 3-3 | | | | <40 | <40 | | 46 |
| 3-4 | | | | <40 | ≧40 (OD = 0.32) | | |
| 3-5 | | | | <40 | ≧40 (OD = 0.32) | | |

[1]SFC/1e6 lymphocytes refers to spot forming cells per $1 \times 10^6$ lymphocytes
[2]GMT, geometric mean titer Results of the vaccination study indicate that the 342/EMCV/gag VRP vaccinated animals mounted a robust humoral and cellular immune response to HIV-Gag, as measured by anti-Gag antibody ELISA and Gag specific ELISPOT assays.

Example 8

The activity of several insect virus IRES sequences was compared to the activity of a mammalian-virus IRES (EMCV) in a number of insect cell lines. Replicon vectors were designed such that the 26S subgenomic transcript would be bi-cistronic. The 26S subgenomic RNA is capped, meaning that translation of the first gene on the bi-cistronic RNA (Chloramphenicol acetyl transferase (CAT)) is cap-dependent while translation of the second gene (luciferase (LUC)) is dependent on the IRES sequence (cap-independent). Sindbis virus-based replicon vectors were engineered to contain the following elements: 5'NCR, nsp1,2,3,4, 26S promoter, CAT gene, IRES, LUC gene, NCR 3'. Two insect virus IRES sequences, one derived from Acyrthosiphon pisum virus (APV) and the other from Rhopalosiphum padi virus (RhPV), were engineered between the CAT and LUC genes. For comparison, a mammalian virus IRES (EMCV) was engineered between the CAT and LUC genes into the same Sindbis replicon vector. RNA for each replicon construct and an RNA helper that coded for all of the Sindbis structural protein genes (capsid-E3-E2-6K-E1) were transcribed in vitro using SP6 RNA polymerase. Sindbis replicon particles were prepared by electroporating helper RNA and each of the bi-cistronic replicon RNAs into $8 \times 10^6$ BHK-21 cells. The media was collected, clarified, and replicon particles were purified by centrifugation through a 20% sucrose cushion (24,000 RPM for 3 hr at 4° C.). Replicon particles were titrated using a rabbit anti-CAT antibody (Cortex Biochem, San Leandro, Calif.).

To determine the activity of the insect virus IRES sequences in comparison to the EMCV IRES, the purified Sindbis replicon bi-cistronic particles were used to infect a number of different insect cells growing in culture. Insect cells used in these experiments were: Toxorhynchites amboinensis, Anopheles albimanus, Anopheles gambiae, and Aedes albopictus. Insect cells were infected at an MOI of 0.1 with replicon bi-cistronic particles. Approximately 16 hr post infection cell lysates were prepared and the amount of CAT protein present in the lysates was determined using a CAT ELISA kit (Roche, Indianapolis Ind.) following the manufacturers instructions. In parallel, the amount of LUC protein present in the lysates was determined using a luciferase assay kit (Roche). The amount of CAT and LUC detected in each lysate was normalized for the quantity of protein used in each assay to allow comparison of the two values (Table 18). The CAT protein detected in each cell type was similar regardless of the replicon used. This data indicates that similar infection efficiencies were attained within a cell type for each of the three IRES containing replicon particles, and thus the LUC activity detected in each cell type directly reflects the activity of the IRES sequence in that cell type. In each of the insect cell types analyzed, the insect-virus IRES had more activity (85-95% more) than the EMCV IRES (Table 18).

TABLE 17

Comparison of insect-virus IRES (APV or RhPV) activity and mammalian-virus IRES (EMCV) activity in different insect cell types.

| Insect cell type | IRES analyzed | ng CAT/µg protein | LUC activity (RLU)/µg protein | % difference from EMCV |
|---|---|---|---|---|
| Tox. amboinensis | APV | 2.0 | 290.5 | 88% |
| Tox. amboinensis | RhPV | 2.1 | 231.4 | 85% |

TABLE 17-continued

Comparison of insect-virus IRES (APV or RhPV) activity and mammalian-virus IRES (EMCV) activity in different insect cell types.

| Insect cell type | IRES analyzed | ng CAT/µg protein | LUC activity (RLU)/µg protein | % difference from EMCV |
|---|---|---|---|---|
| Tox. amboinensis | EMCV | 1.6 | 33.1 | 0% |
| An. Albimanus | APV | 2.9 | 497.7 | 93% |
| An. Albimanus | RhPV | 2.0 | 468.6 | 93% |
| An. Albimanus | EMCV | 2.3 | 31.8 | 0% |
| An. gambiae | APV | 1.8 | 525.7 | 95% |
| An. gambiae | RhPV | 1.7 | 283.6 | 91% |
| An. gambiae | EMCV | 1.8 | 24.2 | 0% |
| Ae. albopictus | APV | 4.8 | 87.3 | 93% |
| Ae. albopictus | RhPV | 4.1 | 119 | 95% |
| Ae. albopictus | EMCV | 4.7 | 5.7 | 0% |

Example 9

Humoral and Cellular Immune Responses to an IRES Replicon in Primates

A study on the immunogenicity of the pERK/EMCV/gag 342 containing VRPs (Example 6) was also conducted in cynomolgus macaques at the Southern Research Institute in Frederick. MD. Each vaccine was administered to six animals by subcutaneous and intramuscular injection (three animals/route). Animals received two inoculations of $1 \times 10^8$ vaccine particles at 0 and 1 month. Humoral immune responses were analyzed 4-weeks after the second inoculation (as described in Example 7A), and are presented in Table 19. For comparison, a VEE replicon expressing the gag protein directly from the 26S promoter (pERK/gag) was also evaluated.

TABLE 18

| Construct | Route | ELISA GMT |
|---|---|---|
| pERK/EMCV/gag 342 | Subcutaneous | 1613 |
| pERK/EMCV/gag 342 | Intramuscular | 640 |
| pERK/gag | Subcutaneous | 403 |
| pERK/gag | Intramuscular | 1280 |

Although the present process has been described with reference to specific details of certain embodiments thereof, it is not intended that such details should be regarded as limitations upon the scope of the invention except as and to the extent that they are included in the accompanying claims.

Throughout this application, various patents, patent publication, journal publications and other publications are referenced. The disclosures of these publications in their entireties are incorporated by reference into this application in order to more fully describe the state of the art to which this invention pertains and to provide written description for the subject matter of the sentence in which these references appear in this application.

What is claimed is:

1. A recombinant replicon nucleic acid comprising:
   a) a nucleic acid sequence encoding a 5' alphavirus replication recognition sequence;
   b) a nucleic acid sequence encoding an alphavirus nonstructural protein;
   c) an alphavirus subgenomic promoter-IRES-heterologous nucleic acid of interest (NOI) cassette, which is in the 5' to 3' orientation; and
   d) a nucleic acid encoding a 3' alphavirus replication recognition sequence.

2. The recombinant replicon nucleic acid of claim 1, wherein the nucleic acid sequence of (b) is a contiguous nucleotide sequence encoding alphavirus nonstructural proteins nsp1, nsp2, nsp3 and nsp4.

3. The recombinant replicon nucleic acid of claim 1, wherein the nucleic acid sequence of (b) is a contiguous nucleotide sequence encoding alphavirus nonstructural proteins nsp1, nsp2 and nsp3 and wherein the recombinant replicon nucleic acid comprises nucleotide sequence encoding alphavirus nonstructural protein nsp4 that is not contiguous with the nucleic acid sequence of (b).

4. The recombinant replicon nucleic acid of claim 1, wherein the IRES is selected from the group consisting of cellular IRESs, plant IRESs, mammalian virus IRESs, synthetic IRESs and insect virus IRESs.

5. The recombinant replicon nucleic acid of claim 1, wherein the alphavirus subgenomic promoter of (c) is a minimal or modified alphavirus subgenomic promoter.

6. The recombinant replicon nucleic acid of claim 1, wherein the heterologous NOI of (b) encodes a protein or peptide.

7. The recombinant replicon nucleic acid of claim 1, wherein the heterologous NOI is an antisense sequence.

8. The recombinant replicon nucleic acid of claim 1, wherein the heterologous NOI encodes a ribozyme.

9. The recombinant replicon nucleic acid of claim 1, further comprising a nucleotide sequence encoding an alphavirus structural protein.

10. The recombinant replicon nucleic acid of claim 9, wherein the alphavirus structural protein is from an alphavirus selected from the group consisting of Sindbis virus, SFV, VEE, S.A. AR86 virus, Ross River virus, EEE and WEE.

11. The recombinant replicon nucleic acid of claim 1, wherein the nucleic acid sequence of (a) is from an alphavirus selected from the group consisting of Sindbis virus, SFV, VEE, S.A. AR86 virus, Ross River virus, EEE and WEE.

12. The recombinant replicon nucleic acid of claim 1, wherein the nucleic acid sequence of (b) is from an alphavirus selected from the group consisting of Sindbis virus, SFV, VEE, S.A. AR86 virus, Ross River virus, EEE and WEE.

13. The recombinant replicon nucleic acid of claim 1, wherein the alphavirus subgenomic promoter of (c) is from an alphavirus selected from the group consisting of Sindbis virus, SFV, VEE, S.A. AR86 virus, Ross River virus, EEE and WEE.

14. The recombinant replicon nucleic acid of claim 1, wherein the nucleic acid sequence of (d) is from an alphavirus selected from the group consisting of Sindbis virus, SFV, VEE, S.A. AR86 virus, Ross River virus, EEE and WEE.

15. The recombinant replicon nucleic acid of claim 1, wherein the IRES of (c) directs the translation of the gene product encoded by the heterologous NOI of (c), such that at least 80% of the translation of the gene product encoded by the heterologous NOI is controlled by the activity of the IRES.

16. The recombinant replicon nucleic acid of claim 1, wherein the IRES of (c) directs the translation of the gene product encoded by the heterologous NOI of (c) such that at least 10% of the translation of the gene product encoded by the heterologous NOI is controlled by the activity of the IRES.

17. The recombinant replicon nucleic acid of claim 1, wherein the nucleic acid is RNA.

18. The recombinant replicon nucleic acid of claim 1, wherein the nucleic acid is DNA.

19. A recombinant replicon nucleic acid comprising:
   a) a nucleic acid sequence encoding a 5' alphavirus replication recognition sequence;
   b) a nucleic acid sequence encoding an alphavirus nonstructural protein;
   c) an alphavirus subgenomic promoter-IRES-heterologous nucleic acid of interest (NOI) cassette, said cassette further comprising a spacer non-coding nucleic acid 3' to the alphavirus subgenomic promoter and 5' to the IRES; and
   d) a nucleic acid encoding a 3' alphavirus replication recognition sequence.

20. The recombinant replicon nucleic acid of claim 19, wherein the spacer non-coding nucleic acid sequence is at least 30 nucleotides in length.

21. The recombinant replicon nucleic acid of claim 19, wherein the spacer non-coding nucleic acid sequence is between 25 and 7500 nucleotides in length.

22. The recombinant replicon nucleic acid of claim 19, wherein the spacer non-coding nucleic acid sequence is between 150 and 1000 nucleotides in length.

23. An alphavirus particle comprising the recombinant replicon nucleic acid of claim 1.

24. An alphavirus particle comprising the recombinant replicon nucleic acid of claim 19.

25. A population of infectious, defective, alphavirus particles, wherein each particle comprises the alphavirus particle of claim 23, and the population has no detectable replication-competent virus, as measured by passage on cell culture.

26. A population of infectious, defective, alphavirus particles, wherein each particle comprises the alphavirus particle of claim 24, and the population has no detectable replication-competent virus, as measured by passage on cell culture.

27. A pharmaceutical composition comprising the population of claim 25 in a pharmaceutically acceptable carrier.

28. A pharmaceutical composition comprising the population of claim 26 in a pharmaceutically acceptable carrier.

29. The alphavirus particle of claim 23, comprising an attenuating mutation.

30. The alphavirus particle of claim 24, comprising an attenuating mutation.

31. The recombinant replicon nucleic acid of claim 1, comprising an attenuating mutation.

32. The recombinant replicon nucleic acid of claim 19, comprising an attenuating mutation.

33. A population of infectious, defective, alphavirus particles, comprising the alphavirus particle of claim 23.

34. A population of infectious, defective, alphavirus particles, comprising the alphavirus particle of claim 24.

35. A composition comprising the population of claim 33, in a pharmaceutically acceptable carrier.

36. A composition comprising the population of claim 34, in a pharmaceutically acceptable carrier.

37. A method of making infectious, defective alphavirus particles, comprising:
   a) introducing into a cell the following:
      (i) the recombinant replicon nucleic acid of claim 1, and
      (ii) one or more helper nucleic acids encoding alphavirus structural proteins, wherein the one or more helper nucleic acids produce all of the alphavirus structural proteins; and
   b) producing the alphavirus particles in the cell.

38. The method of claim 37, wherein the recombinant replicon nucleic acid further comprises a nucleotide sequence encoding an alphavirus structural protein.

39. The method of claim 37, wherein the helper nucleic acid is a recombinant nucleic acid comprising a 5' alphavirus replication recognition sequence, an alphavirus subgenomic promoter, a nucleic acid encoding an alphavirus structural protein and a 3' alphavirus replication recognition sequence.

40. The method of claim 37, wherein the helper nucleic acid is a recombinant nucleic acid comprising a promoter and nucleotide sequences encoding one or more alphavirus structural proteins.

41. The method of claim 40, wherein the helper nucleic acid is DNA.

42. The method of claim 41, wherein the promoter is a CMV promoter.

43. The method of claim 41, wherein the helper nucleic acid comprises nucleotide sequences encoding all of the alphavirus structural proteins.

44. The method of claim 37, wherein the helper nucleic acid is a recombinant nucleic acid comprising a 5' alphavirus replication recognition sequence, an IRES element, a nucleotide sequence encoding an alphavirus structural protein and a 3' alphavirus replication recognition sequence.

45. A recombinant nucleic acid comprising:
   a) a 5' alphavirus replication recognition sequence;
   b) an alphavirus subgenomic promoter-IRES-heterologous NOI cassette, which is in the 5' to 3' orientation, wherein the NOI encodes one or more alphavirus structural proteins; and
   c) a 3' alphavirus replication recognition sequence.

46. A method of making infectious, defective alphavirus particles, comprising:
   a) introducing into a cell the following:
      i) the recombinant replicon RNA of claim 1; and
      ii) one or more helper nucleic acids encoding alphavirus structural proteins, wherein the helper nucleic acid(s) comprise a recombinant nucleic acid comprising:
         a) a 5' alphavirus replication recognition sequence;
         b) an alphavirus subgenomic promoter-IRES-heterologous NOI cassette, which is in the 5' to 3' orientation, wherein the NOI encodes one or more alphavirus structural proteins;
         c) and a 3' alphavirus replication recognition sequence, whereby all of the alphavirus structural proteins are produced in the cell; and
   b) producing the alphavirus particles in the cell.

47. A method of making infectious, defective alphavirus particles, comprising:
   a) introducing into a cell the following:
      i) an alphavirus replicon RNA comprising a 5' alphavirus replication recognition sequence, nucleic acid sequence(s) encoding alphavirus nonstructural proteins, an alphavirus subgenomic promoter, a heterologous nucleic acid sequence and a 3' alphavirus replication recognition sequence; and
      ii) one or more helper nucleic acids encoding alphavirus structural proteins, wherein the helper nucleic acid(s) comprise the recombinant nucleic acid of claim 45, whereby all of the alphavirus structural proteins are produced in the cell; and
   b) producing the alphavirus particles in the cell.

48. An isolated cell comprising the recombinant nucleic acid of claim 45.

49. The recombinant replicon nucleic acid of claim 1, further comprising an alphavirus packaging signal.

50. The recombinant replicon nucleic acid of claim 19, further comprising an alphavirus packaging signal.

51. A recombinant nucleic acid comprising:
   a) a 5' alphavirus replication recognition sequence;
   b) an alphavirus subgenomic promoter-IRES-heterologous NOI cassette, said cassette further comprising a spacer non-coding nucleic acid 3' to the alphavirus subgenomic promoter and 5' to the IRES, wherein the NOI encodes one or more alphavirus structural proteins;
   c) and a 3' alphavirus replication recognition sequence.

52. A method of eliciting an immune response in a subject, comprising administering to the subject an immunogenic amount of the population of claim 25.

53. A method of eliciting an immune response in a subject, comprising administering to the subject an immunogenic amount of the population of claim 26.

54. A method of eliciting an immune response in a subject, comprising administering to the subject an immunogenic amount of the composition of claim 27.

55. A method of eliciting an immune response in a subject, comprising administering to the subject an immunogenic amount of the composition of claim 28.

56. A recombinant replicon nucleic acid comprising:
 a) a nucleic acid sequence encoding a 5' alphavirus replication recognition sequence;
 b) a nucleic acid sequence encoding an alphavirus nonstructural protein;
 c) a first alphavirus subgenomic promoter-IRES-heterologous NOI cassette, which is in the 5' to 3' orientation;
 d) a second alphavirus subgenomic promoter-IRES-heterologous NOI cassette, which is in the 5' to 3' orientation; and
 e) a nucleic acid encoding a 3' alphavirus replication recognition sequence.

57. The recombinant replicon nucleic acid of claim 56, further comprising an alphavirus packaging signal.

58. A recombinant replicon nucleic acid comprising:
 a) a nucleic acid sequence encoding a 5' alphavirus replication recognition sequence;
 b) a nucleic acid sequence encoding an alphavirus nonstructural protein;
 c) a first alphavirus subgenomic promoter-IRES-heterologous NOI cassette, said cassette further comprising a first spacer non-coding nucleic acid 3' to the alphavirus subgenomic promoter and 5' to the IRES;
 d) a second alphavirus subgenomic promoter-IRES-heterologous NOI cassette, said cassette further comprising a first spacer non-coding nucleic acid 3' to the alphavirus subgenomic promoter and 5' to the IRES; and
 e) a nucleic acid encoding a 3' alphavirus replication recognition sequence.

59. The recombinant replicon nucleic acid of claim 19, wherein the nucleic acid sequence of (b) is a contiguous nucleotide sequence encoding alphavirus nonstructural proteins nsp1, nsp2, nsp3 and nsp4.

60. The recombinant replicon nucleic acid of claim 19, wherein the nucleic acid sequence of (b) is a contiguous nucleotide sequence encoding alphavirus nonstructural proteins nsp1, nsp2 and nsp3 and wherein the recombinant replicon nucleic acid comprises a nucleotide sequence encoding alphavirus nonstructural protein nsp4 that is not contiguous with the nucleic acid sequence of (b).

61. The recombinant replicon nucleic acid of claim 19, wherein the IRES is selected from the group consisting of cellular IRESs, plant IRESs, mammalian virus IRESs, synthetic IRESs and insect virus IRESs.

62. The recombinant replicon nucleic acid of claim 19, wherein the alphavirus subgenomic promoter of (c) is a minimal or modified alphavirus subgenomic promoter.

63. The recombinant replicon nucleic acid of claim 19, wherein the heterologous NOI of (b) encodes a protein or peptide.

64. The recombinant replicon nucleic acid of claim 19, wherein the heterologous NOI is an antisense sequence.

65. The recombinant replicon nucleic acid of claim 19, wherein the heterologous NOI encodes a ribozyme.

66. The recombinant replicon nucleic acid of claim 19, further comprising a nucleotide sequence encoding an alphavirus structural protein.

67. The recombinant replicon nucleic acid of claim 66, wherein the alphavirus structural protein is from an alphavirus selected from the group consisting of Sindbis virus, SFV, VEE, S.A. AR86 virus, Ross River virus, EEE and WEE.

68. The recombinant replicon nucleic acid of claim 19, wherein the nucleic acid sequence of (a) is from an alphavirus selected from the group consisting of Sindbis virus, SFV, VEE, S.A. AR86 virus, Ross River virus, EEE and WEE.

69. The recombinant replicon nucleic acid of claim 19, wherein the nucleic acid sequence of (b) is from an alphavirus selected from the group consisting of Sindbis virus, SFV, VEE, S.A. AR86 virus, Ross River virus, EEE and WEE.

70. The recombinant replicon nucleic acid of claim 19, wherein the alphavirus subgenomic promoter of (c) is from an alphavirus selected from the group consisting of Sindbis virus, SFV, VEE, S.A. AR86 virus, Ross River virus, EEE and WEE.

71. The recombinant replicon nucleic acid of claim 19, wherein the nucleic acid sequence of (d) is from an alphavirus selected from the group consisting of Sindbis virus, SFV, VEE, S.A. AR86 virus, Ross River virus, EEE and WEE.

72. The recombinant replicon nucleic acid of claim 19, wherein the IRES of (c) directs the translation of the gene product encoded by the heterologous NOI of (c), such that at least 80% of the translation of the gene product encoded by the heterologous NOI is controlled by the activity of the IRES.

73. The recombinant replicon nucleic acid of claim 19, wherein the IRES of (c) directs the translation of the gene product encoded by the heterologous NOI of (c) such that at least 10% of the translation of the gene product encoded by the heterologous NOI is controlled by the activity of the IRES.

74. The recombinant replicon nucleic acid of claim 19, wherein the nucleic acid is RNA.

75. The recombinant replicon nucleic acid of claim 19, wherein the nucleic acid is DNA.

76. An isolated cell comprising the recombinant replicon nucleic acid of claim 19.

77. An isolated cell comprising the recombinant replicon nucleic acid of claim 1.

78. An isolated cell comprising the recombinant nucleic acid of claim 51.

79. A method of making infectious, defective alphavirus particles, comprising:
 a) introducing into a cell the following:
  (i) the recombinant replicon nucleic acid of claim 19, and
  (ii) one or more helper nucleic acids encoding alphavirus structural proteins, wherein the one or more helper nucleic acids produce all of the alphavirus structural proteins; and
 b) producing the alphavirus particles in the cell.

80. The method of claim 79, wherein the recombinant replicon nucleic acid further comprises a nucleotide sequence encoding an alphavirus structural protein.

81. The method of claim 79, wherein the helper nucleic acid is a recombinant nucleic acid comprising a 5' alphavirus replication recognition sequence, an alphavirus subgenomic promoter, a nucleic acid encoding an alphavirus structural protein and a 3' alphavirus replication recognition sequence.

82. The method of claim 79, wherein the helper nucleic acid is a recombinant nucleic acid comprising a promoter and nucleotide sequences encoding one or more alphavirus structural proteins.

83. The method of claim 82, wherein the helper nucleic acid is DNA.

84. The method of claim 82, wherein the promoter is a CMV promoter.

85. The method of claim 82, wherein the helper nucleic acid comprises nucleotide sequences encoding all of the alphavirus structural proteins.

86. The method of claim 79, wherein the helper nucleic acid is a recombinant nucleic acid comprising a 5' alphavirus replication recognition sequence, an IRES element, a nucleotide sequence encoding an alphavirus structural protein and a 3' alphavirus replication recognition sequence.

87. A method of making infectious, defective alphavirus particles, comprising:
   a) introducing into a cell the following:
      i) an alphavirus replicon RNA comprising a 5' alphavirus replication recognition sequence, nucleic acid sequence(s) encoding alphavirus nonstructural proteins, an alphavirus subgenomic promoter, a heterologous nucleic acid sequence and a 3' alphavirus replication recognition sequence; and
      ii) one or more helper nucleic acids encoding alphavirus structural proteins, wherein the helper nucleic acid(s) comprise the recombinant nucleic acid of claim 51, whereby all of the alphavirus structural proteins are produced in the cell; and
   b) producing the alphavirus particles in the cell.

88. A method of making infectious, defective alphavirus particles, comprising:
   a) introducing into a cell the following:
      i) the recombinant replicon RNA of claim 19; and
      ii) one or more helper nucleic acids encoding alphavirus structural proteins, wherein the helper nucleic acid(s) comprise a recombinant nucleic acid comprising:
         a) a 5' alphavirus replication recognition sequence;
         b) an alphavirus subgenomic promoter-IRES-heterologous NOI cassette, which is in the 5' to 3' orientation, wherein the NOI encodes one or more alphavirus structural proteins;
         c) and a 3' alphavirus replication recognition sequence, whereby all of the alphavirus structural proteins are produced in the cell; and
   b) producing the alphavirus particles in the cell.

89. The recombinant nucleic acid of claim 6, wherein the peptide is an immunogen.

90. The recombinant nucleic acid of claim 63, wherein the peptide is an immunogen.

91. An infectious defective alphavirus particle produced by the method of claim 37.

92. An infectious defective alphavirus particle produced by the method of claim 46.

93. An infectious defective alphavirus particle produced by the method of claim 79.

94. An infectious defective alphavirus particle produced by the method of claim 88.

* * * * *

UNITED STATES PATENT AND TRADEMARK OFFICE
CERTIFICATE OF CORRECTION

PATENT NO.       : 7,442,381 B2                                          Page 1 of 1
APPLICATION NO.  : 10/804331
DATED            : October 28, 2008
INVENTOR(S)      : Smith et al.

It is certified that error appears in the above-identified patent and that said Letters Patent is hereby corrected as shown below:

Column 39, Line 46:  Please correct "TABLE 17"
                              To read -- TABLE 18 --

Column 40, Line 2:   Please correct "TABLE 17"
                              To read -- TABLE 18 --

Column 40, Line 38:  Please correct "TABLE 18"
                              To read -- TABLE 19 --

Signed and Sealed this

Third Day of March, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,442,381 B2 |
| APPLICATION NO. | : 10/804331 |
| DATED | : October 28, 2008 |
| INVENTOR(S) | : Smith et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1156 days.

Signed and Sealed this
Twelfth Day of July, 2016

Michelle K. Lee
*Director of the United States Patent and Trademark Office*